US012263166B2

(12) United States Patent
D'Andrea et al.

(10) Patent No.: US 12,263,166 B2
(45) Date of Patent: Apr. 1, 2025

(54) METHODS OF TREATING CANCERS HAVING A BRCA1 AND/OR BRCA2 MUTATION(S)

(71) Applicant: Dana-Farber Cancer Institute, Inc., Boston, MA (US)

(72) Inventors: Alan D'Andrea, Winchester, MA (US); Kah Suan Lim, Boston, MA (US)

(73) Assignee: DANA-FARBER CANCER INSTITUTE, INC., Boston, MA (US)

(*) Notice: Subject to any disclaimer, the term of this patent is extended or adjusted under 35 U.S.C. 154(b) by 0 days.

(21) Appl. No.: 17/811,282

(22) Filed: Jul. 7, 2022

(65) Prior Publication Data

US 2023/0093238 A1    Mar. 23, 2023

Related U.S. Application Data

(63) Continuation of application No. 16/755,686, filed as application No. PCT/US2018/055855 on Oct. 15, 2018, now Pat. No. 11,413,288.

(60) Provisional application No. 62/719,276, filed on Aug. 17, 2018, provisional application No. 62/580,058, filed on Nov. 1, 2017.

(51) Int. Cl.
| | |
|---|---|
| *A61K 31/506* | (2006.01) |
| *A61K 31/423* | (2006.01) |
| *A61K 31/4439* | (2006.01) |
| *A61K 31/454* | (2006.01) |
| *A61K 31/713* | (2006.01) |
| *A61K 38/17* | (2006.01) |
| *A61K 38/45* | (2006.01) |
| *A61K 39/395* | (2006.01) |
| *A61K 45/06* | (2006.01) |
| *A61P 35/00* | (2006.01) |
| *C07K 16/40* | (2006.01) |
| *C12N 15/113* | (2010.01) |

(52) U.S. Cl.
CPC .......... *A61K 31/506* (2013.01); *A61K 31/423* (2013.01); *A61K 31/4439* (2013.01); *A61K 31/454* (2013.01); *A61K 31/713* (2013.01); *A61K 38/1761* (2013.01); *A61K 38/45* (2013.01); *A61K 39/3955* (2013.01); *A61K 45/06* (2013.01); *A61P 35/00* (2018.01); *C07K 16/40* (2013.01); *C12N 15/1137* (2013.01); *C12Y 203/02* (2013.01); *C07K 2317/24* (2013.01); *C07K 2317/54* (2013.01); *C07K 2317/55* (2013.01); *C12N 2310/11* (2013.01); *C12N 2310/14* (2013.01)

(58) Field of Classification Search
None
See application file for complete search history.

(56) References Cited

U.S. PATENT DOCUMENTS

| | | | |
|---|---|---|---|
| 9,518,032 B2* | 12/2016 | D'Andrea | A61K 31/472 |
| 10,653,676 B2 | 5/2020 | D'Andrea et al. | |
| 11,413,288 B2 | 8/2022 | D'Andrea et al. | |
| 2008/0167229 A1 | 7/2008 | D'Andrea et al. | |
| 2009/0062196 A1 | 3/2009 | D'Andrea et al. | |
| 2014/0199327 A1* | 7/2014 | Dixit | G01N 33/5011 |
| | | | 435/6.13 |
| 2015/0344443 A1 | 12/2015 | Maloney et al. | |
| 2017/0035737 A1 | 2/2017 | Yen | |
| 2017/0035746 A1 | 2/2017 | Pouria et al. | |
| 2017/0202810 A1 | 7/2017 | D'Andrea et al. | |
| 2021/0186964 A1 | 6/2021 | D'Andrea et al. | |

FOREIGN PATENT DOCUMENTS

| | | |
|---|---|---|
| WO | WO 2015/108986 | 7/2015 |
| WO | WO 2016/102517 | 6/2016 |

OTHER PUBLICATIONS

Domchek et al (Efficacy and safety of olaparib monotherapy in germline BRCA1/2 mutation carriers with advanced ovarian cancer and three or more lines of prior therapy, Gynecologic Oncology, Feb. 2016, pp. 199-203). (Year: 2016).*
Dexheimer et al (Discovery of ML323 as a Novel Inhibitor of the USP1/UAF1 Deubiquitinase Complex, Probe Reports from the NIH Molecular Libraries, Published Sep. 18, 2014] (Year: 2014).*
Gelmon et al (Olaparib in patients with recurrent high-grade serous or poorly differentiated ovarian carcinoma or triple-negative breast cancer: a phase 2, multicentre, open-label, non-randomised study, The Lancet, Oncology, vol. 12, Sep. 2011) (Year: 2011).*
Evans et al (PALB2 Mutations and Breast-Cancer Risk, N Engl J Med. Aug. 7, 2014; 371(6): 566-568. doi: 10.1056/NEJMe1405784), (Year: 2014).*
Promkan et al., (2009) Int. J. Cancer, 125, 2820-2828.
Su et al., (2002) Int. J. Biochem. & Cell Biol., 34(8), 950-957.
Alan et al., "The fanconi anemia and breast cancer susceptibility pathways", N. Engl. J. Med., May 2010, 362:1909-1919.
Bell et al., "Integrated genomic analyses of ovarian carcinoma," Nature, Dec. 2011, 474(7353):609-15.
Boersma et al., "MAD2L2 controls DNA repair at telomeres and DNA breaks by inhibiting 5' end resection," Nature, May 2015, 521(7553):537-40.
Ceccaldi et al., "Homologous-recombination-deficient tumours are dependent on Poltheta-mediated repair," Nature, Feb. 2015, 518(7538):258-62.
Chaudhuri et al., "Replication fork stability confers chemoresistance in BRCA-deficient cells," Nature, Jul. 2016, 535(7612):382-7.
Choe et al., "Forging Ahead through Darkness: PCNA, Still the Principal Conductor at the Replication Fork," Molecular Cell, Feb. 2017, 65(3):380-92.

(Continued)

*Primary Examiner* — Laura B Goddard
*Assistant Examiner* — Sarah A Alsomairy
(74) *Attorney, Agent, or Firm* — Dana-Farber Cancer Institute, Inc.; Kimberly S. Jordahl

(57) ABSTRACT

The disclosure relates to methods for treating cancers (e.g., cancers having a BRCA1 and/or BRCA2 mutation(s)) by administering to the subject an effective amount of a ubiquitin-specific protease 1 (USP1) inhibitor.

12 Claims, 54 Drawing Sheets

Specification includes a Sequence Listing.

(56) References Cited

OTHER PUBLICATIONS

Choi et al., "Platinum and PARP Inhibitor Resistance Due to Overexpression of MicroRNA-622 in BRCA1-Mutant Ovarian Cancer," Cell Reports, Jan. 2016, 14(3):429-39.
Cohn et al., "A UAF1-containing multisubunit protein complex regulates the Fanconi anemia pathway," Molecular Cell, Dec. 2007, 28(5):786-97.
Cohn et al., "UAF1 is a subunit of multiple deubiquitinating enzyme complexes," The Journal of Biological Chemistry, Feb. 2009, 284(8):5343-51.
Cukras et al., "The USP1-UAF1 complex interacts with RAD51AP1 to promote homologous recombination repair," Cell Cycle, Jun. 2016, 15(19):2636-46.
Dahlberg et al., "The WD40-repeat proteins WDR-20 and WDR-48 bind and activate the deubiquitinating enzyme USP-46 to promote the abundance of the glutamate receptor GLR-1 in the ventral nerve cord of Caenorhabditis elegans," Journal of Biological Chemistry, Feb. 2014, 289(6):3444-56.
D'Andrea et al., "Deubiquitinating enzymes: a new class of biological regulators," Critical Reviews in Biochemistry and Molecular Biology, Jan. 1998, 33(5):337-52.
D'Andrea, "Abstract IA10: Fanconi anemia and novel drug targets", Cancer Research, Oct. 2014, 74(20): Suppl. p. IA10, Abstract Only.
Davis et al., "Ubiquitin-specific proteases as druggable targets," Drug Target Review, 2015, 2(3):60, 9 pages.
Dungrawala et al., "The Replication Checkpoint Prevents Two Types of Fork Collapse without Regulating Replisome Stability," Molecular Cell, Sep. 2015, 59(6):998-1010.
Eletr et al., "Regulation of proteolysis by human deubiquitinating enzymes," Biochimica et Biophysica Acta (BBA)-Molecular Cell Research, Jan. 2014, 1843(1):114-28.
EP Partial Supplementary European Search Report in European Appln. No. 18873193.9, dated Jul. 9, 2021, 21 pages.
Farmer et al., "Targeting the DNA repair defect in BRCA mutant cells as a therapeutic strategy," Nature, Apr. 2005, 434(7035):917-921.
Harrigan et al., "Deubiquitylating enzymes and drug discovery: emerging opportunities," Nat Rev Drug Discov, Jan. 2018, 17(1):57-78.
Huang et al., "Regulation of monoubiquitinated PCNA by DUB autocleavage," Nature Cell Biology, Mar. 2006, 8(4):341-7.
Jaspers et al., "Loss of 53BP1 causes PARP inhibitor resistance in Brca1-mutated mouse mammary tumors," Cancer Discovery, Jan. 2013, 3(1):68-81.
Jones et al., "Dysregulation of DNA polymerase kappa recruitment to replication forks results in genomic instability," The EMBO Journal, 2012;31(4):908-18.
Kais et al., "FANCD2 maintains fork stability in BRCA1/2-deficient tumors and promotes alternative end-joining DNA repair", Cell Rep., Jun. 2016, 15:2488-2499.
Kee et al., "WDR20 regulates activity of the USP12· UAF1 deubiquitinating enzyme complex," Journal of Biological Chemistry, Feb. 2010, 285(15):11252-7.
Koboldt et al.,, "Comprehensive molecular portraits of human breast tumors," Nature, Sep. 2012, 490(7418):61, 10 pages.
Komander et al., "The ubiquitin code," Annual Review of Biochemistry, Apr. 2012, 81:203-29.
Lecona et al., "USP7 is a SUMO deubiquitinase essential for DNA replication," Nature Structural & Molecular Biology, Apr. 2016, 23(4):270-7.
Ledermann et al., "Olaparib maintenance therapy in patients with platinum-sensitive relapsed serous ovarian cancer: a preplanned retrospective analysis of outcomes by BRCA status in a randomised phase 2 trial," The Lancet Oncology, Jul. 2014, 15(8):852-61.
Ledermann et al., "Overall survival in patients with platinum-sensitive recurrent serous ovarian cancer receiving olaparib maintenance monotherapy: an updated analysis from a randomised, placebo-controlled, double-blind, phase 2 trial," The Lancet Oncology, Nov. 2016, 17(11):1579-89.
Leung "A rapid and efficient method to purify proteins at replication forks under native conditions," Biotechniques, Oct. 2013, 55(4):204-6.
Li et al., "Allosteric activation of ubiquitin-specific proteases by β-propeller proteins UAF1 and WDR20," Molecular cell, Jul. 2016, 63(2):249-60.
Liang et al., "A selective USP1-UAF1 inhibitor links deubiquitination to DNA damage responses," Nature Chemical Biology, Feb. 2014, 10(4):298-304.
Liang et al., "Promotion of RAD51-Mediated Homologous DNA Pairing by the RAD51AP1-UAF1 Complex," Cell Reports, Jun. 2016, 15(10):2118-26.
Lim et al., "Abstract 333: USP1 is required for replication fork stability in BRCA1-deficient tumors", Cancer Research, Jul. 2018, 78(13):333, Abstract Only.
Lim et al., "USP1 Is Required for Replication Fork Protection in BRCA1-Deficient Tumors," Mol Cell., Dec. 2018, 72(6):925-941.
Medicine.nus.edu.sg, [online], Suan et al., "Seminar: USP1 maintains Replication Fork Stability in BRCA1-Deficient Tumour Cells," Oct. 16, 2017, retrieved on Jun. 24, 2021, retrieved from URL<https://medicine.nus.edu.sg/seminar-usp1-maintains-replication-fork-stability-in-brca1-deficient-tumour-cells/>, 2 pages.
Mistry et al., "Small-molecule inhibitors of USP1 target ID1 degradation in leukemic cells.," Molecular Cancer Therapeutics., Dec. 2013, 12(12):2651-62.
Moynahan et al., "Brca1 controls homology-directed DNA repair," Molecular Cell, Oct. 1999, 4(4):511-8.
Nickoloff et al., "Drugging the cancers addicted to DNA repair," JNCI: Journal of the National Cancer Institute, Nov. 1, 2017 109(11):djx059, 13 pages.
Nijman et al., "A genomic and functional inventory of deubiquitinating enzymes," Cell, Dec. 2005, 123(5):773-86.
Nik-Zainal et al., "Landscape of somatic mutations in 560 breast cancer whole-genome sequences," Nature, Nov. 2016, 534(7605):47-54.
Oza et al., "Olaparib combined with chemotherapy for recurrent platinum-sensitive ovarian cancer: a randomised phase 2 trial," The Lancet Oncology, Jan. 2015, 16(1):87-97.
Pathania et al., "BRCA1 haploinsufficiency for replication stress suppression in primary cells," Nature Communications, Nov. 2014, 5:5496, 15 pages.
PCT International Preliminary Report on Patentability in International Application No. PCT/US2018/055855, dated May 5, 2020, 8 pages.
PCT International Search Report and Written Opinion in International Application No. PCT/US2018/055855, dated Jan. 17, 2019, 11 pages.
Rahme et al., "PDGF Engages an E2F-USP1 Signaling Pathway to Support ID2-Mediated Survival of Proneural Glioma Cells," Cancer Res., May 2016, 76(10):2964-76.
Schlacher et al., "A distinct replication fork protection pathway connects Fanconi anemia tumor suppressors to RAD51-BRCA1/2," Cancer Cell, Jul. 2012, 22(1):106-16.
Shinagare et al., "Advanced high-grade serous ovarian cancer: Frequency and timing of thoracic metastases and the implications for chest imaging follow up", Radiology, Jun. 2015, 277:733-740.
Sirbu et al., "Analysis of protein dynamics at active, stalled, and collapsed replication forks," Genes & Development, May 2011, 25(12):1320-7.
Sowa et al., "Defining the human deubiquitinating enzyme interaction landscape," Cell, Jul. 2009, 138(2):389-403.
Stephens et al., "The landscape of cancer genes and mutational processes in breast cancer," Nature, Aug. 2012, 486(7403):400-4.
Tian et al., "BRCA1 promotes the ubiquitination of PCNA and recruitment of translesion polymerases in response to replication blockade," Proceedings of the National Academy of Sciences of the United States of America, Oct. 2013, 110(33):13558-63.
Toft et al., "Minireview: Basal-like breast cancer from molecular profiles to targeted therapies", Mol. Endocrinol., Sep. 2010, 25:199-211.

(56) References Cited

OTHER PUBLICATIONS

Villamil et al., "The WD40-repeat protein-containing deubiquitinase complex: catalysis, regulation, and potential for therapeutic intervention," Cell biochemistry and Biophysics, Jun. 2013, 67(1):111-26.
Walker et al., "Distinct roles of STAT3 and STAT5 in the pathogenesis and targeted therapy of breast cancer," Molecular and Cellular Endocrinology, Jan. 2014, 382(1):616-621.
Willis et al., "BRCA1 controls homologous recombination at Tus/Ter-stalled mammalian replication forks," Nature, Apr. 2014, 510(7506):556-9.
Xu et al., "REV7 counteracts DNA double-strand break resection and affects PARP inhibition," Nature, May 2015, 521(7553):541-4.
Yin et al., "Structural Insights into WD-Repeat 48 Activation of Ubiquitin-Specific Protease 46," Structure, Nov. 2015, 23(11):2043-54.
Kim et al., Developmental Cell, 16, 314-320 Feb. 17, 2009.
Simoneau et al., Cancer Res (2023), 83 (7_Supplement):4968.

\* cited by examiner

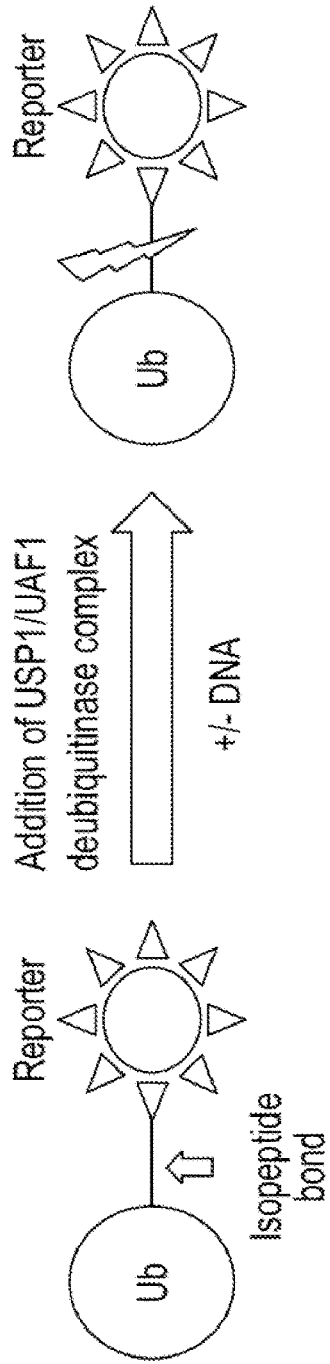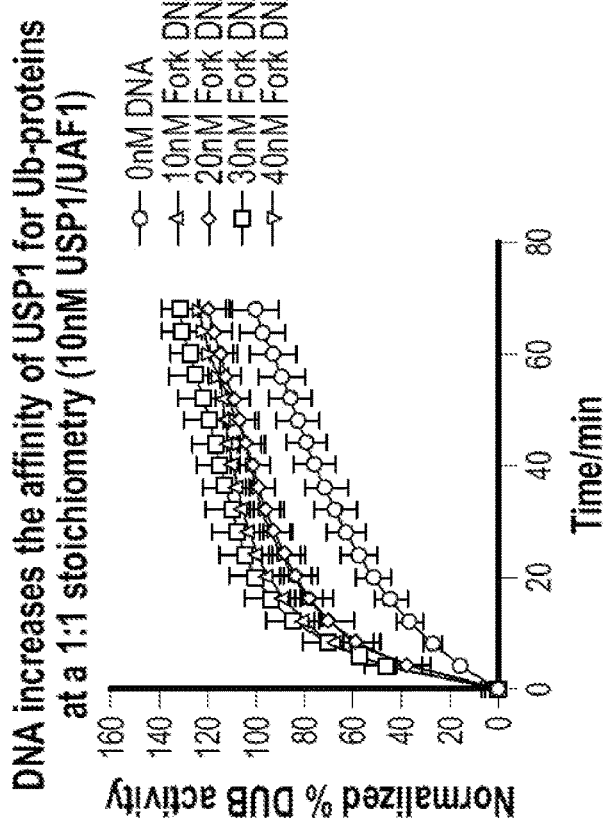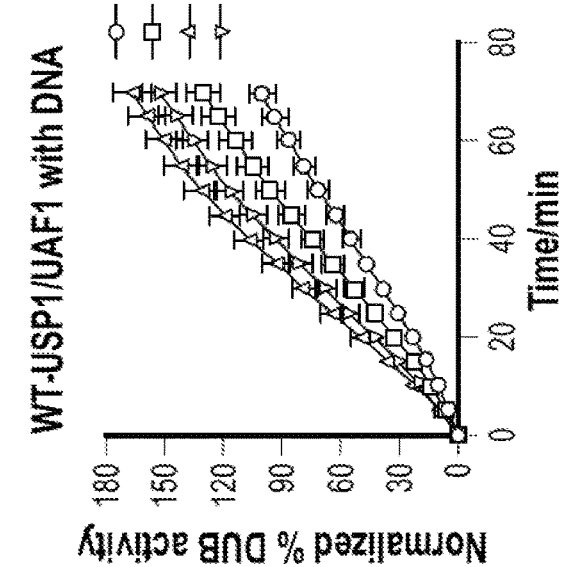
FIG. 4A
FIG. 4C
FIG. 4B

| | $K_m$ (μM) | $K_{cat}$ (S$^{-1}$) | $K_{cat}/K_m$ (μM/s) |
|---|---|---|---|
| - DNA | 0.79 (±0.08) | 0.65 (±0.02) | 0.82 |
| + DNA | 0.33 (±0.07) | 0.86 (±0.04) | 2.61 |

| Gene | % mutated in USP1-high (top 10%) | % mutated in USP1-low (bottom 90%) | P value |
|---|---|---|---|
| TP53 | 82.98% | 32.45% | 2.14E-11 |
| BRCA1 | 17.02% | 2.16% | 7.58E-05 |
| KCNH6 | 8.51% | 0% | 9.44E-05 |
| PRPF38B | 8.51% | 0% | 9.44E-05 |
| USH2A | 17.02% | 3.37% | 6.68E-04 |

| Top 20 genes correlated with USP1 expression in breast carcinoma (RF proteins highlighted) | |
|---|---|
| Gene Symbol | Pearson Score |
| MSH2 | 0.67 |
| MSH6 | 0.66 |
| RFC4 | 0.64 |
| STIL | 0.63 |
| LRRC42 | 0.62 |
| UBXN2A | 0.61 |
| CTPS1 | 0.61 |
| TRA2B | 0.61 |
| RNF138 | 0.61 |
| LRRC40 | 0.61 |
| MMS22L | 0.61 |
| RAD51AP1 | 0.6 |
| PRPF38A | 0.6 |
| GPSM2 | 0.6 |
| RQCD1 | 0.59 |
| SMC4 | 0.59 |
| TYMS | 0.58 |
| CHAF1B | 0.58 |
| DOCK7 | 0.58 |
| FANCE | 0.57 |

| Top 20 genes correlated with USP1 expression in ovarian carcinoma (RF proteins highlighted) | |
|---|---|
| Gene Symbol | Pearson Score |
| DEPDC1 | 0.6 |
| ALG6 | 0.6 |
| STIL | 0.59 |
| PRPF38A | 0.56 |
| SERBP1 | 0.55 |
| MCM6 | 0.54 |
| CCNE2 | 0.54 |
| LRRC42 | 0.54 |
| ATG4C | 0.54 |
| GPSM2 | 0.54 |
| ORC1 | 0.53 |
| SMC4 | 0.53 |
| FBXO5 | 0.52 |
| ATAD2 | 0.52 |
| ECT2 | 0.51 |
| ITGB3BP | 0.5 |
| TCF19 | 0.49 |
| LRRC40 | 0.49 |
| BTF3L4 | 0.49 |
| HELLS | 0.48 |

FIG. 9A

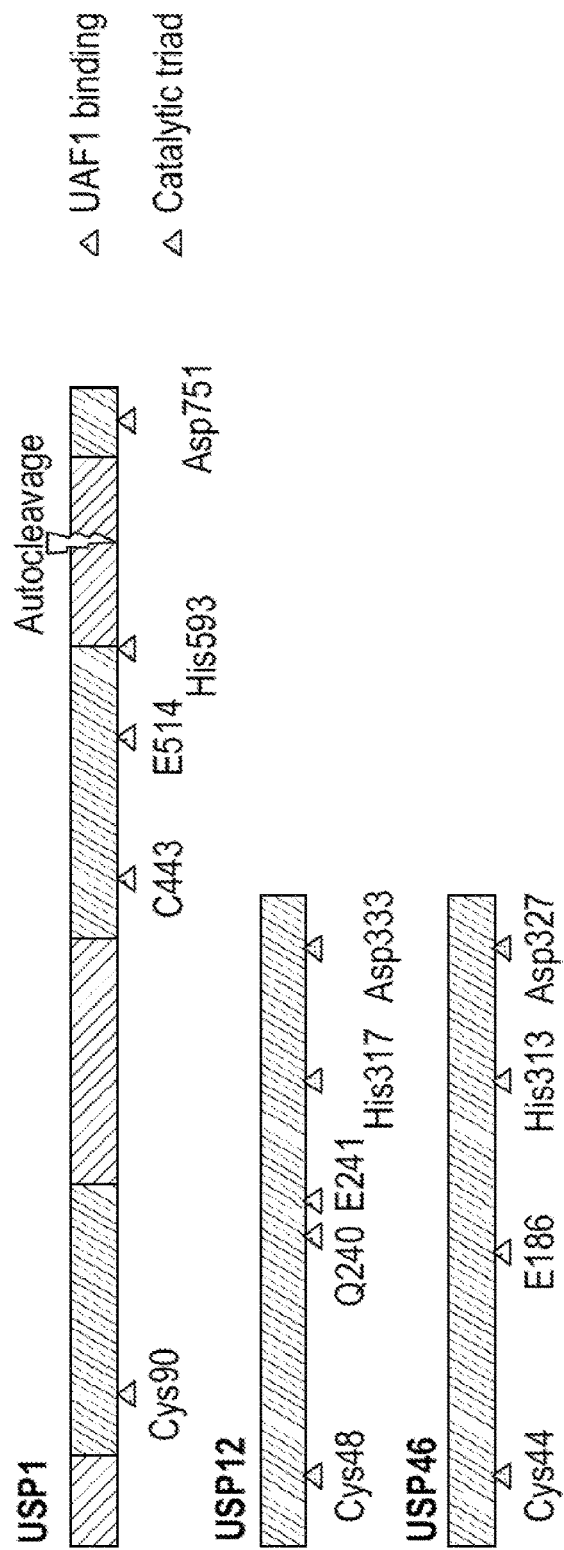
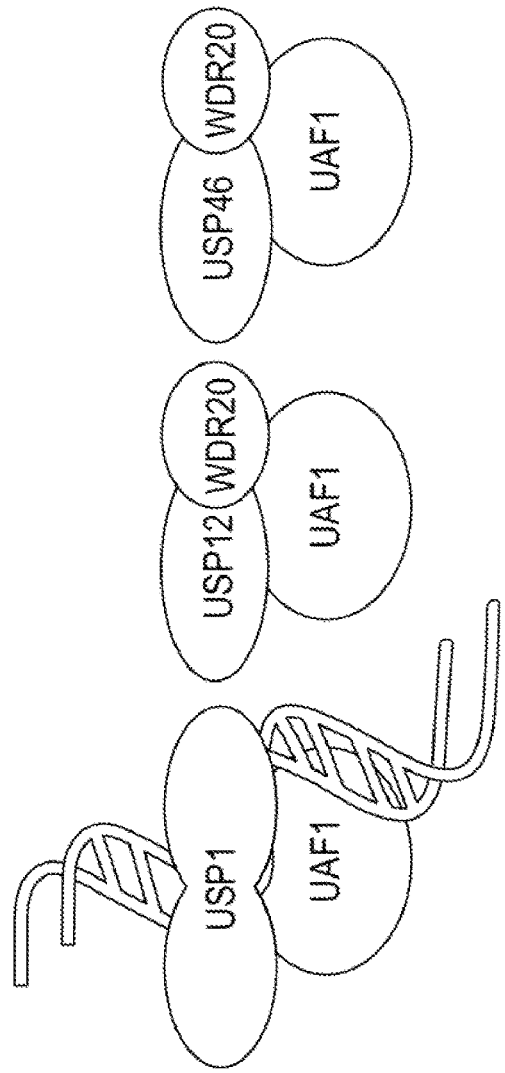
FIG. 10A
FIG. 10B

```
USP1   MPGVIPSESNGLSRGSPSKKNRLSLKFFQKKEIKRALDFTDSQENEEKASEYRASEIDQV  60
USP12  ------------------------------MEIL------------MTVSKFASI      13
USP46  --------------------------------------------MTVRNIASI         9

V-----PAAQSSPINCEKRENLLPFVGLNNLGNTCYLNSILQVLYFCPGFKSGVKHLFNI  115
       CTMGANASALEKEIGPEQEPVNEHYFGLVNFGNTCYCNSVLQALYFCRPFEREKVLAYKSQ  73
       CNMGTNASALEKDIGPEQEPINEHYFGLVN-----------ALYFCRPFRENVLAYKAQ  57
            *;. *****

ISRKKEALKDEANQKDKGNCKEDSLASYELICSLQSLIISVEQLQASFLLNPEKYTDELA  175
       P-RKKESL---------LTCL------------ADLFHSIAT---------QKKKVGV  100
       Q-KKKENL---------LTCL------------ADLFHSIAT---------QKKKVGV  84

TQPRRLLNTLRELNPMYEGYLQHDAGEVLQCILGNIQETCQLLKKEEVKNVAELPTKVEE  235
       IPPKKFITRLRKENELFDNYMQQDAHEFLNYLLNTIADILQEERKQEKQ-----------  149
       IPPKKFISRLRKENDLFDNYMQQDAHEFLNYLLNTIADILQEERKQEKQ-----------  133
          *:;::. **:. * :.. *.****.** :* .:* *;

IPHPKEEMNGINSIEMDSMRHSEDFKEKLPKGNGKRKSDTEFGNMKKKVKLSKEHQSLEE  295
       -----------------------NGRLPNGN-----------------------------  157
       -----------------------NGKLKNGN-----------------------------  141
                              ; :*  ;**

NQRQTRSKRKATSDTLESPPKIIPKYISENESPRPSQKKSRVKINWLKSATKQPSILSKF  355
       ------------------------------------------------------------  157
       ------------------------------------------------------------  141

CSLGKITTNQGVKGQSKENECDPEEDLGKCESDNTTNGCGLESPGNTVTPVNVNEVKPIN  415
       ----------------------------------------------IDNENN--------  163
       ----------------------------------------------MNEPAE--------  147

KGEEQIGFELVEKLFQGQLVLRTRCLECESLTERREDFQDISVPVQEDELSKVEESSEIS  475
       --NSTPDPTWVHEIFQGTLTNETRCLNCETISSKQEDFLDLSVDVEQNT-----------  210
       --NNKPELTWVHEIFQGTLTNETRCLNCETVSSKQEDFLDLSVDVEQNT-----------  194
        *  .:* *** *;,.**** **:....* *** *:** *::;            .:

PEPKTEMKTLRWAISQFASVERIVGEDKYFCENCHHYTEAERSLLFDKMPEVITIHLKCF  535
       --------SITHCLRGFSNTETLCSEYKYYCEECRSKQEAHKRMKVKKLPMILALHLKRF  262
       --------SITHCLRDFSNTETLCSEQKYYCETCCSKQEAQKRMRVKKLPMILALHLKRF  246
               **.: : .. *.*...*. *.*****.**.:* *

AASGLEFDCYGGGLSKINTPLLTPLKLSLEEWST--KPTNDSYGLFAVVMHSGITISSGH  593
       KYMDQLH-----RVTKLSYRVVFPLELRLFNTSGDATNPDRMYDLVAVVVHCGSGPNRGH  317
       KYMEQLH-----RVTKLSYRVVFPLELRLFNTSSDAVNLDRMYDLVAVVVHCGSGPNRGH  301
         .**     * * .***.* *                          :: **.*.* : *

YTASVKVTDLNSLELDKGNFVVDQMC---EIGKPEPLNEEEARGVVENYNDEEVSIRVGG  650
       YIAIVKSHDFWLLFDDDIVEKIDAQAIEEFYGLTSDISKNSESGYILFYQSRD-------  370
       YITIVKSHGFWLLFDDDIVEKIDAQAIEEFYGLTSDISKNSESGYILFYQSRE-------  354
        *:..; *  :.: *   ::                              .:*

NTQPSKVLNKKNVEAIGLLGGQKSKADYELYNKASNPDKVASTAFAENRNSETSDTTGTH  710
       ------------------------------------------------------------  370
       ------------------------------------------------------------  354

ESDRNKESSDQTGINISGFENKISYVVQSLKEYEGKWLLFDDSEVKVTEEKDFLNSLSPS  770
       ------------------------------------------------------------  370
       ------------------------------------------------------------  354
```

FIG. 10C

```
                    Exon 2              Exon 3
              I  L  E  C  P  I  C  L  E  L  I  K  E
              ATCTTAGAGTGTCCATCTGTCTGGAGTTGATCAAGGAA
              SEQ ID NO: 12

I  L  E  C  P  I     V  W  S   stop
          ATCTTAGAGTGTCCATC GTCTGGAGT TGA CAAGGAA   Allele 1
          SEQ ID NO: 12

I  L  E  C  P  I        F  W  S   stop
          ATCTTAGAGTGTCCATCT TCTGGAGT TGA CAAGGAA   Allele 2
          SEQ ID NO: 14
```

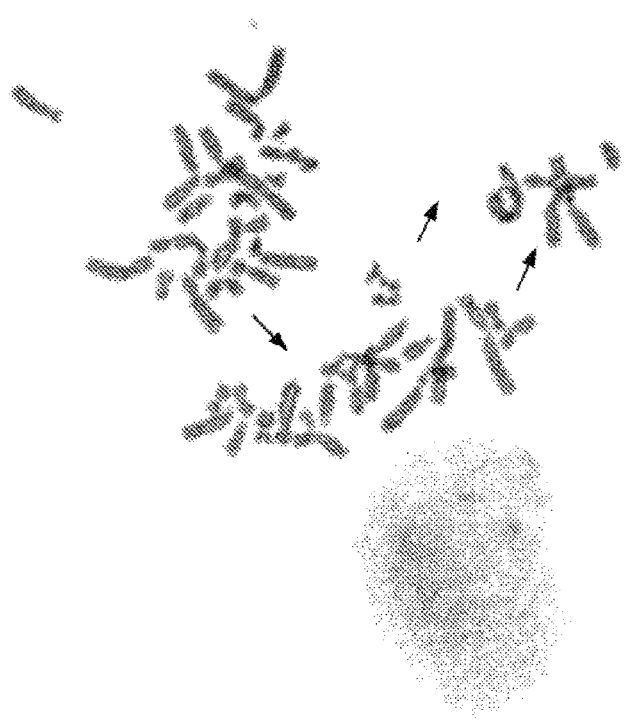
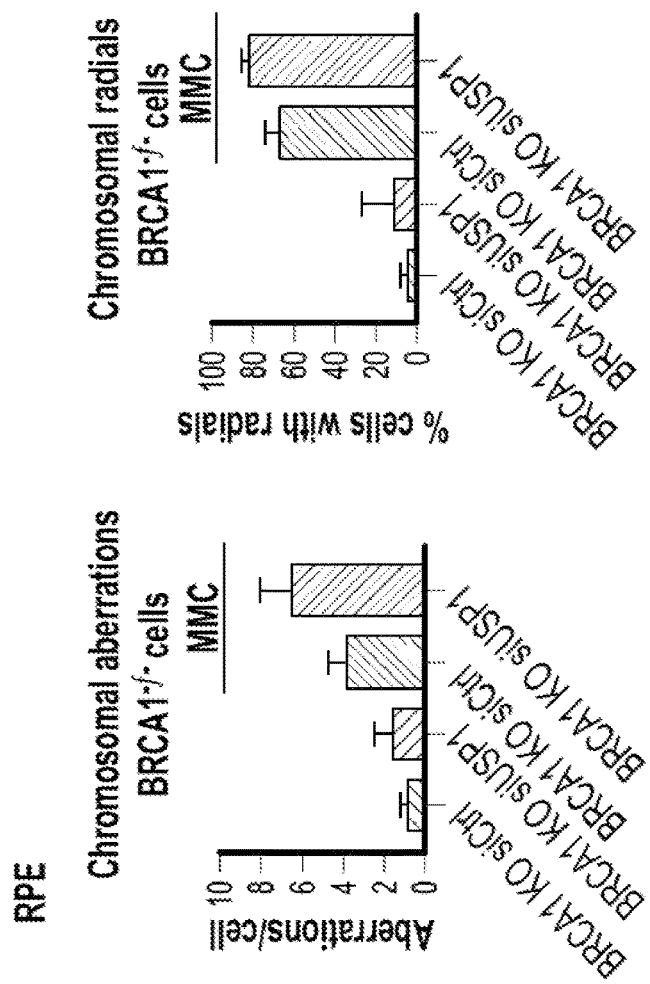
FIG. 20C
FIG. 20D
FIG. 20E

METHODS OF TREATING CANCERS HAVING A BRCA1 AND/OR BRCA2 MUTATION(S)

CROSS-REFERENCE TO RELATED APPLICATIONS

This application is a continuation and claims priority of U.S. application Ser. No. 16/755,686, filed Apr. 13, 2020, which is a U.S. National Stage application, and claims priority of International Application No. PCT/US2018/055855, filed Oct. 15, 2018, which claims priority of U.S. Provisional Application No. 62/580,058, filed Nov. 1, 2017, and U.S. Provisional Application No. 62/719,276, filed Aug. 17, 2018. The contents of all the prior applications are incorporated by reference herein in their entirety.

FEDERALLY SPONSORED RESEARCH OR DEVELOPMENT

This invention was made with government support under grant R01 DK043889, awarded by the National Institutes of Health. The Government has certain rights in the invention.

SEQUENCE LISTING

This application contains a Sequence Listing that has been submitted electronically as an XML file named 00530-0339002.xml. The XML file, created on Jul. 8, 2022, is 27000 bytes in size. The material in the XML file is hereby incorporated by reference in its entirety.

TECHNICAL FIELD

The disclosure relates to methods for treating cancers.

BACKGROUND

BRCA1 and BRCA2 are DNA repair genes that are frequently mutated in breast and ovarian cancers, and play important roles in homologous-recombination (HR) (1-3). As a result, BRCA1/2 deficient tumor cells are hyperdependent on DNA repair factors.

PARP inhibitors have had significant success in increasing progression-free survival in BRCA1/2 deficient ovarian tumors (8-10) and remain the only FDA-approved "synthetic lethal" therapeutic agents against BRCA deficient tumors. However, many cancer cells develop therapeutic resistance to PARP inhibitors (11-15). Thus, there is an urgent need to develop new therapies to treat these cancers.

SUMMARY

The disclosure relates to methods for treating cancers, e.g., by a ubiquitin-specific protease 1 (USP1) inhibitor. More specifically, the disclosure provides methods of treating cancers comprising a BRCA1 and/or BRCA2 mutation with a USP1 inhibitor without administering a crosslinking agent. In certain instances, the cancer is PARP-inhibitor resistant.

In one aspect, the disclosure provides methods for treating a human subject having, or at risk of developing, a cancer. The methods involve administering to the human subject an effective amount of a ubiquitin-specific protease 1 (USP1) inhibitor, wherein the human subject is identified as having cells having a BRCA1 and/or BRCA2 mutation, and the USP1 inhibitor is administered as a monotherapy.

In some embodiments, the USP1 inhibitor is ML323, C527, pimozide, SJB019, or SJB2-043.

In some embodiments, the cancer is resistant to a poly (adenosine diphosphate [ADP]) ribose polymerase (PARP) inhibitor. In some embodiments, the cancer has intrinsic PARP inhibitor resistance. In some embodiments, the cancer has acquired PARP inhibitor resistance.

In some embodiments, the cancer is resistant to a cross-linking agent. In some embodiments, the cross-linking agent is cisplatin, mitomycin, or busulfan.

In some embodiments, a PARP inhibitor and/or a cross-linking agent is not administered to the human subject.

In some embodiments, the cancer is breast cancer, prostate cancer, pancreatic cancer, fallopian tube cancer, peritoneal cancer, or ovarian cancer. In some embodiments, the cancer is a basal-like carcinoma or a luminal breast cancer. In some embodiments, the cancer is a triple-negative breast cancer. In some embodiments, the cancer is a high-grade serous ovarian carcinoma.

In some embodiments, the methods involve identifying the human subject as having one or more cancer cells that have a BRCA1 mutation. In some embodiments, the methods involve identifying the human subject as having one or more cancer cells that have a BRCA1 mutation and are PARP inhibitor-resistant. In some embodiments, the methods involve identifying the subject as having one or more cancer cells that have a BRCA2, BRCA1 and BRCA2, or PALB2 mutation.

In some embodiments, the USP1 inhibitor is an inhibitory nucleic acid. In some embodiments, the inhibitory nucleic acid is a small interfering RNA molecule or an antisense nucleic acid.

In some embodiments, the USP1 inhibitor is an anti-USP1 antibody or antigen binding fragment thereof. In some embodiments, the anti-USP1 antibody or antigen-binding fragment thereof is a monoclonal antibody, a polyclonal antibody, a chimeric antibody, a humanized antibody, a single chain antibody, a Fab fragment, or a F(ab')2 fragment.

In one aspect, the disclosure relates to methods for treating a human subject having, or at risk of developing, a cancer comprising a BRCA1 and/or BRCA2 mutation. The methods involve administering to the human subject a therapy comprising a ubiquitin-specific protease 1 (USP1) inhibitor, wherein the human subject is not administered a cross-linking agent.

In some embodiments, the USP1 inhibitor is ML323, C527, pimozide, SJB019, or SJB2-043. In some embodiments, the USP1 inhibitor is an inhibitory nucleic acid.

In some embodiments, the cancer is resistant to a PARP inhibitor. In some embodiments, the cancer is resistant to a cross-linking agent.

In some embodiments, the methods involve identifying the human subject as having one or more cancer cells that have a BRCA1 mutation.

In some embodiments, the methods involve identifying the human subject as having one or more cancer cells that have a BRCA1 mutation and that are PARP inhibitor-resistant.

In some embodiments, the cancer comprising a BRCA1 and/or BRCA2 mutation is a breast cancer, ovarian cancer, prostate cancer, pancreatic cancer, fallopian tube cancer, peritoneal cancer, or Fanconi anemia subtype (FA-D1).

In another aspect, the disclosure relates to methods for treating a human subject having, or at risk of developing, a cancer. The methods involve administering to the human subject an effective amount of a USP1 inhibitor and a PARP inhibitor, wherein the subject is identified as having a BRCA1 and/or BRCA2 mutation.

In some embodiments, the USP1 inhibitor is ML323, C527, pimozide, SJB019, or SJB2-043. In some embodiments, the USP1 inhibitor is an inhibitory nucleic acid.

In some embodiments, the USP1 inhibitor is an anti-USP1 antibody. In some embodiments, the cancer is resistant to a cross-linking agent.

In some embodiments, the methods involve identifying the human subject as having one or more cancer cells that have a BRCA1 mutation. In some embodiments, the methods involve identifying the human subject as having one or more cancer cells that have a BRCA1 and BRCA2 mutation.

In one aspect, the disclosure relates to methods for treating a subject having, or at risk of developing, a cancer. The methods involve identifying the subject as having one or more cancer cells that have a BRCA1 and/or BRCA2 mutation; and administering to the human subject an effective amount of a USP1 inhibitor.

In some embodiments, the subject has one or more cancer cells that have a BRCA1 mutation. In some embodiments, the subject has one or more cancer cells that have a BRCA1 and BRCA2 mutation.

In some embodiments, the USP1 inhibitor is administered as a monotherapy.

In some embodiments, the USP1 inhibitor is ML323, C527, pimozide, SJB019, or SJB2-043. In some embodiments, the USP1 inhibitor is an inhibitory nucleic acid.

In some embodiments, the cancer is resistant to a PARP inhibitor. In some embodiments, the cancer is resistant to a cross-linking agent.

In one aspect, the disclosure relates to methods of decreasing replication fork stability in a cell that has a BRCA1 and/or BRCA2 mutation. The methods involve contacting the cell with an effective amount of a USP1 inhibitor.

In some embodiments, the cell is a cancer cell.

In some embodiments, the USP1 inhibitor is ML323, C527, pimozide, SJB019, or SJB2-043. In some embodiments, the USP1 inhibitor is an inhibitory nucleic acid or anti-USP1 antibody.

In some embodiments, the cancer cell is a breast, ovarian, prostate, peritoneal, fallopian tube, or pancreatic cancer cell.

In one aspect, the disclosure relates to methods of killing a cell that has a BRCA1 and/or BRCA2 mutation. The methods involve contacting the cell with an effective amount of a USP1 inhibitor.

In some embodiments, the cell is a cancer cell.

In some embodiments, the USP1 inhibitor is ML323, C527, pimozide, SJB019, or SJB2-043. In some embodiments, the USP1 inhibitor is an inhibitory nucleic acid or an anti-USP1 antibody or USP1-binding fragment thereof.

In one aspect, the disclosure relates to methods of treating a human subject having, or at risk of developing, a cancer. The methods involve administering to the subject an effective amount of a USP1 inhibitor; and increasing the expression or activity of RING-Type E3 Ubiquitin Transferase RAD18.

In some embodiments, the subject has one or more cells that are BRCA1 deficient. In some embodiments, the subject has one or more cells that are BRCA2 deficient.

In some embodiments, the methods involve administering a vector comprising a nucleic acid encoding Rad18 to the human subject. In some embodiments, the methods further involve administering a vector comprising a nucleic acid encoding PCNA to the human subject.

In one aspect, the disclosure relates to methods for treating a human subject having a basal-like carcinoma. The methods involve administering to the human subject an effective amount of a USP1 inhibitor without administering a cross-linking agent.

In some embodiments, the USP1 inhibitor is a small molecule inhibitor. In some embodiments, the USP1 inhibitor is a nucleic acid or antibody.

In one aspect, the disclosure relates to methods for treating a human subject having a triple negative breast cancer. The methods involve administering to the human subject an effective amount of a USP1 inhibitor without administering a cross-linking agent.

In some embodiments, the USP1 inhibitor is a small molecule inhibitor, a nucleic acid, or an antibody.

In one aspect, the disclosure relates to methods of treating a human subject having a high grade cancer. The methods involve administering to the human subject in need thereof an effective amount of a USP1 inhibitor without administering a cross-linking agent.

In some embodiments, the USP1 inhibitor is a small molecule inhibitor, a nucleic acid, or an antibody. In some embodiments, the high grade cancer is high grade serous ovarian cancer.

In one aspect, the disclosure also provides methods of treating a human subject having a cancer. The methods involve administering to the human subject an effective amount of a USP1 inhibitor, wherein the USP1 inhibitor is administered as a monotherapy, and the subject has one or more cells that have an increased activity or expression of USP1 and/or Rad18.

In some embodiments, the USP1 inhibitor is ML323, C527, pimozide, SJB019, or SJB2-043. In some embodiments, the USP1 inhibitor is an inhibitory nucleic acid or an anti-USP1 antibody or USP1-binding fragment thereof.

In another aspect, the disclosure relates to methods of treating a human subject having a cancer. The methods involve administering to the human subject an effective amount of a USP1 inhibitor, wherein the USP1 inhibitor is administered as a monotherapy, and the subject has one or more cells that have a defect in homologous recombination related to BRCA1 or BRCA2.

In some embodiments, the USP1 inhibitor is ML323, C527, pimozide, SJB019, or SJB2-043. In some embodiments, the USP1 inhibitor is an inhibitory nucleic acid or an anti-USP1 antibody or USP1-binding fragment thereof.

In another aspect, the disclosure relates to methods for treating a human subject having a cancer. The methods involve administering to the human subject an effective amount of a UAF1 inhibitor, wherein the human subject is identified as having a BRCA1 and/or BRCA2 mutation.

In some embodiments, the UAF1 inhibitor is an inhibitory nucleic acid.

In one aspect, the disclosure relates to methods of treating a human subject who has a PARP inhibitor-resistant cancer, wherein one or more of the cancer cells(s) has/have a mutation in BRCA1 and/or BRCA2, the method comprising administering to the human subject a therapeutically effective amount of a USP1 inhibitor without administering a cross-linking agent.

In some embodiments, the cancer is a breast cancer, ovarian cancer, prostate cancer, pancreatic cancer, fallopian tube cancer, peritoneal cancer, or Fanconi anemia subtype (FA-D1).

In some embodiments, the USP1 inhibitor is a small molecule inhibitor, a nucleic acid, or an anti-USP1 antibody or USP1-binding fragment thereof. In some embodiments, the USP1 inhibitor is ML323, C527, pimozide, SJB019, or SJB2-043.

In one aspect, the disclosure also provides methods of determining that a cell is BRCA1 deficient or BRCA2 deficient. The methods include the steps of contacting the cell with an effective amount of a USP1 inhibitor; and determining that the USP1 inhibitor induces cell death or increases fork instability, thereby determining that the cell is BRCA1 deficient or BRCA2 deficient.

In another aspect, the disclosure provides methods of identifying a subject as having BRCA1 deficiency or BRCA2 deficiency. The methods include the steps of obtaining a tissue sample from the subject; contacting the tissue sample with an effective amount of a USP1 inhibitor; determining that the USP1 inhibitor induces cell death or increases fork instability in the tissue sample, thereby identifying the subject as having BRCA1 deficiency or BRCA2 deficiency. In some embodiments, the tissue sample is a tumor sample.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 4A. Schematic of ubiquitin reporter assays used.

FIG. 4B. Ub-CHOP2 (Life Sensors) deubiquitination assay measuring WT-USP1/UAF1 deubiquitinating activity with no DNA, ssDNA, dsDNA and fork DNA. Deubiquitinating activity of WT-USP1/UAF1 with no DNA is significantly less compared to ssDNA ($p<0.0001$), dsDNA ($p<0.0001$) and fork DNA ($p<0.0001$).

FIG. 4C. Ub-AMC (Boston Biochem) deubiquitination assay measuring WT-USP1/UAF1 deubiquitination activity with increasing concentrations of fork DNA.

FIG. 9A. Table of top 20 genes co-expressed with USP1 in breast cancers (left) and ovarian cancers (right). Co-expression analyses were performed using data from TCGA breast and ovarian cancer datasets. Replication fork proteins (based on mass spectrometry data from Dungrawala et. al) are highlighted in yellow.

FIG. 10A. Schematic representation of homologous regions (blue) and non-homologous (gray) between USP1, USP12 and USP46.

FIG. 10B. Representations of USP1/UAF1/DNA complex, USP12/UAF1/WDR$_{20}$ complex and USP46/UAF1/WDR$_{20}$ complex.

FIG. 10C. Alignment of USP1 (SEQ ID NO: 9), USP12 (SEQ ID NO: 10) and USP46 (SEQ ID NO: 11), with non-homologous regions highlighted grey.

FIG. 20C. Quantitation of the MMC-induced chromosomal aberrations for BRCA1-deficient RPE cells with siRNA-mediated knockdown of USP1 that were exposed to Mitomycin C (MMC) (20 ng/ml) for 48 hrs, and metaphase spread of chromosomes were scored for chromosomal abnormalities.

FIG. 20D. Percentages of cells with radials for BRCA1-deficient RPE cells with siRNA-mediated knockdown of USP1 that were exposed to Mitomycin C (MMC) (20 ng/ml) for 48 hrs.

FIG. 20E. Representative image of the metaphase spreads of the chromosomes.

DETAILED DESCRIPTION

Figure 1C:
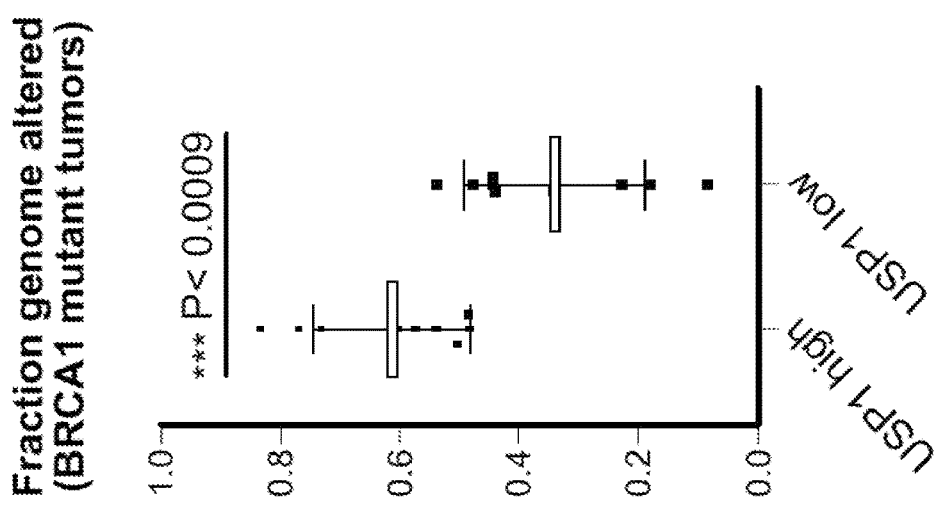
FIG. 1C. Fraction of genome altered in BRCA1 mutant breast cancers with high USP1 expression levels or low USP1 expression levels were plotted using data from TCGA.
Figure 1B:
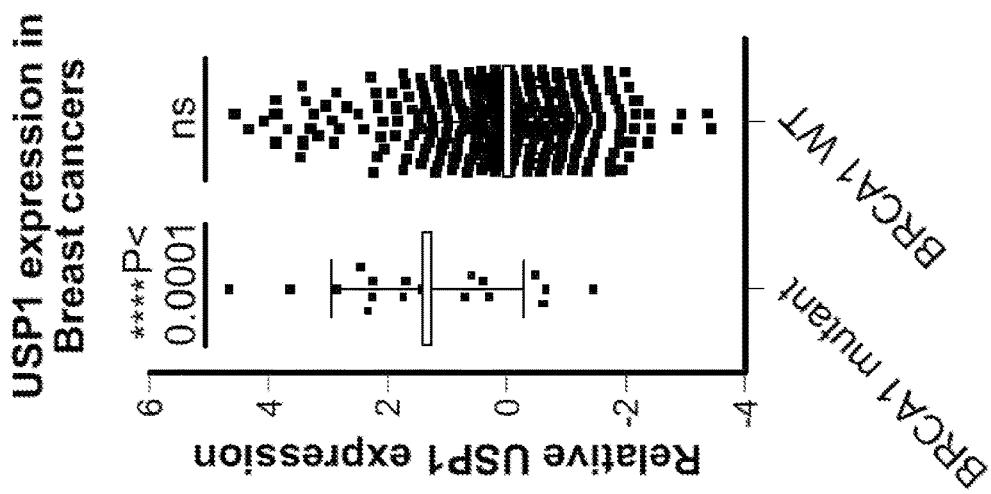
FIG. 1B. USP1 mRNA levels in BRCA1 mutated or BRCA1 wild type breast cancers were plotted using data from TCGA.

Homologous-recombination (HR) deficient tumors with BRCA1 and BRCA2 mutations frequently exhibit replication fork stability defects. To date, PARP inhibitors are the only targeted therapy available in the clinic against homologous-recombination (HR) deficient tumors. The present disclosure shows that a deubiquitinase, USP1, is significantly upregulated in tumors with mutations in BRCA1. siRNA mediated silencing or small molecule inhibition of USP1 resulted in fork destabilization and decreased viability of BRCA1 deficient cells. This disclosure further shows that USP1 independently binds to and is stimulated by fork DNA and is the first known deubiquitinase to be directly regulated by DNA binding. A truncated form of USP1, lacking its DNA binding region, was not stimulated by DNA and failed to localize and protect the replication fork. Persistence of monoubiquitinated PCNA at the replication fork was the mechanism of fork destabilization and cell death. Loss of monoubiquitinated PCNA, from RAD18 siRNA, rescued the sensitivity and replication fork instability induced by USP1 inhibition in BRCA1 deficient cells. USP1 therefore is the first deubiquitinating enzyme (DUB) exhibiting DNA-mediated activation at the replication fork, and is important in fork protection in BRCA1 deficient cells. Thus, the present disclosure shows that small molecule inhibitors against USP1 can be used as a therapeutic agent in BRCA1 and/or BRCA2 deficient cancers. Furthermore, many cancers can develop therapeutic resistance to PARP inhibitors and cross-linking agents. This disclosure also provides a new class of inhibitors that can mitigate therapeutic resistance to PARP inhibitors or cross-linking agents.

Ubiquitin Specific Protease 1 (USP1)

Protein ubiquitination is a critical post-translational modification that regulates multiple cellular processes. Protein ubiquitination is controlled by the coordinate activity of ubiquitin E3 ligases and deubiquitinating enzymes, referred to as deubiquitinating enzymes (DUBs) (16, 17). DUBs cleave the isopeptide bond between ubiquitin and the modified protein. Over one hundred DUB enzymes are known, and these proteins are subdivided into six subfamilies (18, 19). The USP (Ubiquitin Specific Protease) subfamily is the largest subfamily, with 58 members. USPs are cysteine proteases, containing a highly conserved catalytic domain.

The function and regulation of USP1, a member of the USP subclass of DUBs, has been evaluated in considerable detail. Like two closely-related DUBs, USP12 and USP46, USP1 binds to a conserved WD40-repeat protein, UAF1 (20, 21). Other USPs have WD40-repeat binding partners, suggesting a more general mechanism of USP activation (22). These three DUBs exist in a mostly inactive state, and their isopeptidase activity is stimulated by UAF1 binding.

UAF1 binds to a distinct site on USP12 or USP46 and, through an allosteric interaction, stimulates DUB activity (23, 24). The UAF1 binding site of USP1, USP12, and USP46 is the zinc finger region, at the tips of the DUB finger structure, distant (40 Å) from the catalytic triad of the protease (25). The crystal structure of USP1 has not been solved; however, it is a larger protein, suggesting that there may be additional regulatory regions in USP1 not present in USP12 or USP46. In addition, USP12 and USP46, but not USP1, are also activated independently by another WD40-repeat protein ($WDR_{20}$), through a different allosteric site (24).

USP1/UAF1 complex has a direct interaction with DNA. The known substrates of USP1/UAF1 include FANCD2-Ub, FANCI-Ub, and PCNA-Ub, all of which are DNA binding proteins. USP1/UAF1 travels with the replication fork during DNA synthesis, suggesting that it removes ubiquitin from protein substrates residing at the fork. Interestingly, the hydroxyurea-induced increase in FANCD2-Ub and PCNA-Ub at the fork correlates temporally with the release of USP1/UAF1 from the fork, suggesting that reduced local expression of USP1 accounts for the monoubiquitination of these substrates. In addition, UAF1 has been shown to have DNA binding activity and to directly interact with the HR-protein, RAD51AP1 (26, 28).

The present disclosure provides data showing that USP1 binds to DNA independently of UAF1, and is stimulated preferentially by DNA structures mimicking a replication fork. An internally-truncated version of USP1, which has active deubiquitinating activity, neither binds to DNA nor is stimulated by DNA. While wild-type USP1 localizes to replication forks of transfected human cells, mutant USP1-Trunc fails to localize to and stabilize the replication fork.

The present disclosure further shows that USP1 is required for stabilization of the replication fork of BRCA1 deficient cells, and knockout or small molecule inhibition with a specific inhibitor of the USP1/UAF1 complex is synthetic lethal in these cells.

USP1 and Replication Fork Stability

The replication fork is a structure that forms during DNA replication. It is created by helicases, which break the hydrogen bonds holding the two DNA strands together. The resulting structure has two branches, each one made up of a single strand of DNA. These two strands serve as the template for the leading and lagging strands, which will be created as DNA polymerase matches complementary nucleotides to the templates; the templates may be properly referred to as the leading strand template and the lagging strand template. BRCA1 and BRCA2 (BRCA1/2) proteins have a dual role in protecting genomic integrity. On the one hand, BRCA1/2 proteins promote homologous recombination (HR)-mediated DNA repair. On the other hand, these proteins also limit replication stress by controlling the stability of stalled replication forks (Kais et al. "FANCD2 maintains fork stability in BRCA1/2-deficient tumors and promotes alternative end-joining DNA repair." Cell reports 15.11 (2016): 2488-2499).

Figure 7:
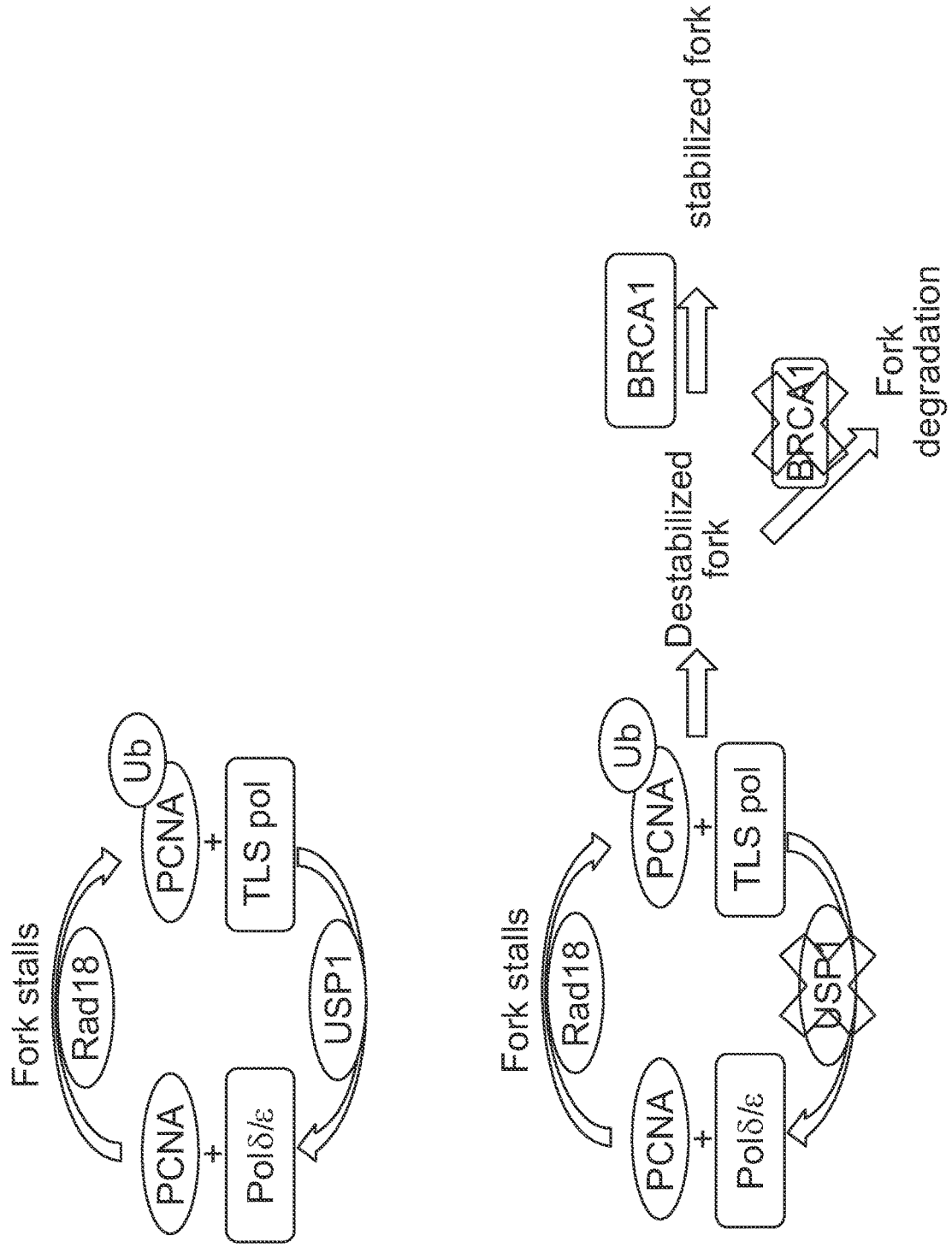
FIG. 7. Monoubiquitination of PCNA following replication fork stalling facilitates lesion bypass by TLS polymerases. USP1 deubiquitinates PCNA, facilitating the conversion of PCNA binding to replicative polymerases. Loss of USP1 lead to replication fork destabilization due to persistent TLS polymerase loading. BRCA1 is required to stabilize the replication fork.

The present disclosure shows that USP1 is required for stabilization of the replication fork of BRCA1/2 deficient cells (FIG. 7). The present disclosure also shows that a USP1 substrate—namely, PCNA—to be important in replication fork protection in BRCA1 deficient cells. Synthetic lethality between USP1 and BRCA1 was rescued by the silencing of PCNA ubiquitin ligase RAD18 and TLS polymerase POLK, which accumulates following USP1 silencing, due to the persistence of Ub-PCNA. The results suggest that accumulation of Translesion synthesis (TLS) polymerases lead to replication fork instability in BRCA1 deficient cells and provide a mechanism of synthetic lethality in BRCA1 deficient cells. In addition, the data in the present disclosure suggest a potential role of the BRCA1 protein in mitigating replication fork instability resulting from aberrant TLS.

The USP1 substrates, FANCD2-Ub and PCNA-Ub, regulate replication fork events. FANCD2 is monoubiquitinated by the FA core E3 ligase complex, and FANCD2-Ub recruits the nuclease, FAN1, to the fork. PCNA is monoubiquitinated by the UV-activated E3 ligase, RAD18, and PCNA-Ub recruits TLS polymerases, such as POLK, to the fork. Knockdown of USP1, in cell lines results in upregulation of FANCD2-Ub and PCNA-Ub and to DNA repair dysfunction.

The present disclosure demonstrates that the USP1/UAF1 complex is localized to the fork, and its deubiquitinating activity is stimulated by a DNA structure mimicking a fork. Localization of the active enzyme to the fork is required for fork stabilization and for reduction of FANCD2-Ub and PCNA-Ub levels at the fork. Interestingly, USP1/UAF1 is the first known DUB complex which is activated by DNA binding. DNA binding results in a reduction in km and an activation of kcat. Moreover, the strongest DUB activity results from binding DNA resembling a DNA replication fork. DUB enzymes are often bound in complexes with allosteric binding partners.

Thus, the present disclosure identifies an important mechanism by which USP1 stabilizes the fork. Knockdown or small molecule inhibition of USP1 results in the toxic accumulation of PCNA-Ub. Elevated PCNA-Ub results in elevated recruitment of the TLS polymerase POLK, to the fork, leading to fork destabilization and elevated single base pair mutagenesis. The cellular toxicity resulting from elevated PCNA-Ub levels can be reversed by the knockdown of the PCNA monoubiquitination ligase, Rad18.

BRCA1 Deficiency or BRCA2 Deficiency

BRCA1 and BRCA2 proteins are involved in both promoting homologous recombination (HR)-mediated DNA repair and also controlling the stability of stalled replication forks. Many tumor types, including, e.g., breast cancer, ovarian cancer, prostate cancer, pancreatic carcinomas, fallopian tube cancer, peritoneal cancer, acute myeloid leukemia, and uveal melanoma often have underlying defects in BRCA1 or BRCA2 activity. These defects are often due to germline or somatic mutations in the BRCA1 or BRCA2 genes. These tumors, with underlying defects in HR repair, are typically sensitive to PARP inhibitors. However, they can develop PARP inhibitor resistance over the time.

The present disclosure shows that USP1 inhibitor can have comparable cytotoxic activity in cancers with BRCA mutations. While normal cells can tolerate the loss of USP1 and the elevated expression of toxic PCNA-Ub at the fork, BRCA1-deficient tumor cells cannot tolerate these levels. Indeed, BRCA1-deficient cells already have unstable forks, and the further knockdown of USP1 results in a synthetic lethal interaction.

Thus, as used herein, the term "BRCA1 deficiency" refers to a subject that has one or more cells having abnormal BRCA1 levels or activities. Similarly, the term "BRCA2 deficiency" refers to a subject that has one or more cells having abnormal BRCA2 levels or activities. These abnormal activities interfere with the normal function of BRCA1 or BRCA2, and can cause a defect in HR-mediated DNA repair or decrease the stability of replication forks. Many methods are available to determine the abnormal BRCA1/2 levels or activities, e.g., RT-PCR, sequencing, western blot, functional assay, and/or determining the fractions of genomes in the cell etc.

BRCA1 promoter hypermethylation, BRCA2 promoter hypermethylation, BRCA1 mutations or BRCA2 mutations can all contribute to BRCA1 deficiency or BRCA2 deficiency. Many BRCA1 or BRCA2 mutations are known in the art. Some of these mutations are shown in Table 1 or Table 2.

TABLE 1

BRCA1 mutations

| Mutations | Other names | Comment |
|---|---|---|
| 185delAG i4000377 | also known as rs796856605 | risk allele deletion (D) |
| 5382insC i4000378 | also known as rs76171189 or rs80357906 | risk allele insertion (I) |
| rs28897696 | also known as A1708E | Predicted to be highly linked & causative |
| rs55770810 | also known as R1699W | Predicted to be linked & causative |
| rs1799950 | also known as Q356R | |
| rs4986850 | also known as D693N | |
| rs2227945 | also known as S1140G | |
| rs16942 | also known as K1183R | |
| rs1799966 | also known as S1613G | |
| rs41293463 | also known as M1775R | |
| rs1800709 | also known as R841W | |
| rs41293455 | also known as R1443G | |
| rs4986852 | also known as S1040N | |
| rs28897672 | also known as C61G | |

TABLE 2

BRCA2 mutations

| Mutations | Other names | Comment |
|---|---|---|
| 6174delT i4000379 | also known as rs80359550 | risk allele deletion |
| rs1799944 | also known as N991D | risk allele G |
| rs766173 | also known as N289H | risk allele G |
| rs144848 | also known as N372H or Asn372His | risk allele G |
| rs4987117 | also known as T1915M | risk allele T |
| rs1799954 | also known as R2034C | risk allele T |
| rs11571746 | also known as S2835P | risk allele C |
| rs11571747 | also known as E2856A | risk allele C |
| rs4987047 | also known as I2944F | risk allele T |
| rs11571833 | also known as K3326stop | risk allele T |

TABLE 2-continued

BRCA2 mutations

| Mutations | Other names | Comment |
|---|---|---|
| rs1801426 | also known as I3412V | risk allele G |
| rs28897756 | also known as P3039P or 9345G/A | risk allele A |

Various mutations in BRCA1 and BRCA2 are described, e.g., in US20030235819, US20080268435, US20150285801, U.S. Pat. Nos. 6,492,109, 7,993,835, WO/1999/028506; Nelson et al., "Genetic risk assessment and BRCA mutation testing for breast and ovarian cancer susceptibility: systematic evidence review for the US Preventive Services Task Force," Annals of internal medicine 143.5 (2005): 362-379; Mehrgou et al., "The importance of BRCA1 and BRCA2 genes mutations in breast cancer development," Medical journal of the Islamic Republic of Iran 30 (2016): 369; each of which is incorporated herein by reference in its entirety.

BRCA1 Deficient or BRCA2 Deficient Cancer

The present disclosure provides methods of treating a subject having, or at risk of developing, a cancer, wherein the subject is identified as having a BRCA1 and/or BRCA2 mutation. The present disclosure also provides methods of decreasing fork stability in a cell that has a BRCA1 and/or BRCA2 mutation, and methods of killing a cell that have BRCA1 and/or BRCA2 mutations. In some embodiments, the cell is a cancer cell.

As used herein, the term "cancer" refers to cells having the capacity for autonomous growth. Examples of such cells include cells having an abnormal state or condition characterized by rapidly proliferating cell growth. The term is meant to include cancerous growths, e.g., tumors; oncogenic processes, metastatic tissues, and malignantly transformed cells, tissues, or organs, irrespective of histopathologic type or stage of invasiveness. Also included are malignancies of the various organ systems, such as respiratory, cardiovascular, renal, reproductive, hematological, neurological, hepatic, gastrointestinal, and endocrine systems; as well as adenocarcinomas which include malignancies such as most colon cancers, renal-cell carcinoma, prostate cancer and/or testicular tumors, non-small cell carcinoma of the lung, and cancer of the small intestine. Cancer that is "naturally arising" includes any cancer that is not experimentally induced by implantation of cancer cells into a subject, and includes, for example, spontaneously arising cancer, cancer caused by exposure of a patient to a carcinogen(s), cancer resulting from insertion of a transgenic oncogene or knock-out of a tumor suppressor gene, and cancer caused by infections, e.g., viral infections. The term "carcinoma" is art recognized and refers to malignancies of epithelial or endocrine tissues. The term also includes carcinosarcomas, which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation. The term "hematopoietic neoplastic disorders" includes diseases involving hyperplastic/neoplastic cells of hematopoietic origin. A hematopoietic neoplastic disorder can arise from myeloid, lymphoid or erythroid lineages, or precursor cells thereof. In some embodiments, the cancer is breast cancer, ovarian cancer, prostate cancer, pancreatic carcinomas, fallopian tube cancer, peritoneal cancer, acute myeloid leukemia, or uveal melanoma. In some embodiments, the cancer is basal-like cancer, basal-like breast cancer, triple negative breast cancer, high grade cancer, or high grade serous ovarian cancer cell.

Thus, a cancer that is BRCA1 deficient or BRCA2 deficient refers to a cancer that has one or more cells having abnormal BRCA1 levels or activities, or abnormal BRCA2 levels or activities. These abnormal levels or activities interfere with the normal function of BRCA1 or BRCA2, and can cause a defect in HR-mediated DNA repair or decrease the stability of replication forks.

In some embodiments, the methods as described herein can be used to treat high grade tumors. Tumor grade is the description of a tumor based on how abnormal the tumor cells and the tumor tissue look under a microscope. It is an indicator of how quickly a tumor is likely to grow and spread. If the cells of the tumor and the organization of the tumor's tissue are close to those of normal cells and tissue, the tumor is called "well-differentiated." These tumors tend to grow and spread at a slower rate than tumors that are "undifferentiated" or "poorly differentiated," which have abnormal-looking cells and may lack normal tissue structures. The following system is generally used to describe the tumor grade.

GX: Grade cannot be assessed (undetermined grade)
G1: Well differentiated (low grade)
G2: Moderately differentiated (intermediate grade)
G3: Poorly differentiated (high grade)
G4: Undifferentiated (high grade)

Thus, the methods as described herein can be used to treat GX, G1, G2, G3, G4 tumors, particularly high grade tumors, e.g., G3 or G4 tumors.

Furthermore, because BRCA1 and BRCA2 play an important role in HR-mediated DNA repair, BRCA1 and/or BRCA2 deficient cancer are often sensitive to Poly(ADP-Ribose) Polymerase (PARP) inhibitors (e.g., Olaparib), cross-linking agents, and/or some other chemotherapeutic agents. PARP (e.g., Poly(ADP-ribose) polymerase 1 (PARP1)) is a key molecule in the repair of DNA single-strand breaks (SSBs). Inactivation of SSB repair by PARP1 inhibition during S-phase induces DNA double-strand breaks (DSBs) and may thus confer synthetic lethality to cells with defective homology-directed DSB repair. BRCA1 and BRCA2 function is critical for homologous recombination (HR), and BRCA-deficient cells appear to be highly sensitive to PARP inhibition, resulting in increased genomic instability, cell cycle arrest, and apoptosis. Thus, PARP inhibitors can be used to treat cancers, particularly, BRCA1 or BRCA2 deficient cancers. Many PARP inhibitors are known in the art. These PARP inhibitors include, e.g., Olaparib, ABT-888, AZD2281. These PARP inhibitors and some other PARP inhibitors are described, e.g., in Rottenberg, et al. "High sensitivity of BRCA1-deficient mammary tumors to the PARP inhibitor AZD2281 alone and in combination with platinum drugs." Proceedings of the National Academy of Sciences 105.44 (2008): 17079-17084; Tutt, et al. "Oral poly(ADP-ribose) polymerase inhibitor olaparib in patients with BRCA1 or BRCA2 mutations and advanced breast cancer: a proof-of-concept trial." The Lancet 376.9737 (2010): 235-244; U.S. Pat. Nos. 6,924,284; 9,150,628; US20090181951; US20140100239; US20080139568; WO/2006/067472A1; each of which is incorporated herein by reference in its entirety.

Similarly, BRCA1 and/or BRCA2 deficient cancers are also sensitive to cross-linking agents or some other chemotherapeutic agents. These agents often cause damages to DNA, requiring DNA repair. As used herein, the term "cross-linking agent" refers to an agent that can crosslink genomic DNA in a cell. The cross-linking agents often include, e.g., alkylating agents such as 1,3-bis(2-chloroethyl)-1-nitrosourea (BCNU, carmustine), nitrogen mustard, cisplatin, mitomycin, or busulfan, etc.

Although BRCA1 and/or BRCA2 deficient cancers are sensitive to PARP inhibitors, cross-linking agents, and/or some other chemotherapeutic agents, many of them eventually develop resistance to PARP inhibitors, cross-linking agents, or some other chemotherapeutic agents. This is known as acquired resistance. If the cancer is resistant to these agents even before being treated by these therapeutic agents (e.g., due to some random mutations before the treatment), the cancer is known as having intrinsic resistance to these agents. In some embodiments, the cancer is resistant to a PARP inhibitor. In some embodiments, the cancer is resistant to a cross-linking agent or a chemotherapeutic agent. In some embodiments, the cancer has intrinsic resistance or acquired resistance to PARP inhibitors. In some embodiments, the cancer has intrinsic resistance or acquired resistance to cross-linking agents or some other chemotherapeutic agents. In some embodiments, the cross-linking agent is cisplatin, mitomycin, or busulfan.

As Partner And Localizer of BRCA2 (PALB2) are also involved in homologous recombination, many BRCA1 and/or BRCA2 mutant cancer cells also have PALB2 deficiency. Thus, the methods as described herein can also be used treat cancers having PALB2 deficiency.

Methods of Treatment

The present disclosure provides methods of treating a subject (e.g., human) having, or at risk of developing, a cancer. The methods involve administering to the subject in need thereof an effective amount of a therapeutic agent (e.g., a USP1 inhibitor), wherein the subject is identified as having BRCA1 and/or BRCA2 mutation (e.g., mutation(s) that increase the risk of a cancer). In some embodiments, the therapeutic agent is a USP1 inhibitor. In some embodiments, the therapeutic agent is a UAF1 inhibitor.

In some embodiments, the therapeutic agent (e.g., a USP1 inhibitor) is administered as a monotherapy. As used herein, the term "monotherapy" means that only one therapy for the intended purpose (e.g., treating cancer) is administered to the subject during the treatment cycle. In a particular embodiment, the USP1 inhibitor is administered without a crosslinking agent. In some embodiments, other therapies, however, can be administered to the subject for other purposes. For example, anti-inflammatory agents or other agents that treat symptoms associated with cancer, but not the underlying cancer itself, including, e.g., inflammation, pain, weight loss, and general malaise can be administered to a subject with cancer during the period of monotherapy treatment.

In some embodiments, the methods involve administering to the subject in need thereof a therapy consisting of administration of a therapeutic agent (e.g., a USP1 inhibitor).

In some embodiments, the methods involve administering to the subject in need thereof an effective amount of an active agent consisting of a USP1 inhibitor. As used herein, the term "active agent" refers to an agent that is capable of performing a particular activity (e.g., treating cancer, inhibiting cancer, or killing cancer cells). As pharmaceutical carriers are usually not intended for the treatment purposes, pharmaceutical carriers are not active agents.

A subject being treated by the present methods can have completed any prior treatment (e.g., surgery, or being treated with some other anti-cancer agents) before the monotherapy treatment or receive additional therapies after the monotherapy treatment. In some embodiments, the subject will have completed any prior treatments at least 1 week (e.g., at least 2, 3, 4, 5, 6, 7, or 8 weeks) prior to treatment. In some embodiments, the subject is not treated with any additional therapies (e.g., other anti-cancer agents) for at least 1 week (e.g., at least 2, 3, 4, 5, 6, 7, or 8 weeks) following completion of the treatment cycle as described herein.

In some embodiments, the subject is not receiving any additional therapies (e.g., any anti-cancer agents, any therapeutic active agents) during the treatment cycle. In some embodiments, the subject is not receiving any additional any anti-cancer agents (e.g., chemotherapies). As used herein, the term "anti-cancer agent" refers to a therapeutic agent for treating cancers. In some embodiments, the subject is not receiving a PARP inhibitor or a cross-linking agent (e.g., cisplatin, mitomycin, or busulfan) during the treatment cycle.

As used herein, the terms "subject" and "patient" are used interchangeably throughout the specification and can describe an animal, human or non-human, to whom treatment according to the methods of the present disclosure is provided. Veterinary and non-veterinary applications are contemplated. Human patients can be adult humans or juvenile humans (e.g., humans below the age of 18 years old). In addition to humans, patients include but are not limited to mice, rats, hamsters, guinea-pigs, rabbits, ferrets, cats, dogs, and primates. Included are, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

As used in this context, to "treat" means to ameliorate at least one symptom of cancers or tumors. Often, the treatment results in ameliorating, stopping, stabilizing, reversing, inhibiting, slowing and/or delaying progression of a cancer in a subject. Thus, administration of a therapeutically effective amount of the agents as described herein can result in a decrease of tumor size or tumor volume, a decrease of tumor growth, a reduction of the increase rate of tumor volume in a subject (e.g., as compared to the rate of increase in tumor volume in the same subject prior to treatment or in another subject without such treatment), a decrease in the risk of developing a metastasis or the risk of developing one or more additional metastasis, an increase of survival rate, and/or an increase of life expectancy, etc. The tumor volume in a subject can be determined by various methods, e.g., as determined by direct measurement, MRI or CT.

In some embodiments, a USP1 inhibitor or a UAF1 inhibitor is administered to the subject. These inhibitors can be an antisense molecule, an miRNA, a shRNA, an antibody, or a small molecule. In some embodiments, the USP1 inhibitor is an antibody that specifically binds to USP1. In some embodiments, the UAF1 inhibitor is an antibody that specifically binds to UAF1.

The disclosure provides the antibodies that can specifically bind to the proteins as described herein. As used herein, when referring to an antibody, the phrases "specifically binding" and "specifically binds" mean that the antibody interacts with its target molecule preferably to other molecules, because the interaction is dependent upon the presence of a particular structure (i.e., the antigenic determinant or epitope) on the target molecule; in other words, the reagent is recognizing and binding to molecules that include a specific structure rather than to all molecules in general. An antibody that specifically binds to the target molecule may be referred to as a target-specific antibody. For example, an antibody that specifically binds to a USP1 molecule may be referred to as a USP1-specific antibody or an anti-USP1 antibody.

The disclosure also provides methods of decreasing fork stability in a cell in vivo or in vitro that is BRCA1 deficient or BRCA2 deficient, and methods of killing a cell in vivo or in vitro that is BRCA1 deficient or BRCA2 deficient. In some embodiments, the methods involve contacting the cell with an effective amount of a USP1 inhibitor.

The cell can be a cancer cell, e.g., a basal-like cancer cell, a basal-like breast cancer cell, a triple negative breast cancer cell, a high grade cancer cell, or a high grade serous ovarian cancer cell, etc. These cells can be cultured cells or cells in a subject (e.g., in a human subject). In some embodiments, the cells can have an increased activity or expression of USP1 and/or Rad18. Furthermore, because BRCA1 and BRCA2 are involved in homologous recombination, a defect in homologous recombination indicates the defect of BRCA1 and/or BRCA2. Thus, the present disclosure also provides methods of decreasing fork stability in a cell or killing a cell, wherein the cell has a defect in homologous recombination (e.g., related to BRCA1 or BRCA2 defects).

In one aspect, the present disclosure provides methods of inhibiting the growth of a tumor. The methods include the steps of contacting the tumor with an effective amount of a USP1 inhibitor or a UAF1 inhibitor.

USP1 Inhibitors

The present disclosure shows that USP1 inhibitors have cytotoxic activity in BRCA mutant cancers. Numerous USP1 inhibitors are known in the art. These USP1 inhibitors can be antisense molecules, miRNA, shRNA, antibodies, or small molecules. In some embodiments, the USP1 inhibitor is an antisense molecule, a miRNA, or a shRNA. In some embodiments, the USP1 inhibitor is a small molecule.

As used herein, the term "small molecule" refers to small organic or inorganic molecules of molecular weight below about 3,000 Daltons. In general, small molecules useful for the purpose have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

In some embodiments, the USP1 inhibitor can be a compound having the structure of Formula I, or a pharmaceutically acceptable salt thereof.

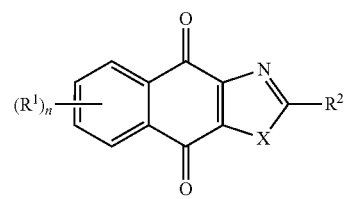

(Formula I)

wherein

X is O, S, or NR$^3$;

n is 0, 1, 2, 3, or 4;

each occurrence of R$^1$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^A$; —C(=O)$R^A$; —C(=O)N($R^A$)$_2$; $CO_2R^A$; —CN; —SCN; —$SR^A$; —$SOR^A$; —$SO_2R^A$; —$NO_2$; —$N_3$; —N($R^A$)$_2$; —NHC(=O)$R^A$; $NR^AC$(=O)N($R^A$)$_2$; —OC(=O)$OR^A$; —OC(=O)$R^A$; —OC(=O)N($R^A$)$_2$; —$NR^A$C(=O)$OR^A$; or —C($R^A$)$_3$; wherein each occurrence of $R^A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R^2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^B$; —C(=O)$R^B$; —C(=O)N($R^B$)$_2$; —$CO_2R^B$; —CN; —SCN; —$SR^B$; —$SOR^B$; —$SO_2R^B$; —$NO_2$; —$N_3$; —N($R^B$)$_2$; —NHC(=O)$R^B$; —$NR^B$C(=O)N($R^B$)$_2$; —OC(=O)$OR^B$; —OC(=O)$R^B$; —OC(=O)N($R^B$)$_2$; —$NR^B$C(=O)$OR^B$; or —C($R^B$)$_3$; wherein each occurrence of $R^B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R^3$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety. A detailed description regarding these USP1 inhibitors are described, e.g., in U.S. Pat. No. 9,518,032, which is incorporated herein by reference in its entirety.

In some embodiments, the USP1 inhibitor is a compound having the structure of Formula II (C527), or a pharmaceutically acceptable salt thereof.

(Formula II)

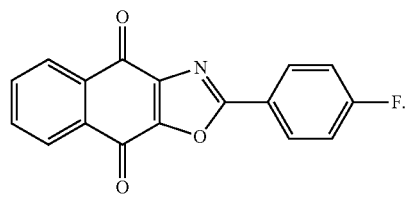

In some embodiments, the USP1 inhibitor can be a compound having the structure of Formula III, or a pharmaceutically acceptable salt thereof.

(Formula III)

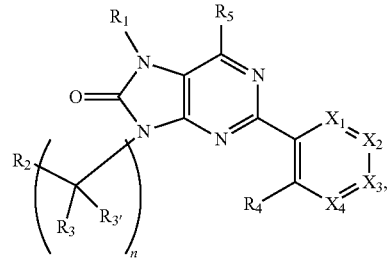

wherein:
$X_1$ is $CR_6$ or N;
$X_2$ is $CR_7$ or N;
$X_3$ is $CR_8$ or N;
$X_4$ is $CR_9$ or N;
$R^1$ is H, —$CD_3$, ($C_1$-$C_6$) alkyl, ($C_2$-$C_6$) alkenyl, ($C_2$-$C_6$) alkynyl, ($C_1$-$C_6$) haloalkyl, ($C_2$-$C_6$) hydroxyalkyl, ($C_3$-$C_8$) cycloalkyl, or heterocycloalkyl, wherein the alkyl, alkenyl, alkynyl, cycloalkyl, and heterocycloalkyl are optionally substituted with one or more substituents selected from halogen, —$OR_{20}$, —C(O)$R_{20}$, —$CO_2R_{20}$, —$NR_{18}R_{19}$, —$NR_{20}$C(O)$R_{21}$, —C(O)$NR_{20}R_{21}$, —$NR_{20}$C(O)$NR_{21}R_{22}$, —$NR_{20}$S(O)$_rR_{21}$, —S(O)$_rNR_{20}R_{21}$, —$NR_{20}$S(O)$_rNR_{21}R_{22}$, —S(O)$_rR_{20}$, —P(O)$R_{20}R_{21}$, oxo, and —Si(($C_1$-$C_4$) alkyl)$_3$;
$R_2$ is ($C_6$-$C_{14}$) aryl, heteroaryl, ($C_3$-$C_{10}$) cycloalkyl, or heterocycloalkyl, wherein the aryl, heteroaryl, cycloalkyl, and heterocycloalkyl are substituted with one or more $R_{10}$;
$R_3$ is H, D, ($C_1$-$C_6$) alkyl, ($C_1$-$C_6$) haloalkyl, ($C_1$-$C_6$) hydroxyalkyl, ($C_1$-$C_6$) aminoalkyl, heterocycloalkyl, halogen —C(O)OH, —C(O)$NH_2$, or CN;
$R_{3'}$ is H, ($C_1$-$C_6$) alkyl, ($C_1$-$C_6$) haloalkyl, ($C_1$-$C_6$) hydroxyalkyl, ($C_1$-$C_6$) aminoalkyl, heterocycloalkyl, —C(O)OH, —C(O)$NH_2$, or CN; or
$R_3$ and $R_{3'}$ together with the carbon atom to which they are attached may form a ($C_3$-$C_7$) cycloalkyl ring; $R_3$ and $R_{3'}$ together with the carbon atom to which they are attached may form a heterocycloalkyl ring;
$R_4$ is ($C_1$-$C_6$) alkyl, ($C_2$-$C_6$) alkenyl, ($C_2$-$C_6$) alkynyl, ($C_1$-$C_6$) alkoxy, ($C_1$-$C_6$) haloalkyl, ($C_1$-$C_6$) haloalkoxy, ($C_3$-$C_8$) cycloalkyl, —O—($C_0$-$C_2$)-alkylene-($C_3$-$C_8$) cycloalkyl, heterocycloalkyl, —O—($C_0$-$C_2$)-alkylene-heterocycloalkyl, halogen, —OH, —$NH_2$, CN, —C(O)($C_1$-$C_4$) alkyl, —C(O)O($C_1$-$C_4$) alkyl, —$NR_{20}$C(O)O($C_1$-$C_4$) alkyl, —Si($CH_3$)$_3$, —$SF_5$, —S(O)$_p$($C_1$-$C_4$) alkyl, —S(O)$_p$(NH)($C_1$-$C_4$) alkyl, —NH($C_1$-$C_4$) alkyl, —N(($C_1$-$C_4$) alkyl)$_2$, NH—($C_0$-$C_2$)-alkylene-($C_3$-$C_8$) cycloalkyl, or —NH—($C_0$-$C_2$)-alkylene-heterocycloalkyl, wherein the alkyl, alkenyl, alkynyl, and alkoxy are optionally substituted with one or more substituents selected from ($C_1$-$C_6$) alkyl, ($C_1$-$C_6$) alkoxy, ($C_3$-$C_8$) cycloalkyl, halogen, —OH, —S(O)$_r$($C_1$-$C_4$) alkyl, —S(O)$_r$(NH)($C_1$-$C_4$) alkyl, —$SF_5$, —Si($CH_3$)$_3$, —$NH_2$, —NH($C_1$-$C_4$) alkyl, —N(($C_1$-$C_4$) alkyl)$_2$, —C(O)$NH_2$, —C(O)NH($C_1$-$C_4$) alkyl, and —C(O)N(($C_1$-$C_4$) alkyl)$_2$; and the cycloalkyl, heterocycloalkyl, aryl and heteroaryl are optionally substituted with one or more substituents selected from ($C_1$-$C_6$) alkyl, ($C_1$-$C_6$) haloalkyl, and halogen; or
$R_4$ and $X_4$ together with the atoms to which they are attached may form a ($C_6$-$C_{14}$) aryl ring optionally substituted with one or more $R_{17}$; or $R_4$ and $X_4$ on adjacent atoms together with the atoms to which they are attached may form a heteroaryl ring optionally substituted with one or more $R_{17}$; or $R_4$ and $X_4$ together with the atoms to which they are attached may form a $(C_5-C_7)$ cycloalkyl ring optionally substituted with one or more $R_{17}$; or $R_4$ and $X_4$ on adjacent atoms together with the atoms to which they are attached may form a heterocycloalkyl ring optionally substituted with one or more $R_{17}$;

$R_5$ is H, D, $(C_1-C_6)$ alkyl, $(C_2-C_6)$ alkenyl, $(C_2-C_6)$ alkynyl, $(C_1-C_6)$ alkoxy, $(C_1-C_6)$ hydroxyalkyl, $(C_1-C_6)$ haloalkoxy, halogen, $(C_3-C_6)$ cycloalkyl, heterocycloalkyl, $C(O)O(C_1-C_4)$ alkyl, —$C(O)(C_1-C_4)$ alkyl, —$C(O)NR_{13}R_{14}$, —OH, —$NH_2$, CN, —$NH(C_1-C_4)$ alkyl, —$N((C_1-C_4)$ alkyl$)_2$ or —$NR_{13}C(O)R_{14}$; or $R_1$ and $R_5$ together with the atoms to which they are attached form a heterocycloalkyl ring;

each $R_6$, $R_7$, $R_8$, and $R_9$ is independently, at each occurrence, H, D, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, $(C_1-C_6)$ hydroxyalkyl, $(C_3-C_8)$ cycloalkyl ring, heterocycloalkyl, or halogen, wherein the alkyl is optionally substituted with one or more $(C_1-C_6)$ alkoxy;

each $R_{10}$ is independently at each occurrence D, —$CD_3$, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, $(C_1-C_6)$ hydroxyalkyl, halogen, —$C(O)R_{14}$, —$C(O)OR_{13}$, —$NR_{13}R_{14}$, —$NR_{13}C(O)R_{14}$, $NR_{13}C(O)NR_{13}R_{14}$, —$C(O)NR_{13}R_{14}$, —$S(O)_pR_{14}$, —$NR_{13}S(O)_pR_{14}$, —$S(O)_pNR_{13}R_{14}$, —CN, —$(C_0-C_2)$-alkylene-$(C_6-C_{14})$ aryl, —$(C_0-C_2)$-alkylene-heteroaryl, —$(C_0-C_2)$-alkylene-$(C_3-C_8)$ cycloalkyl, —$(C_0-C_2)$-alkylene-heterocycloalkyl, —O—$(C_0-C_2)$-alkylene-aryl, —O—$(C_0-C_2)$-alkylene-heteroaryl, —O—$(C_0-C_2)$-alkylene-$(C_3-C_8)$ cycloalkyl, or —O—$(C_0-C_2)$-alkylene-heterocycloalkyl, wherein the aryl, heteroaryl, cycloalkyl and heterocycloalkyl are optionally substituted with one or more $R_{11}$ and the alkyl, alkenyl, alkynyl, and alkoxy are optionally substituted with one or more $R_{12}$; or two $R_{10}$ on adjacent atoms together with the atoms to which they are attached may form a $(C_6-C_{14})$ aryl ring optionally substituted with one or more $R_{11}$; or two $R_{10}$ on adjacent atoms together with the atoms to which they are attached may form a heteroaryl ring optionally substituted with one or more $R_{11}$; or two $R_{10}$ on adjacent atoms together with the atoms to which they are attached may form a $(C_3-C_8)$ cycloalkyl ring optionally substituted with one or more $R_{11}$; or two $R_{10}$ on adjacent atoms together with the atoms to which they are attached may form a heterocycloalkyl ring optionally substituted with one or more $R_{11}$; or two $R_{10}$ on the same atom to which they are attached may form a spirocycloalkyl ring optionally substituted with one or more $R_{11}$; or two $R_{10}$ on the same atom to which they are attached may form a spiroheterocycloalkyl ring optionally substituted with one or more $R_{11}$;

each $R_{11}$ is independently at each occurrence D, —$CD_3$, $(C_1-C_6)$ alkyl, $(C_1-C_6)$ alkoxy, $(C_1-C_6)$ haloalkyl, $(C_1-C_6)$ haloalkoxy, halogen, CN, —OH, —$NH_2$, —NH$(C_1-C_4)$ alkyl, —$N((C_1-C_4)$ alkyl$)_2$, —$C(O)O(C_1-C_4)$ alkyl, —$S(O)_q(C_1-C_4)$ alkyl, —$C(O)NH_2$, —$C(O)NH(C_1-C_4)$ alkyl, —$C(O)N((C_1-C_4)$ alkyl$)_2$, —NHC(O)$(C_1-C_4)$ alkyl, —$N((C_1-C_4)$ alkyl)C(O)$(C_1-C_4)$ alkyl, $(C_6-C_{14})$ aryl, heteroaryl, $(C_3-C_8)$ cycloalkyl, or heterocycloalkyl, wherein the alkyl, alkoxy, $(C_3-C_8)$ cycloalkyl, heterocycloalkyl, aryl, and heteroaryl are optionally substituted with one or more substituents selected from $(C_1-C_6)$ alkyl, $(C_1-C_6)$ alkoxy, $(C_1-C_6)$ haloalkyl, C(O)OH, —$C(O)O(C_1-C_4)$ alkyl, —C(O)$(C_1-C_4)$ alkyl, —$S(O)_q(C_1-C_4)$ alkyl, —$C(O)NH(C_1-C_4)$ alkyl, —$C(O)N((C_1-C_4)$ alkyl$)_2$, —OH, —$NH_2$, —CN, —NH$(C_1-C_4)$ alkyl, and —$N((C_1-C_4)$ alkyl$)_2$; or two $R_{11}$ on adjacent atoms together with the atoms to which they are attached may form a heterocycloalkyl ring; or two $R_{11}$ on adjacent atoms together with the atoms to which they are attached may form a $(C_5-C_5)$ cycloalkyl ring; or two $R_1$ on adjacent atoms together with the atoms to which they are attached may form a $(C_6-C_{14})$ aryl ring; or two $R_1$ on adjacent atoms together with the atoms to which they are attached may form a heteroaryl ring; or two $R_{11}$ together with the atom to which they are attached may form a C=O;

each $R_{12}$ is independently at each occurrence $(C_1-C_6)$ alkoxy, —$NR_{15}R_{16}$, —$NR_{15}C(O)NR_{15}R_{16}$, —$NR_{15}C(O)R_{16}$, —$NR_{15}S(O)_mR_{16}$, or —$C(O)NH(C_3-C_8)$ cycloalkyl; each $R_{13}$ is independently at each occurrence H or $(C_1-C_4)$ alkyl;

each $R_{14}$ is independently at each occurrence H, $(C_1-C_6)$ alkyl, $(C_2-C_6)$ alkenyl, $(C_2-C_6)$ alkynyl, $(C_1-C_6)$ haloalkyl, —$(C_0-C_2)$-alkylene-$(C_3-C_8)$ cycloalkyl, —$(C_0-C_2)$-alkylene-heterocycloalkyl, —$(C_0-C_2)$-alkylene-$(C_6-C_{14})$ aryl, or —$(C_0-C_2)$-alkylene-heteroaryl, wherein the alkyl, cycloalkyl, heterocycloalkyl, aryl, and heteroaryl is optionally substituted with one or more substituents selected from $(C_1-C_4)$ alkyl optionally substituted with $(C_1-C_4)$ alkoxy, $(C_1-C_4)$ alkoxy, $(C_1-C_4)$ haloalkyl, $(C_1-C_4)$ haloalkoxy, $(C_6-C_{14})$ aryl, heteroaryl, halogen, —OH, —$NH_2$, CN, —$C(O)NH_2$, —$C(O)NH(C_1-C_4)$ alkyl, —$C(O)N((C_1-C_4)$ alkyl$)_2$, —NH$(C_1-C_4)$ alkyl, and —$N((C_1-C_4)$ alkyl$)_2$; or $R_{13}$ and $R_{14}$ together with the nitrogen atom to which they are attached may form a heterocycloalkyl ring optionally substituted with one or more $R_{23}$;

each $R_{15}$ is independently at each occurrence H or $(C_1-C_4)$ alkyl;

each $R_{16}$ is independently at each occurrence H, $(C_1-C_6)$ alkyl, $(C_2-C_6)$ alkenyl, $(C_2-C_6)$ alkynyl, $(C_2-C_6)$ haloalkyl, $(C_3-C_8)$ cycloalkyl, or —$(C_0-C_2)$-alkylene-heteroaryl, wherein the alkyl, alkenyl, alkynyl, cycloalkyl, and heteroaryl are optionally substituted with one or more substituents independently selected from $(C_1-C_4)$ alkyl, $(C_1-C_4)$ alkoxy, $(C_1-C_4)$ haloalkyl, $(C_1-C_4)$ haloalkoxy, and halogen;

each $R_{17}$ is independently at each occurrence $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, $(C_1-C_6)$ hydroxyalkyl, halogen, —OH, —$NH_2$, or CN;

each $R_{18}$ and $R_{19}$ is independently at each occurrence H or $(C_1-C_4)$ alkyl; or $R_{18}$ and $R_{19}$ together with the nitrogen atom to which they are attached may form a heterocycloalkyl ring;

each $R_{20}$, $R_{21}$ and $R_{22}$ is independently at each occurrence H, $(C_1-C_4)$ alkyl, or $(C_6-C_{14})$ aryl;

each $R_{23}$ is independently selected from $(C_1-C_4)$ alkyl, $(C_1-C_4)$ alkoxy, $(C_1-C_4)$ haloalkoxy, halogen, —C(O) $(C_1-C_4)$ alkyl, —$C(O)O(C_1-C_4)$ alkyl, —$C(O)(C_3-C_8)$ cycloalkyl, C(O)heterocycloalkyl, —OH, —$NH_2$, and CN, wherein the alkyl and alkoxy are optionally substituted with one or more substituents selected from $(C_1-C_4)$ alkoxy and —OH; or two R₂₃ on the same atom to which they are attached may form a spiroheterocycloalkyl ring; and each m, n, p, q, and r is independently 0, 1, or 2.

A detailed description regarding these USP1 inhibitors can be found, e.g., in US 20170145012, which is incorporated herein by reference in its entirety.

In some embodiments, the USP1 inhibitor is 9-(4-(3,5-dimethyl-1H-pyrazol-1-yl)benzyl)-2-(2-isopropylphenyl)-7,9-dihydro-8H-purin-8-one; or 2-(2-isopropylpyridin-3-yl)-9-(4-(1-methyl-4-(trifluoromethyl)-1H-imidazol-2-yl)benzyl)-7,9-dihydro-8H-purin-8-one.

In some embodiments, the USP1 inhibitor is ML323.

(Formula IV)

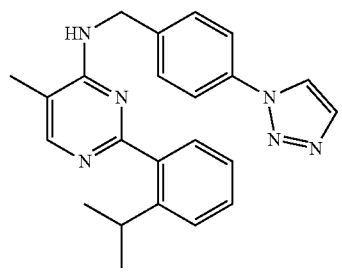

In some embodiments, the USP1 inhibitor is pimozide.

(Formula V)

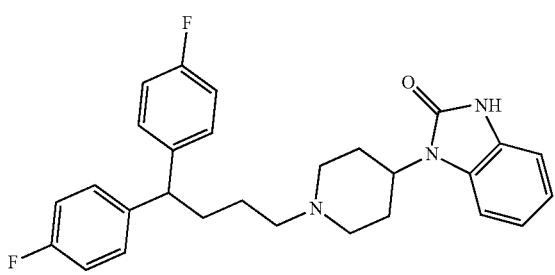

In some embodiments, the USP1 inhibitor is SJB2-043.

(Formula VI)

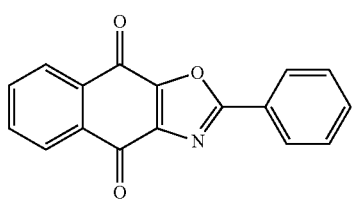

In some embodiments, the USP1 inhibitor is SJB019 or SJB3-019A. The USP1 inhibitor SJB3-019A has the structure as shown below.

(Formula VII)

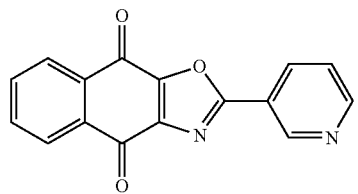

In some embodiments, the USP1 inhibitor is a USP1 inhibitor know in the art. Numerous USP1 inhibitors are known in the art, and are described, see e.g., in U.S. Pat. No. 9,518,032, US 20170145012, US20100330599, U.S. Pat. Nos. 7,754,463, 8,541,192, US20170145012, WO/2007/149484, WO/2017/087837, Liang et al., "A selective USP1-UAF1 inhibitor links deubiquitination to DNA damage responses," Nature chemical biology 10.4 (2014): 298-304; Mistry et al., "Small-molecule inhibitors of USP1 target ID1 degradation in leukemic cells," Molecular cancer therapeutics 12.12 (2013): 2651-2662; each of which is incorporated herein by reference in its entirety.

Inhibitory Nucleic Acids

The present disclosure provides inhibitory nucleic acids for any genes, and/or the RNA product of these genes as described in the present disclosure. For example, the present disclosure provides inhibitory nucleic acids for USP1 (NM_001017416.1→NP_001017416.1) (e.g., SEQ ID NOs: 1-3), and UAF1 (also known as WD Repeat Domain 48, or WDR48; NM_001303402.1→NP_001290331.1) etc. These inhibitory nucleic acids can be used in various methods as described herein, e.g., treating a subject having, or at risk of developing, a cancer (e.g., BRCA1 or BRCA2 deficient cancer), or killing a cancer cell (e.g., BRCA1 or BRCA2 deficient cancer cells).

These inhibitory nucleic acids useful in the present methods and compositions include, e.g., antisense oligonucleotides, ribozymes, external guide sequence (EGS) oligonucleotides, siRNA compounds, single- or double-stranded RNA interference (RNAi) compounds such as siRNA compounds, modified bases/locked nucleic acids (LNAs), peptide nucleic acids (PNAs), and other oligomeric compounds or oligonucleotide mimetics which hybridize to at least a portion of the target nucleic acid and modulate its function. In some embodiments, the inhibitory nucleic acids include antisense molecules, antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof.

In some embodiments, the inhibitory nucleic acids are 10 to 50, 10 to 20, 10 to 25, 13 to 50, or 13 to 30 nucleotides in length. One having ordinary skill in the art will appreciate that this embodies inhibitory nucleic acids having complementary portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the inhibitory nucleic acids are 15 nucleotides in length. In some embodiments, the inhibitory nucleic acids are 12 or 13 to 20, 25, or 30 nucleotides in length. One having ordinary skill in the art will appreciate that this embodies inhibitory nucleic acids having complementary portions of 12, 13, 14, 15, 16, 17, 18, 19, 20, 21, 22, 23, 24, 25, 26, 27, 28, 29 or 30 nucleotides in length, or any range therewithin (complementary portions refer to those portions of the inhibitory nucleic acids that are complementary to the target sequence).

The inhibitory nucleic acids useful in the present methods are sufficiently complementary to the target RNA, i.e., hybridize sufficiently well and with sufficient specificity, to give the desired effect. "Complementary" refers to the capacity for pairing, through hydrogen bonding, between two sequences comprising naturally or non-naturally occurring bases or analogs thereof. For example, if a base at one position of an inhibitory nucleic acid is capable of hydrogen bonding with a base at the corresponding position of a RNA, then the bases are considered to be complementary to each other at that position. 100% complementarity is not required.

In some embodiments, the inhibitory nucleic acid molecules can be designed to target a specific region of the RNA sequence. For example, a specific functional region can be targeted, e.g., a region comprising a known RNA localization motif (i.e., a region complementary to the target nucleic acid on which the RNA acts). Alternatively, or in addition, highly conserved regions can be targeted, e.g., regions identified by aligning sequences from disparate species such as primate (e.g., human) and rodent (e.g., mouse) and looking for regions with high degrees of identity. Percent identity can be determined routinely using basic local alignment search tools (BLAST programs) (Altschul et al., J. Mol. Biol., 1990, 215, 403-410; Zhang and Madden, Genome Res., 1997, 7, 649-656), e.g., using the default parameters.

For further disclosure regarding inhibitory nucleic acids, please see US2010/0317718 (antisense oligos); US2010/0249052 (double-stranded ribonucleic acid (dsRNA)); US2009/0181914 and US2010/0234451 (LNAs); US2007/0191294 (siRNA analogues); US2008/0249039 (modified siRNA); and WO2010/129746 and WO2010/040112 (inhibitory nucleic acids); each of which is incorporated herein by reference in its entirety.

Antisense

In some embodiments, the inhibitory nucleic acids are antisense molecules or antisense oligonucleotides. Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under stringent conditions to an RNA. Thus, oligonucleotides are chosen that are sufficiently complementary to the target, i.e., that hybridize sufficiently well and with sufficient specificity, to give the desired effect.

siRNA/shRNA

In some embodiments, the nucleic acid sequence that is complementary to an RNA as described herein can be an interfering RNA, including but not limited to a small interfering RNA ("siRNA") or a small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

In some embodiments, the interfering RNA coding region encodes a self-complementary RNA molecule having a sense region, an antisense region and a loop region. Such an RNA molecule when expressed desirably forms a "hairpin" structure, and is referred to herein as an "shRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. For details, see Brummelkamp et al., Science 296:550-553, (2002); Lee et al, Nature Biotechnol., 20, 500-505, (2002); Miyagishi and Taira, Nature Biotechnol 20:497-500, (2002); Paddison et al. Genes & Dev. 16:948-958, (2002); Paul, Nature Biotechnol, 20, 505-508, (2002); Sui, Proc. Natl. Acad. Sd. USA, 99(6), 5515-5520, (2002); Yu et al. Proc NatlAcadSci USA 99:6047-6052, (2002).

The target RNA cleavage reaction guided by siRNAs is highly sequence specific. In general, siRNA containing a nucleotide sequences identical to a portion of the target nucleic acid are preferred for inhibition. However, 100% sequence identity between the siRNA and the target gene is not required. Thus, the methods as described herein have the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In general, the siRNAs must retain specificity for their target, i.e., must not directly bind to, or directly significantly affect expression levels of, transcripts other than the intended target.

Making and Using Inhibitory Nucleic Acids

The nucleic acid sequences used to practice the methods described herein, whether RNA, cDNA, genomic DNA, vectors, viruses or hybrids thereof, can be isolated from a variety of sources, genetically engineered, amplified, and/or expressed/generated recombinantly. Recombinant nucleic acid sequences can be individually isolated or cloned and tested for a desired activity. Any recombinant expression system can be used, including e.g. in vitro, bacterial, fungal, mammalian, yeast, insect or plant cell expression systems.

Nucleic acid sequences can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989)), Coffin et al. (Retroviruses. (1997)) and "RNA Viruses: A Practical Approach" (Alan J. Cann, Ed., Oxford University Press, (2000)). As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids can be constructed based on viral backbones including, but not limited to, a retrovirus, lentivirus, adenovirus, adeno-associated virus, pox virus or alphavirus. The recombinant vectors capable of expressing the nucleic acids of the invention can be delivered as described herein, and persist in target cells (e.g., stable transformants).

Nucleic acid sequences used to practice this invention can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Nucleic acid sequences of the invention can be stabilized against nucleolytic degradation such as by the incorporation of a modification, e.g., a nucleotide modification. For example, nucleic acid sequences of the invention include a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O-N-methylacetamido (2'-O-NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom (see, e.g., Kaupinnen et al., Drug Disc. Today 2(3):287-290 (2005); Koshkin et al., J. Am. Chem. Soc., 120(50):13252-13253 (1998)). For additional modifications see US 20100004320, US 20090298916, and US 20090143326.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook et al., Molecular Cloning; A Laboratory Manual 3d ed. (2001); Current Protocols in Molecular Biology, Ausubel et al., eds. (John Wiley & Sons, Inc., New York 2010); Kriegler, Gene Transfer and Expression: A Laboratory Manual (1990); Laboratory Techniques In Biochemistry And Molecular Biology: Hybridization With Nucleic Acid Probes, Part I. Theory and Nucleic Acid Preparation, Tijssen, ed. Elsevier, N.Y. (1993).

Methods of Determining BRCA1 Deficiency or BRCA2 Deficiency

The present disclosure also provides methods of determining that a subject has BRCA1 deficiency or BRCA2 deficiency. The methods involve obtaining a tissue sample from the subject; and determining whether one or more cells in the tissue sample has BRCA1 deficiency or BRCA2 deficiency.

The abnormal levels or activities of BRCA1 and/or BRCA2 can be determined by many methods known in the art. As described above, many cells with BRCA1 deficiency or BRCA2 deficiency have BRCA1 or BRCA2 mutations. These mutations can be determined by, e.g., PCR or sequencing. The abnormal levels of BRCA1 and/or BRCA2 can also be determined by various assays, e.g., western blot, and RT-PCR. Furthermore, the abnormal levels or activities of BRCA1 and/or BRCA2 can be determined by various functional assays, e.g., assays designed to determine the function of HR-mediated DNA repair, iPOND (Isolation of protein on nascent DNA), etc. The methylation status of BRCA1 or BRCA2 promoters can be determined by methods known in the art as well, for example, bisulfite-converted DNA can be used for the amplification followed by sequencing.

Furthermore, the abnormal levels or activities of BRCA1 and/or BRCA2 can be determined by contacting the cell with an effective amount of a USP1 inhibitor; determining that the USP1 inhibitor induces cell death or increases fork instability, thereby determining whether the cell is BRCA1 deficient or BRCA2 deficient.

In addition, there are many mutations in the BRCA1 gene and BRCA2 gene. Not all of them necessarily are functional mutations. The present disclosure also provides methods of determining whether a mutation in BRCA1 or BRCA2 is a functional mutation, or whether a cell has functional defects in BRCA1 or BRCA2. In some embodiments, the methods involve, e.g., contacting the cell with an effective amount of a USP1 inhibitor; and determining that the USP1 inhibitor induces cell death or increases fork instability.

Combination Therapy

The methods or compositions as described herein can also be used in combination with some other therapies, e.g., surgeries, radiation therapies (e.g., ultraviolet light), chemotherapies, and/or immunotherapies. The USP1 inhibitor and the other therapy (e.g., UAF1 inhibitor) may be administered before, after, or at substantially the same time as one another.

In some embodiments, the methods involve administrating to the subject an effective amount of USP1 inhibitor; and an agent that can increase the expression or activity of RING-Type E3 Ubiquitin Transferase RAD18 (Rad18) (NM_020165.3→NP_064550.3), an agent that can increase the expression or activity of Proliferating Cell Nuclear Antigen (PCNA) (NM_002592.2→NP_002583.1), and/or an agent that can increase the expression or activity of POLK (DNA polymerase kappa; NM 001345921.1→NP 001332850.1). Thus, in some embodiments, the methods involve administering the subject in need thereof a therapy consisting of administering a USP1 inhibitor and an agent that can increase the expression or activity Rad18. In some embodiments, the methods involve administering the subject in need thereof a therapy consisting of administering a USP1 inhibitor and an agent that can increase the expression or activity PCNA. In some embodiments, the methods involve administering the subject in need thereof a therapy consisting of administering a USP1 inhibitor and an agent that can increase the expression or activity POLK. In some embodiments, the agent is a vector comprising a nucleic acid encoding Rad18, PCNA, or both.

In some embodiments, the immunotherapy involves administering an effective amount of an immune checkpoint inhibitor (e.g., anti-PD-1 antibody, anti-PD-L1 antibody, or anti-CTLA-4 antibody) to the subject.

In some embodiments, the methods described herein can be used alone or in combination with some other methods known in the art, including, e.g., treating the subject with chemotherapy. Alternatively or in addition, the methods can include performing surgery on the subject to remove at least a portion of the cancer, e.g., to remove a portion of or all of a tumor(s), from the patient.

The methods can also include the step of administering to the subject one or more chemotherapeutic agents, one or more forms of ionizing radiation, or one or more immunomodulatory agents. The one or more forms of ionizing radiation can be gamma-irradiation, X-irradiation, or beta-irradiation. The one or more chemotherapeutic agents can be selected from the group consisting of cisplatin, carboplatin, procarbazine, mechlorethamine, cyclophosphamide, camptothecin, adriamycin, ifosfamide, melphalan, chlorambucil, bisulfan, nitrosourea, dactinomycin, daunorubicin, doxorubicin, bleomycin, plicomycin, mitomycin, etoposide, verapamil, podophyllotoxin, tamoxifen, taxol, thalidomide, lenalidomide, a proteasome inhibitor (e.g., bortezomib), an hsp90 inhibitor (e.g., tanespimycin), transplatinum, 5-fluorouracil, vincristine, vinblastine, methotrexate, or an analog of any of the aforementioned. Immunomodulatory agents include, e.g., a variety of chemokines and cytokines such as Interleukin 2 (IL-2), granulocyte/macrophage-colony stimulating factor (GM-CSF), and Interleukin 12 (IL-12).

Dosage

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic agent (i.e., an effective dosage) depends on the therapeutic agent selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic agents described herein can include a single treatment or a series of treatments.

Dosage, toxicity and therapeutic efficacy of the therapeutic agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

Pharmaceutical Compositions and Methods of Administration

The methods described herein include the use of pharmaceutical compositions comprising USP1 inhibitors and/or UAF1 inhibitor as active ingredients. In some embodiments, the only active ingredient in the pharmaceutical composition is a USP1 inhibitor. Thus, in some cases, the active agent in the pharmaceutical composition consists of a USP1 inhibitor.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., Remington: The Science and Practice of Pharmacy, 21st ed., 2005; and the books in the series Drugs and the Pharmaceutical Sciences: a Series of Textbooks and Monographs (Dekker, N.Y.). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, NJ) or phosphate buffered saline (PBS). In all cases, the composition must be sterile and should be fluid to the extent that easy syringeability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

Therapeutic compounds that are or include nucleic acids can be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al., Clin. Immunol. Immunopathol., 88(2), 205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

The pharmaceutical compositions can be included in a container, pack, or dispenser together with instructions for administration.

EXAMPLES

The invention is further described in the following examples, which do not limit the scope of the invention described in the claims.

Example 1

Materials and Methods

The following materials and methods were used in the examples.

Bioinformatics Analysis

The Cancer Genome Atlas (TCGA) datasets were accessed through the public portal (cBioPortal). Published TCGA datasets for breast and ovarian cancers in which both mutations and expression analyses were available were used (44,45). USP1 expression in BRCA1-mutant tumors was compared against BRCA1 wild-type tumors. GraphPad Prism was used to graph the data and carry out statistical analyses (Student's t test).

Cell lines, Antibodies, siRNAs and Plasmids

HeLa and 293T cells were grown in Dulbecco's Modified Eagle's medium (DMEM) (Gibco) supplemented with 10% fetal bovine serum. MDA-MB-436 cells were grown in RPMI (Gibco™, Thermo Fisher Scientific, Waltham, MA) supplemented with 10% fetal bovine serum. RPE cells were grown in DMEM/F12 (Gibco™, Thermo Fisher Scientific, Waltham, MA) supplemented with 10% fetal bovine serum. siRNA sequences against USP1 are 5'-TCGGCAATACTTGCTATCTTA-3' (SEQ ID NO: 1),
5'-CCATACAAACATTGGTAAA-3' (siRNA against 3'UTR) (SEQ ID NO: 2), and
5'-CACCGGTCATACCTAGTGAAAGTAA-3' (SEQ ID NO: 3) respectively.

Antibodies used included FANCD2 (FI-17, Santa Cruz, Dallas, Texas), Flag (M2, Sigma, St. Louis, MO), USP1 (34) (Sigma, St. Louis, MO), PCNA (PC-10, Santa Cruz, Dallas, Texas), and Vinculin (H-10, Santa Cruz, Dallas, Texas).

Generation of p53/BRCA1 Knockout RPE-1 Cells

Oligonucleotides encoding guide RNAs targeting TP53 and BRCA1 were cloned into the pSpCas9(BB)-2A-GFP vector (Addgene, Cambridge, MA, plasmid #48138). The targeted genomic sequences were GATCCACTCACAGTTTCCAT (SEQ ID NO: 4) for TP53
and TCTTGTGCTGACTTACCAGA (SEQ ID NO: 5) for BRCAL RPE-1 cells were transfected with the CRISPR-Cas9 targeting construct to TP53 using Lipofectamine 2000 (Invitrogen, Carlsbad, CA Cat #11668). 48 hours following transfection, GFP+ cells were selected and single cells were seeded using a BD FACSAria II cell sorter. Single cells were grown for approximately 3 weeks. TP53 knockout clones were identified by western blotting. The same procedure was used to knock out BRCA1 in a TP53 knockout RPE-1 cell line. BRCA1 knockout clones were identified by western blotting and confirmed by Sanger sequencing.

Western Blotting

Cells were lysed with lysis buffer (300 mM NaCl, 50 mM Tris-Cl, 1 mM EDTA, 0.5% NP-40), lysates resolved on denaturing Nupage (Invitrogen, Carlsbad, CA) polyacrylamide gels and transferred onto nitrocellulose membranes. Membranes were blocked with 5% milk in TBST, and probed with primary and secondary antibodies respectively, then detected with chemiluminescence (Western Lightning, Perkin Elmer, Waltham, MA).

iPOND (Isolation of Protein on Nascent DNA)

Accelerated native iPOND was performed as described in Leung K, Abou EHM, Bremner R. A rapid and efficient method to purify proteins at replication forks under native conditions. Biotechniques. 2013; 55(4):204-6. Briefly, 2-4 15 cm dishes of 293T cells were plated at a density of 15 million cells per plate. Cells were treated with hydroxyurea for 16 h then pulsed with EdU for 10 min. Nuclei were then harvested and resuspended in the click reaction mix for an hour. Samples were then lysed and sonicated and streptavidin pull-down performed overnight at 4° C. Beads were washed 5-7 times then boiled with loading buffer containing 2-mercaptoethanol for 20 min. Samples were then resolved in Nupage (Invitrogen, Carlsbad, CA) polyacrylamide gels and transferred onto nitrocellulose membranes for blotting.

Replication Combing Assay

Replication combing assay was performed using the FiberComb machine (Genomic Vision, Bagneux, France). Br iefly, cells were treated with CldU, IdU then HU, with 3 PBS washes between each treatment. Cells were then trypsinized, counted and embedded in low melting point agarose plugs, then treated with proteinase k overnight. Agarose plugs were then washed and digested with agarase. Agarase-treated samples were then poured into FiberComb wells and combed onto silanized coverslips. Coverslips were probed with rat anti-BrdU antibody (clone BU1/75 ($ICR_1$) specific to CldU, Life Technologies, Woburn, MA, #MA1-82088) and mouse anti-BrdU Antibody (specific to IdU, BD Biosciences, Woburn, MA, #347580) and visualized by fluorescence microscopy. Pictures were taken of at least 100 fibers per condition. Fibers were measured with ImageJ and graphed.

Sensitivity Assays

Cells were transfected with siRNA or plasmid 18-24 h before being plated for colony formation assays. Cells were counted and plated in triplicates in 6-well plates. For treatment with ML323, plated cells were allowed to adhere overnight before treatment with ML323 the next day. At the end of the experiment, cells were fixed with methanol for 10 min at −20° C. then stained with crystal violet. Quantification of cell growth area was performed with ImageJ.

Protein Purification, In Vitro Deubiquitination Assays and Electromobility Shift Assays Preparation of recombinant USP1 and UAF1 wild type and mutant proteins in SF9 cells and Ub-AMC assays were performed by the method as described in Cohn M A, Kowal P, et al. A UAF1-containing multisubunit protein complex regulates the Fanconi anemia pathway. Molecular cell. 2007; 28(5):786-97. Ub-CHOP2 assays (Life Sensors, Malvern, PA, PR1101) were performed according to manufacturer's instructions. Ub-AMC assays were performed by the methods as described in Cohn M A et al., UAF1 is a subunit of multiple deubiquitinating enzyme complexes. The Journal of biological chemistry. 2009; 284(8):5343-51; Cohn M A, et al. A UAF1-containing multisubunit protein complex regulates the Fanconi anemia pathway. Molecular cell. 2007; 28(5):786-97; Kee Y, et al., $WDR_{20}$ regulates activity of the USP12 UAF1 deubiquitinating enzyme complex. Journal of Biological Chemistry. 2010; 285(15):11252-7; and Mistry H, Hsieh G, et al. Small-molecule inhibitors of USP1 target ID1 degradation in leukemic cells. Molecular cancer therapeutics. 2013; 12(12):2651-62.

Recombinant USP1 and UAF1 proteins from R&D systems (E564, E566) were used for some electromobility shift assays and in vitro deubiquitination assays. Electromobility shift assays were performed by pre-incubating fluorophore (Cy3)-tagged DNA and purified protein in binding buffer (20 mM Hepes (pH 7.6), 0.1M KCl, 5 mM MgCl2, 3% (v/v) glycerol, 0.25 mg/ml BSA, 0.05 mM EDTA, 0.5 mM DTT, 0.01% (v/v) NP-40) for 30 min on ice. Samples were then loaded onto 6% polyacrylamide gels and ran at 65V in 0.5× TBE for 135 min at 4° C. Gels were visualized using the LAS-4000 imaging system (GE Healthcare Life Sciences, Pittsburgh, PA). DNA used for Ub-AMC, Ub-CHOP2 and electromobility shift assay were 40 bp in length and were designed to have minimal potential of secondary structure formation. The sequences are as follows:

```
40-mer top
                                      (SEQ ID NO: 6)
(5'-CCAGTGAATTGTTGCTCGGTACCTGCTAACGGTAATCGG-3');

40-mer ds-bottom
                                      (SEQ ID NO: 7)
(5'-CCGATTACCGTTAGCAGGTACCGAGCAACAATTCACTGG-3');

40-mer fork bottom
                                      (SEQ ID NO: 8)
(5'-CAGCTATGGGACATTCGATACCGAGCAACAATTCACTGG-3').
```

Statistical Analysis iPOND densitometry data are represented as mean±SEM over at least 3 independent experiments. Fiber assay and Ub-AMC data are represented as mean±SD in one representative experiment and repeated at least 3 times with similar results. Significance was determined by Student's t test and calculated using the Graphpad Prism software unless otherwise stated.

Example 2

Figure 1A:
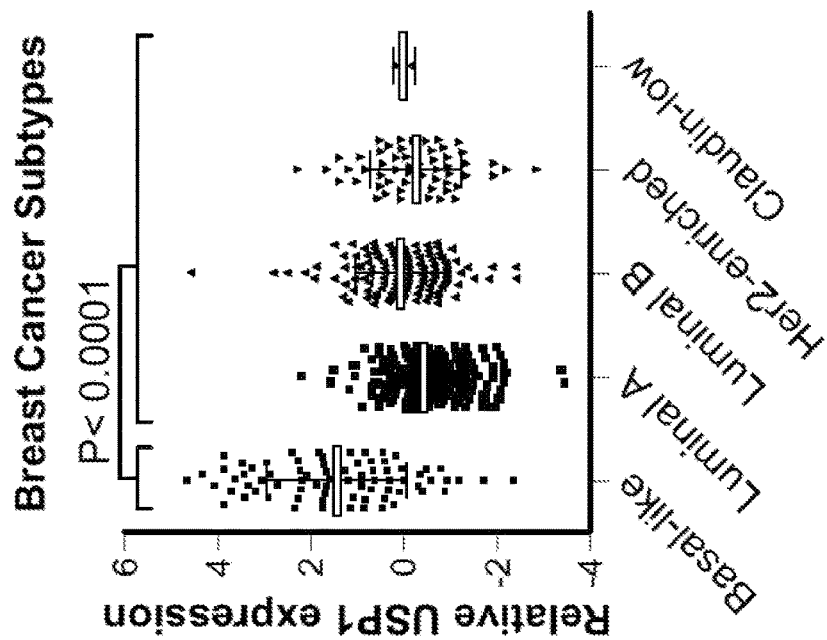
FIG. 1A. USP1 mRNA levels in HR-deficient basal-like breast cancers were plotted against other breast cancer subtypes using data from the Cancer Genome Atlas (TCGA).
Figure 1D:
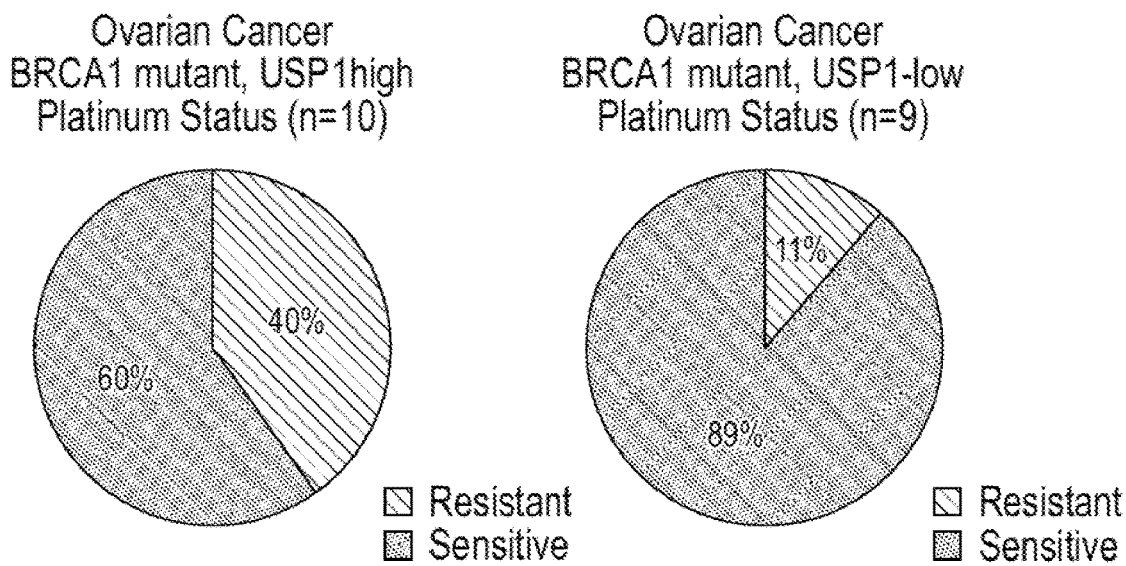
FIG. 1D. Platinum status of BRCA1 mutant ovarian cancers with high USP1 expression levels or low USP1 expression levels were graphed using data from TCGA.
Figure 8A:
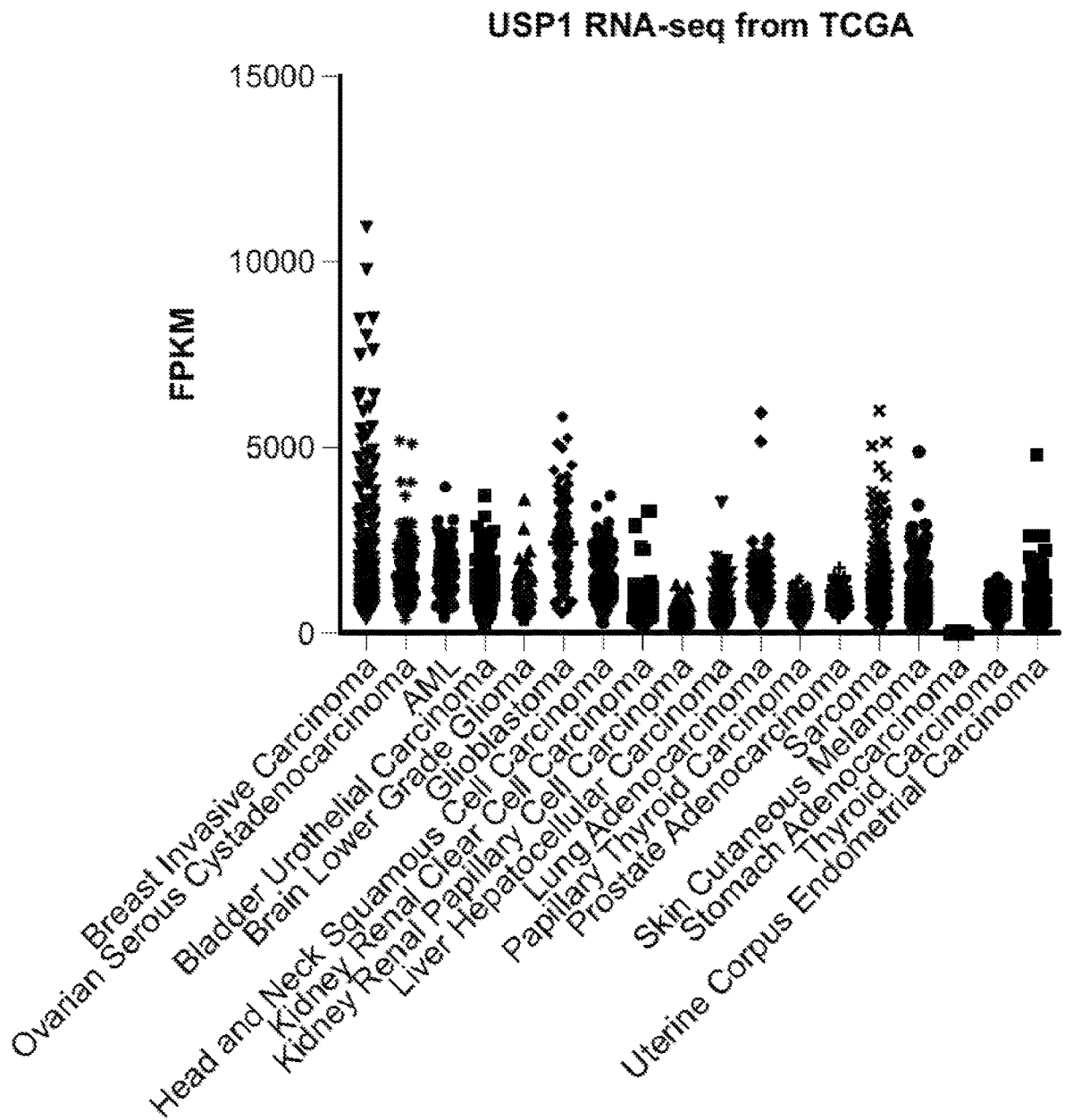
FIG. 8A. USP1 expression levels from different tumor types plotted using RNA-seq data from TCGA.
Figure 8B:
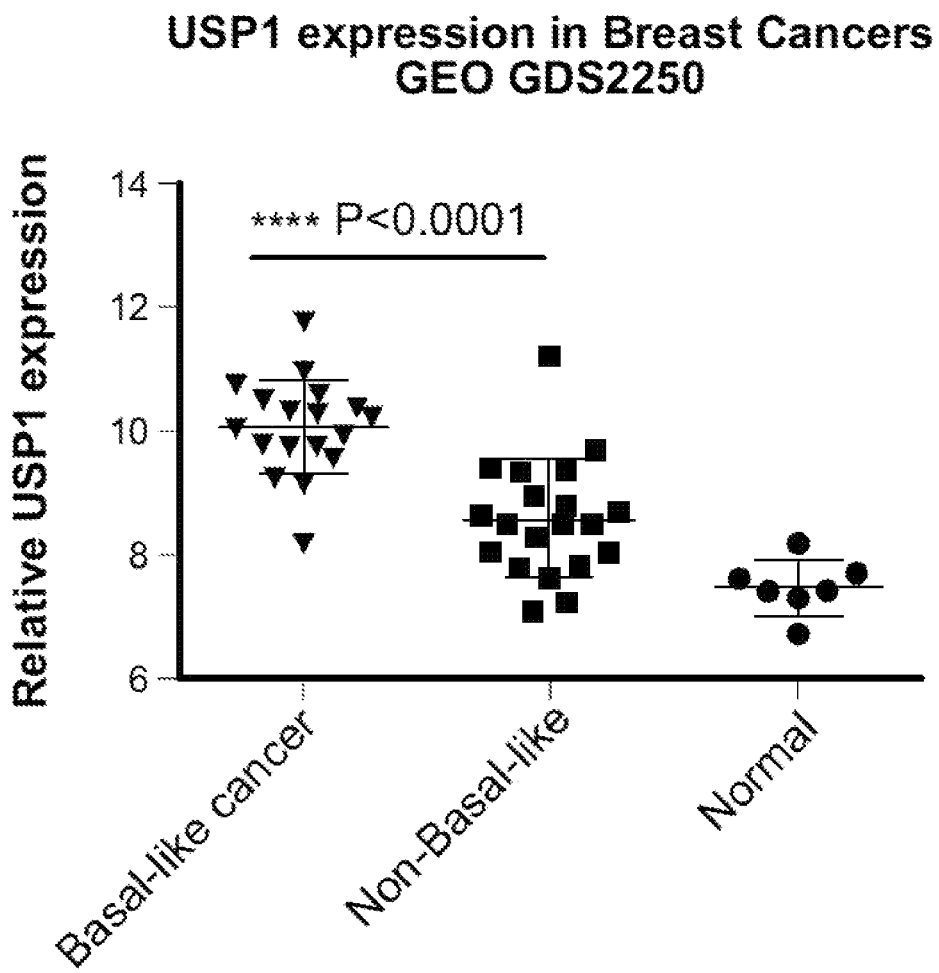
FIG. 8B. USP1 expression levels from basal-like and non-basal-like breast cancers from GEO dataset GDS2250.
Figure 8D:
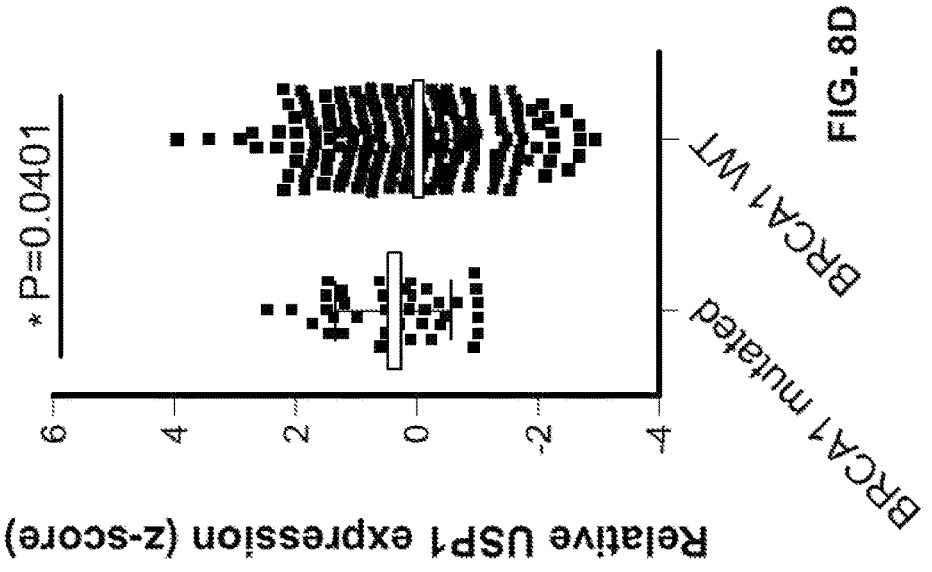
FIG. 8D. USP1 mRNA levels in BRCA1 mutated vs BRCA1 wild-type ovarian cancers were plotted using data from TCGA.
Figure 8C:
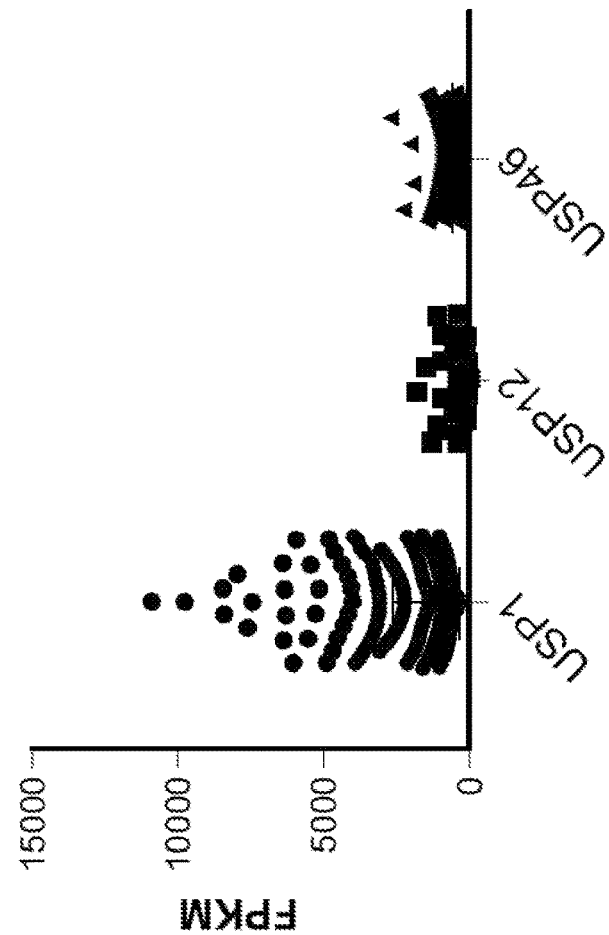
FIG. 8C. USP1, USP12 and USP46 expression levels in breast cancers plotting using RNA-seq data from TCGA.
Figures 8E, 8F:
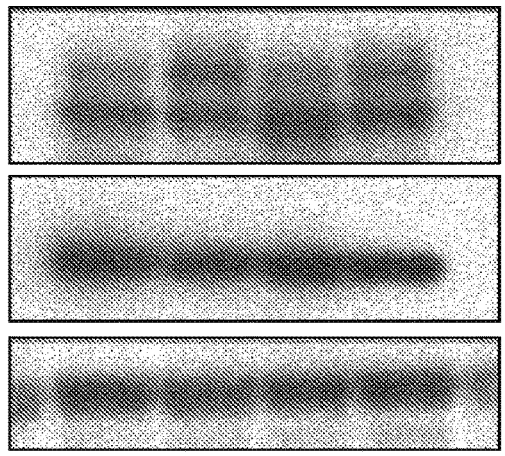
FIG. 8E. Table of top 5 mutated genes in breast tumors expressing high levels of USP1 and low levels of USP1.
FIG. 8F. Western blot of USP1 with and without ML323 treatment. Following inhibition of USP1 deubiquitinating enzyme (DUB) activity, USP1 autocleavage is inhibited, resulting in a more intense top USP1 band. In addition, Ser313 phosphorylation is induced, resulting in a higher MW band in the blot.

USP1 is Overexpressed in BRCA1-Deficient Tumors and Contributes to Replication Fork Stabilization USP1 expression levels were determined in different breast cancer subtypes. USP1 was significantly overexpressed in HR-deficient basal-like breast cancers compared to the other subtypes (P<0.0001) (FIG. 1A). Further analysis revealed that USP1 overexpression is significantly correlated with BRCA1 deficiency in breast tumors (P<0.0001) (FIGS. 1A and 8C). A similar correlation was observed in BRCA1 deficient ovarian tumors (FIG. 8D). In contrast, overexpression of USP1 in BRCA2 mutant tumors was not observed.

Figure 1E:
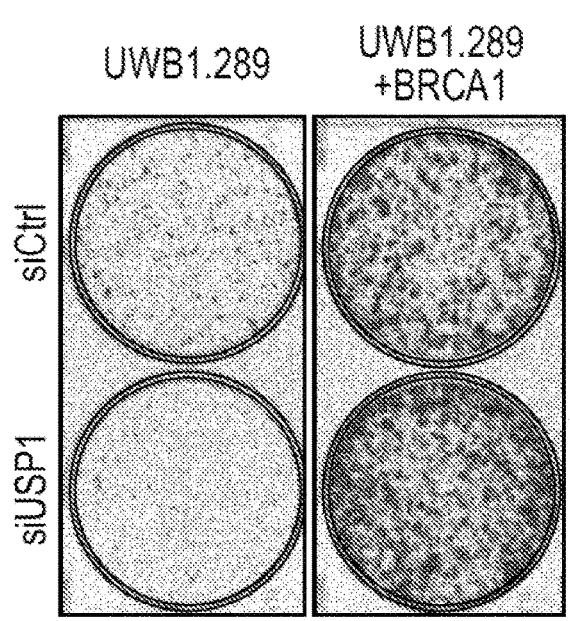
FIG. 1E. Representative colony pictures of UWB1.289 and UWB1.289+BRCA1 with either siCtrl or siUSP1.
Figure 1F:
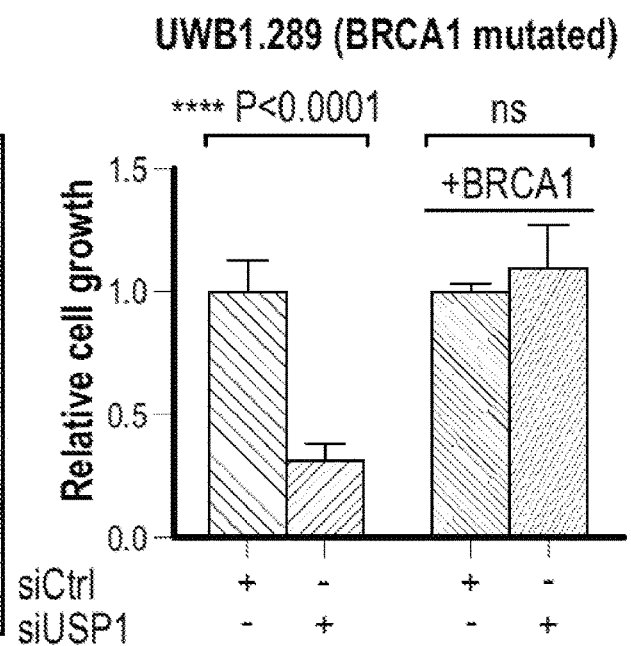
FIG. 1F. Graphical quantification of a colony formation assay of BRCA1 mutated ovarian cancer line UWB1.289 and its isogenic BRCA1 reconstituted sub-line, following treatment with either control siRNA or USP1 siRNA.
Figure 1G:
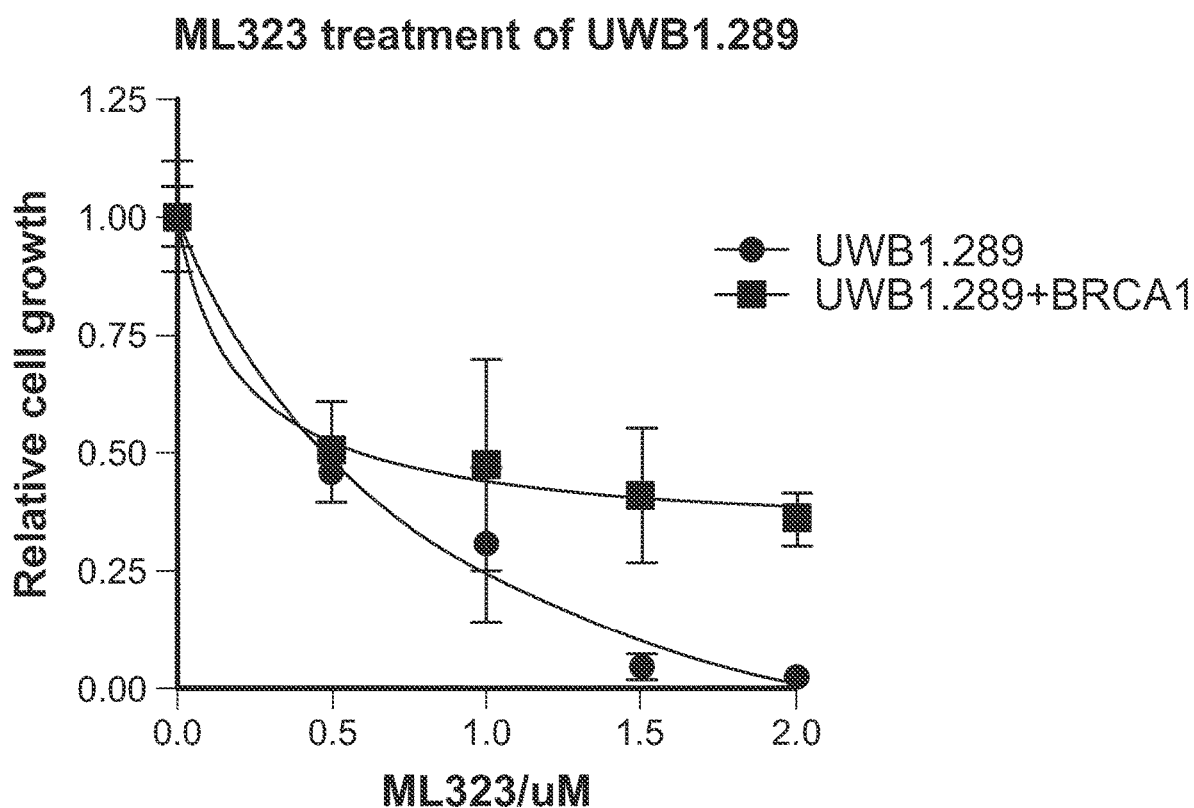
FIG. 1G. Dose-response graph of UWB1.289 and UWB1.289+BRCA1 treated with a USP1 inhibitor ML323.

Experiments were then performed to examine a potential synthetic lethal relationship between BRCA1 and USP1 in a BRCA1-mutant ovarian cancer cell line, UWB1.289. Silencing USP1 by siRNA transfection resulted in reduced growth of UWB1.289 but not of UWB1.289+BRCA1 complemented cells (FIG. 1E). Treatment of UWB1.289 with a specific DUB inhibitor of USP1, ML323, also resulted in reduced growth compared to UWB1.289+BRCA1 (FIG. 1G).

Figure 15:
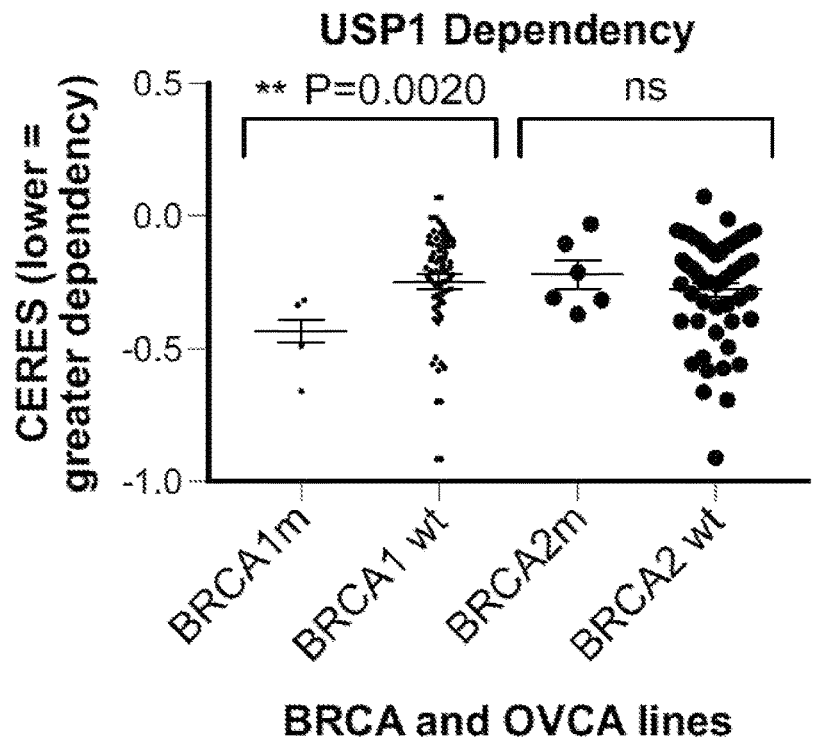
FIG. 15. CRISPR gene-knockout effects inferred by CERES were compared in 57 breast and ovarian cancer cell lines grouped by BRCA1 or BRCA2 mutation status, using data from the Broad Institute Cancer Dependency Map and Cancer Cell Line Encyclopedia. Bars reflect mean±SEM. CERES values for wild-type versus mutant cell lines were compared via the Mann-Whitney U test.
Figure 19A:
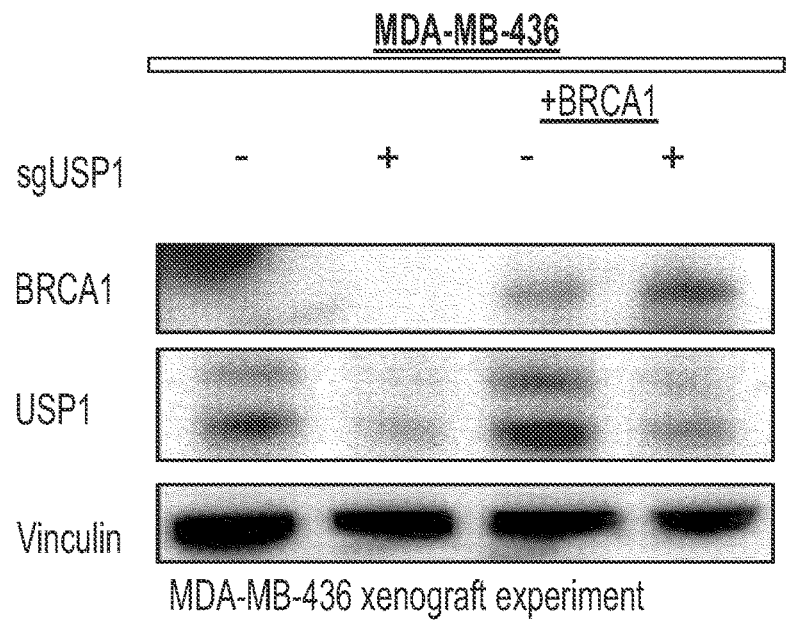
FIG. 19A. Reduced tumor growth of BRCA1-deficient MDA-MB-436 breast cancer cells with CRISPR-mediated knockout of USP1. Western blot of the lysates from MDA-MB-436 cells and MDA-MB-436+BRCA1 cells following USP1 knockout.
Figure 19B:
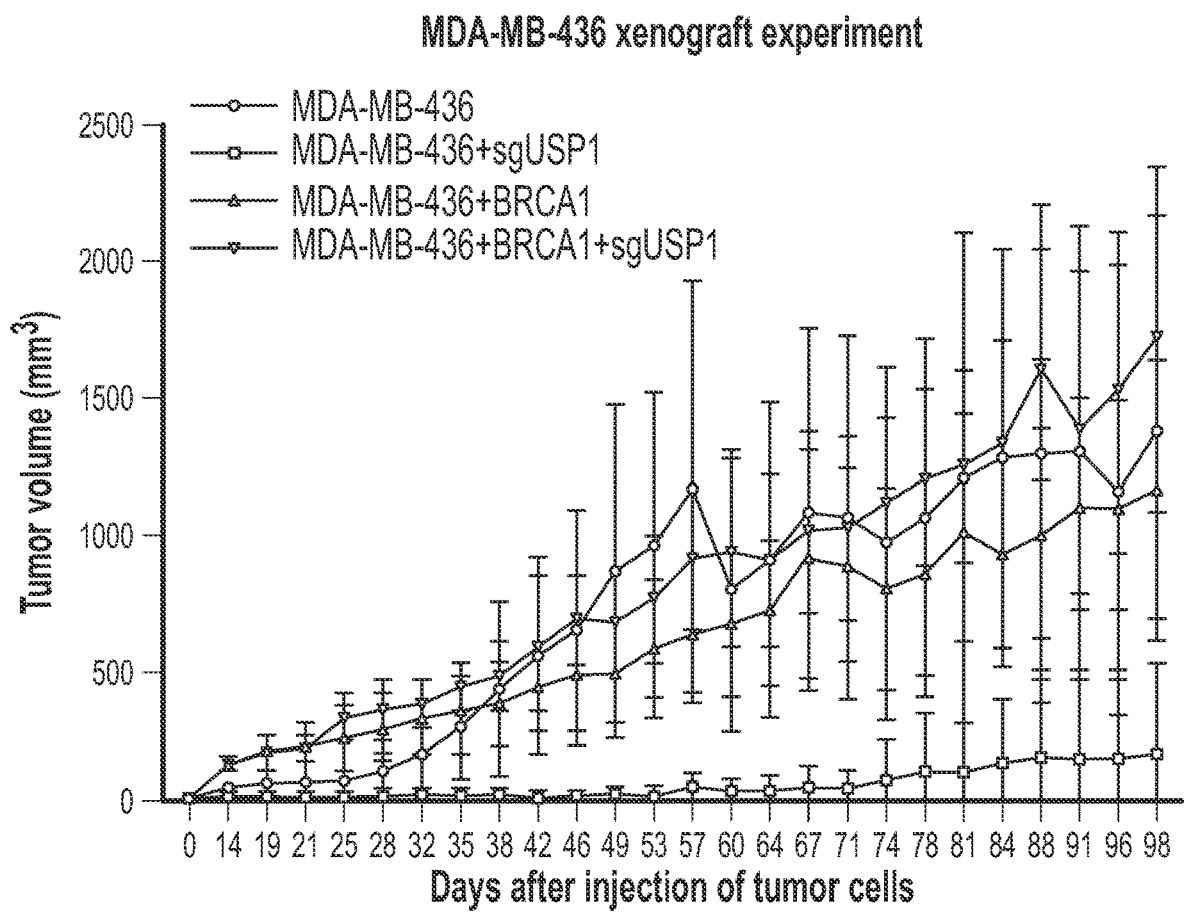
FIG. 19B. Tumor growth of MDA-MB-436 cells, MDA-MB-436+sgUSP1 cells, MDA-MB-436+BRCA1 cells and MDA-MB-436+BRCA1+sgUSP1 cells in athymic nude mice. 5 mice/group were used, and the tumor cells were implanted on both the flanks of mice. P-values of MDA-MB-436+sgUSP1 group vs every other group <0.0001.

Inhibition of USP1 activity by treatment of UWB1.289 cells with a specific DUB inhibitor of USP1, ML323 also resulted in reduced growth of UWB1.289 cells compared to UWB1.289+BRCA1 cells. Synthetic lethality between USP1 and BRCA1 was also evident in another cancer cell line using an in vivo mouse xenograft model (FIGS. 19A-19B). BRCA1 deficient MDA-MB-436 breast cancer cells with CRISPR-mediated knockout of USP1 exhibited significantly reduced tumor growth in athymic nude mice compared to MDA-MB-436 cells with reconstitution of BRCA1 (FIGS. 19A-19B). A cancer dependency study also confirmed that BRCA1-deficient, but not BRCA2-deficient, breast and ovarian cell lines are hyperdependent on USP1 for survival (FIG. 15). Depletion of USP1 also did not affect the growth of BRCA2 deficient VU423 cells.

BRCA1-deficient cells are deficient in replication fork stabilization and are dependent on FANCD2 for fork protection and restart (6). Since USP1 regulates the levels of FANCD2 monoubiquitination, experiments were performed to examine the role of USP1 in replication fork protection in BRCA1 deficient cells.

Figure 20B:
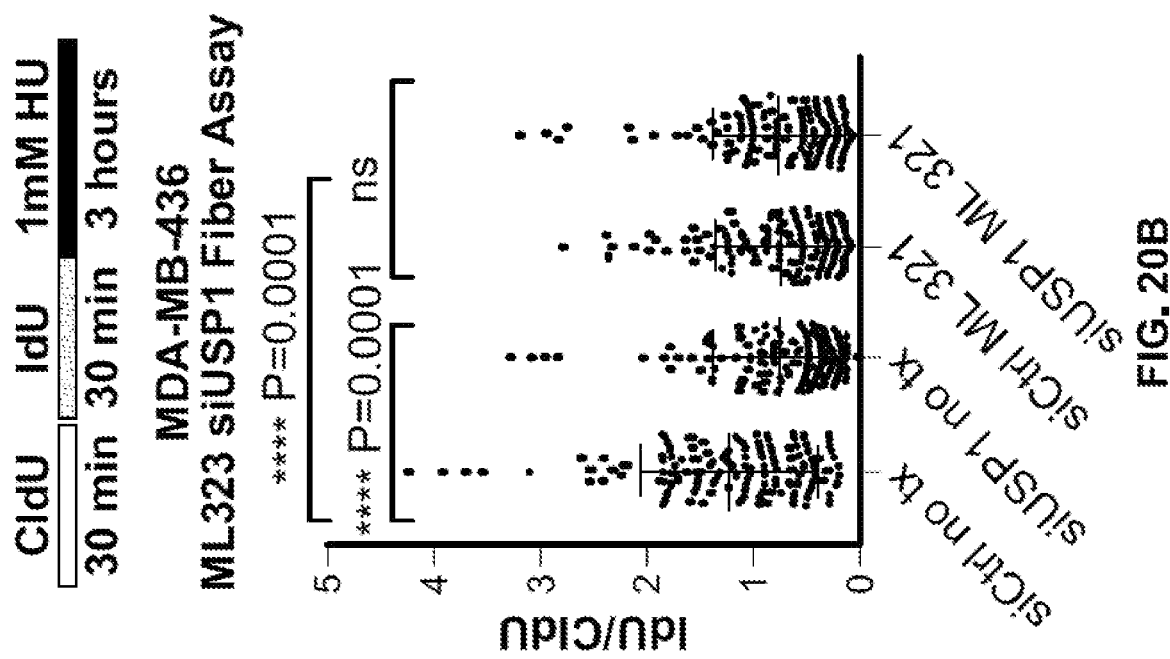
FIG. 20B. Schematic of the experimental design for the fiber assay, graphical quantification of fiber assay measuring replication fork stability in MDA-MB-436 cells following treatment with either siCtrl or siUSP1, untreated or treated with 10 µM of ML323 for 24 h.
Figure 20A:
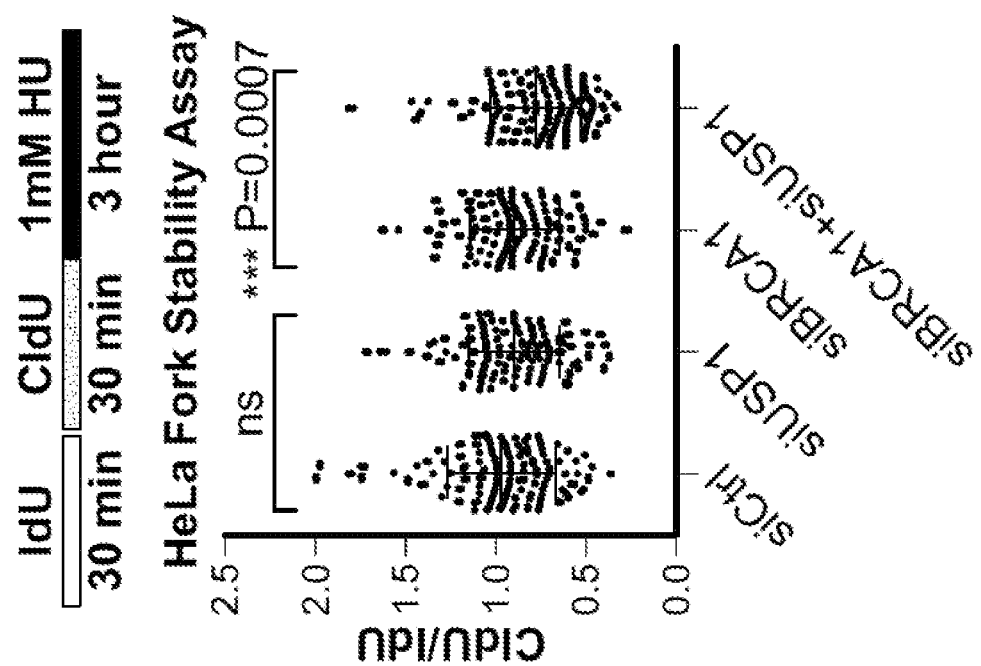
FIG. 20A. Schematic of the experimental design for the fiber assay and quantification of fiber assay measuring replication fork stability in BRCA1 proficient and BRCA1 deficient HeLa cells following USP1 silencing.

Functional complementation of BRCA1 was confirmed by PARP inhibitor resistance in UWB1.289+BRCA1 cells. A low dose of hydroxyurea (1 mM) that does not lead to replication fork instability in BRCA1 deficient cells was used. Hydroxyurea treatment of BRCA1 deficient cells for 3 h did not result in replication fork instability (FIG. 20A). Treatment of BRCA1 deficient MDA-MB-436 cells with the USP1 inhibitor ML323 also resulted in enhanced fork degradation following hydroxyurea treatment, and this effect is not increased with USP1 silencing (FIG. 20B).

Figure 2A:
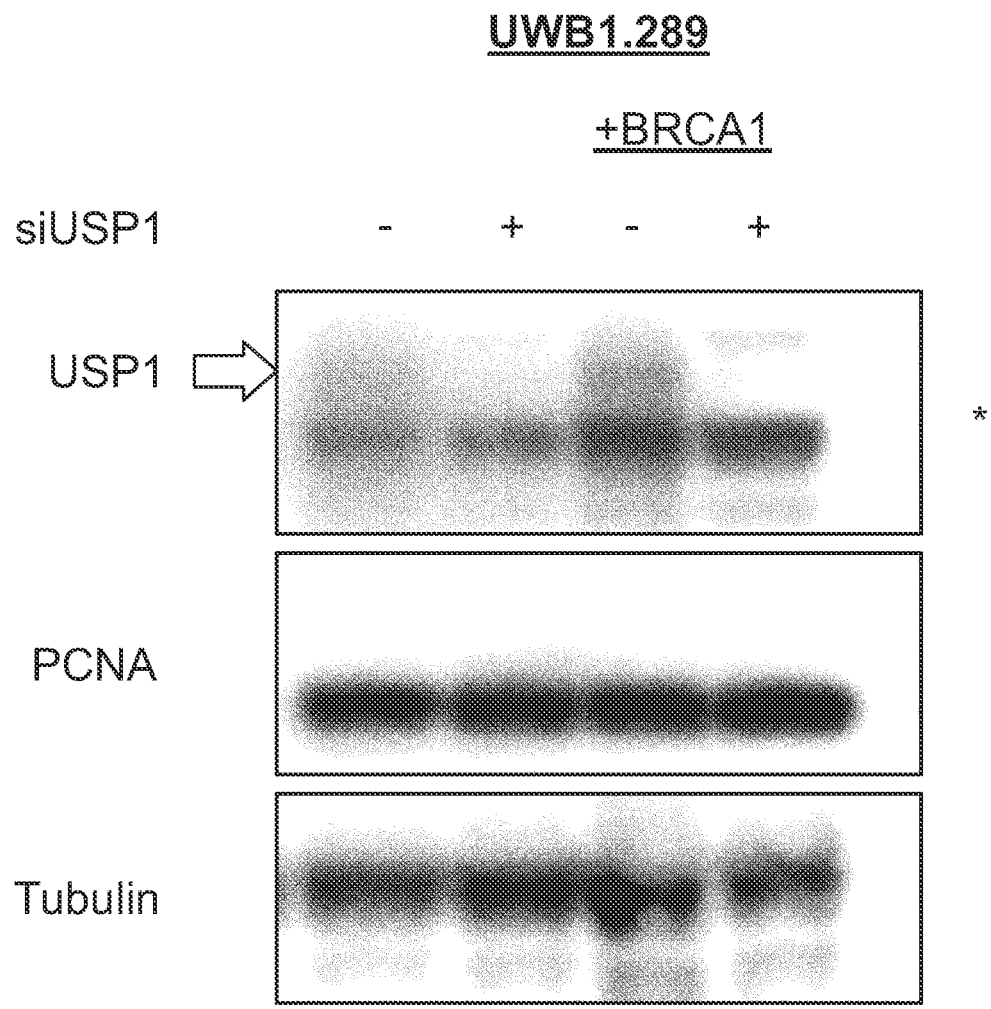
FIG. 2A. Western blot of UWB1.289 and UWB1.289+BRCA1 following USP1 silencing (* indicates non-specific band).
Figure 2B:
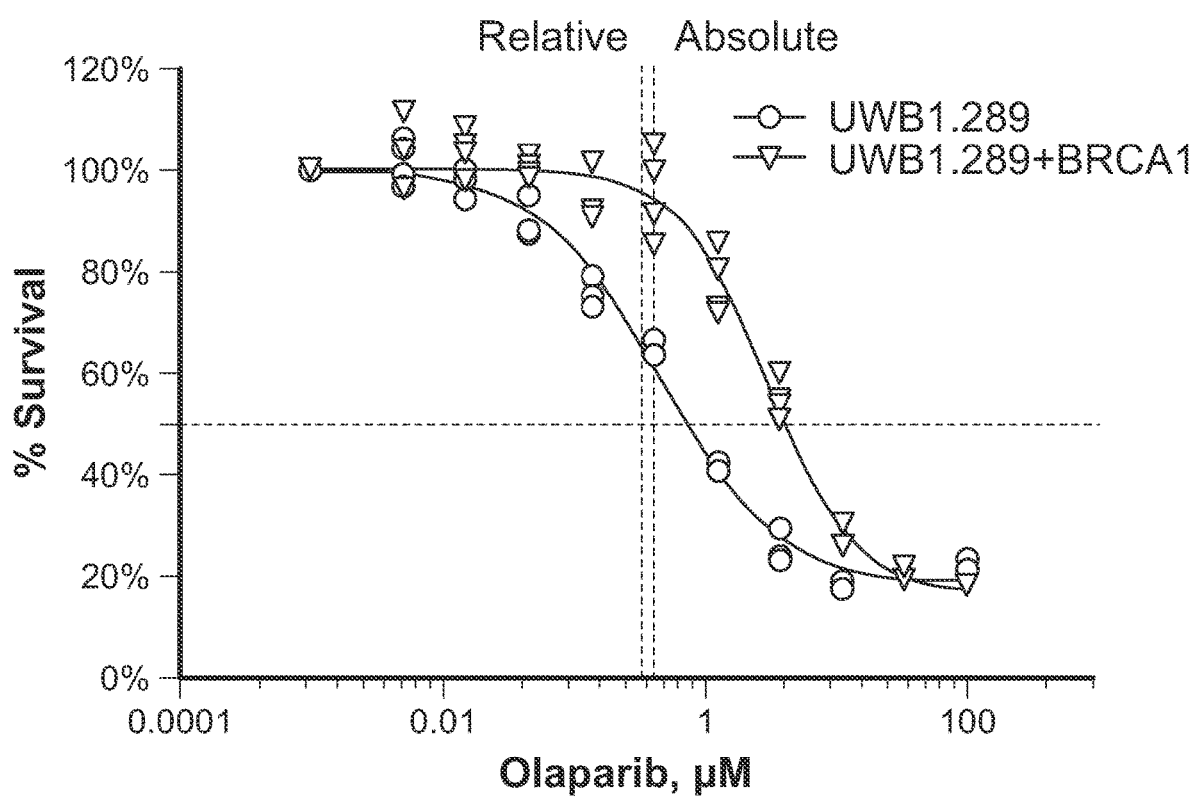
FIG. 2B. IC50 blot of UWB1.289 and UWB1.289+BRCA1, showing functional rescue of BRCA1 in the reconstituted UWB1.289 cells.
Figure 2C:
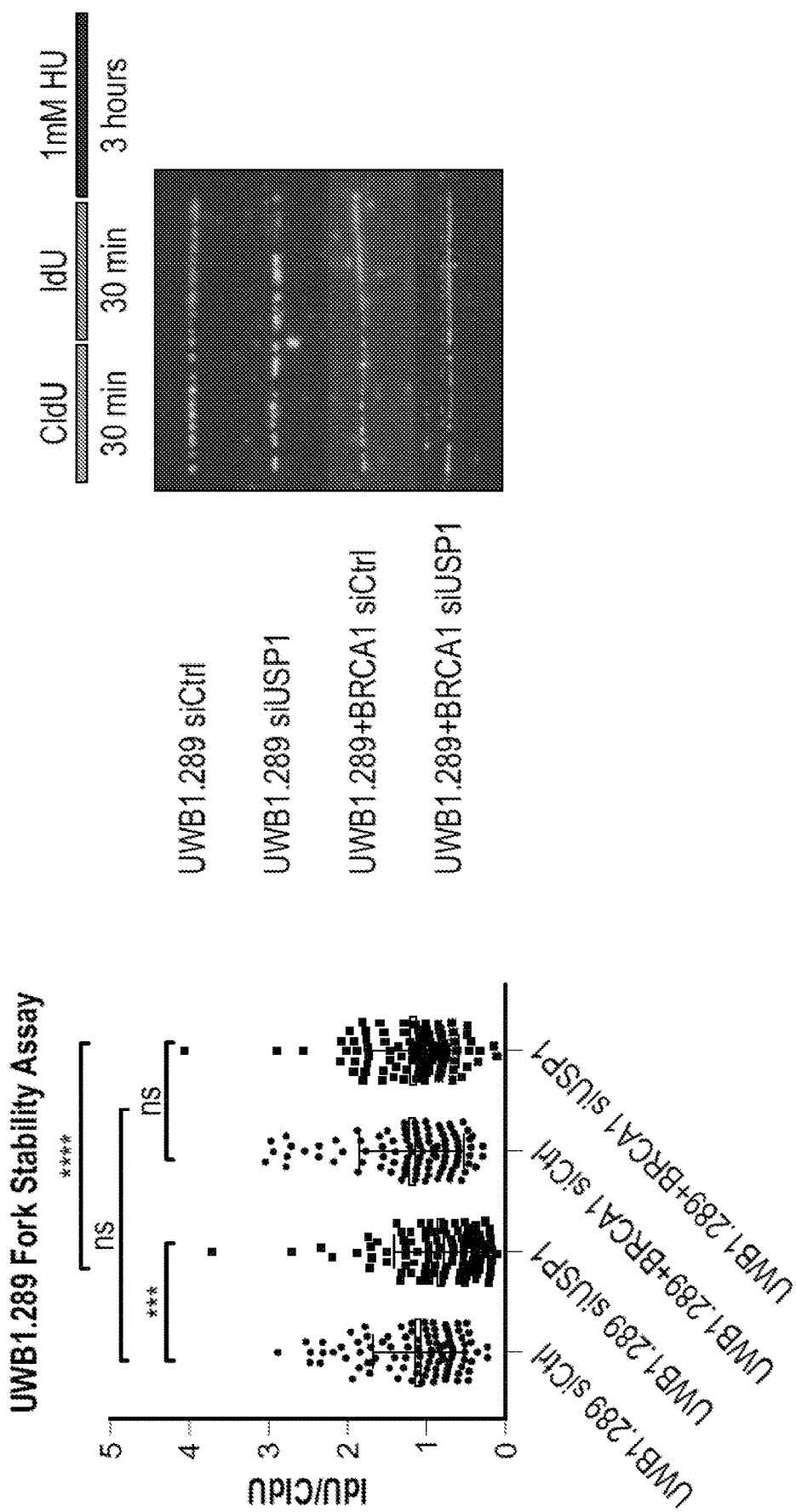
FIG. 2C. Fiber assay measuring fork resection in UWB1.289 and UWB1.289+BRCA1 cells following USP1 silencing. Left: Graphical quantification of fiber length. Right: Representative fibers.
Figure 9B:
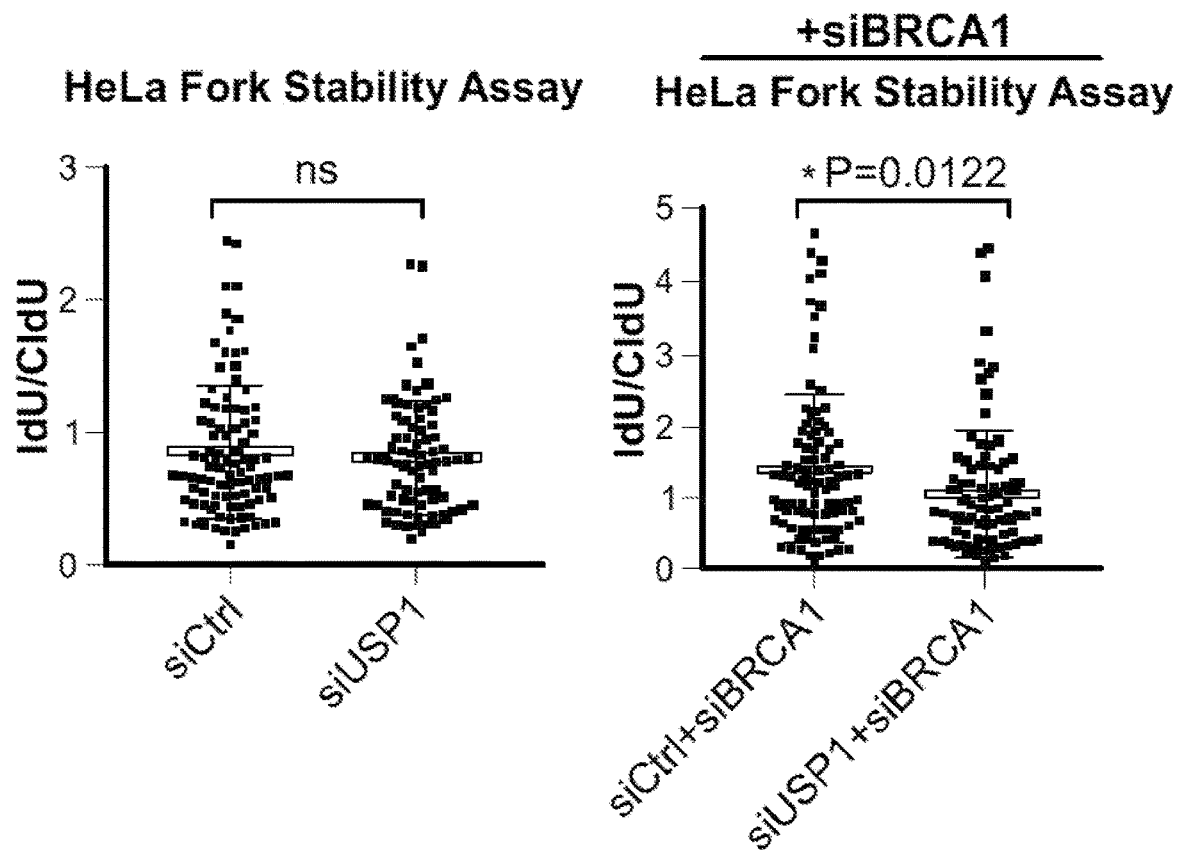
FIG. 9B. Quantification of fiber assay in BRCA1 proficient (left graph) and BRCA1 deficient (right graph) HeLa cells following USP1 silencing.
Figure 9C:
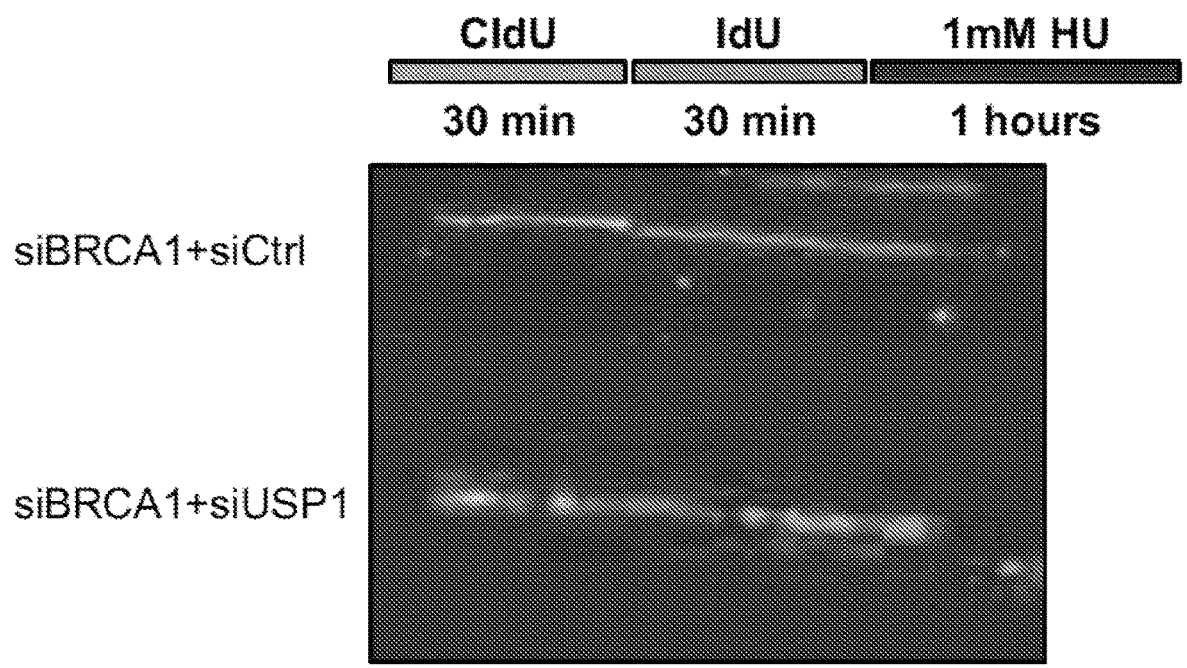
FIG. 9C. Representative fibers of BRCA1 deficient HeLa cells with and without siUSP1 treatment.
Figure 9D:
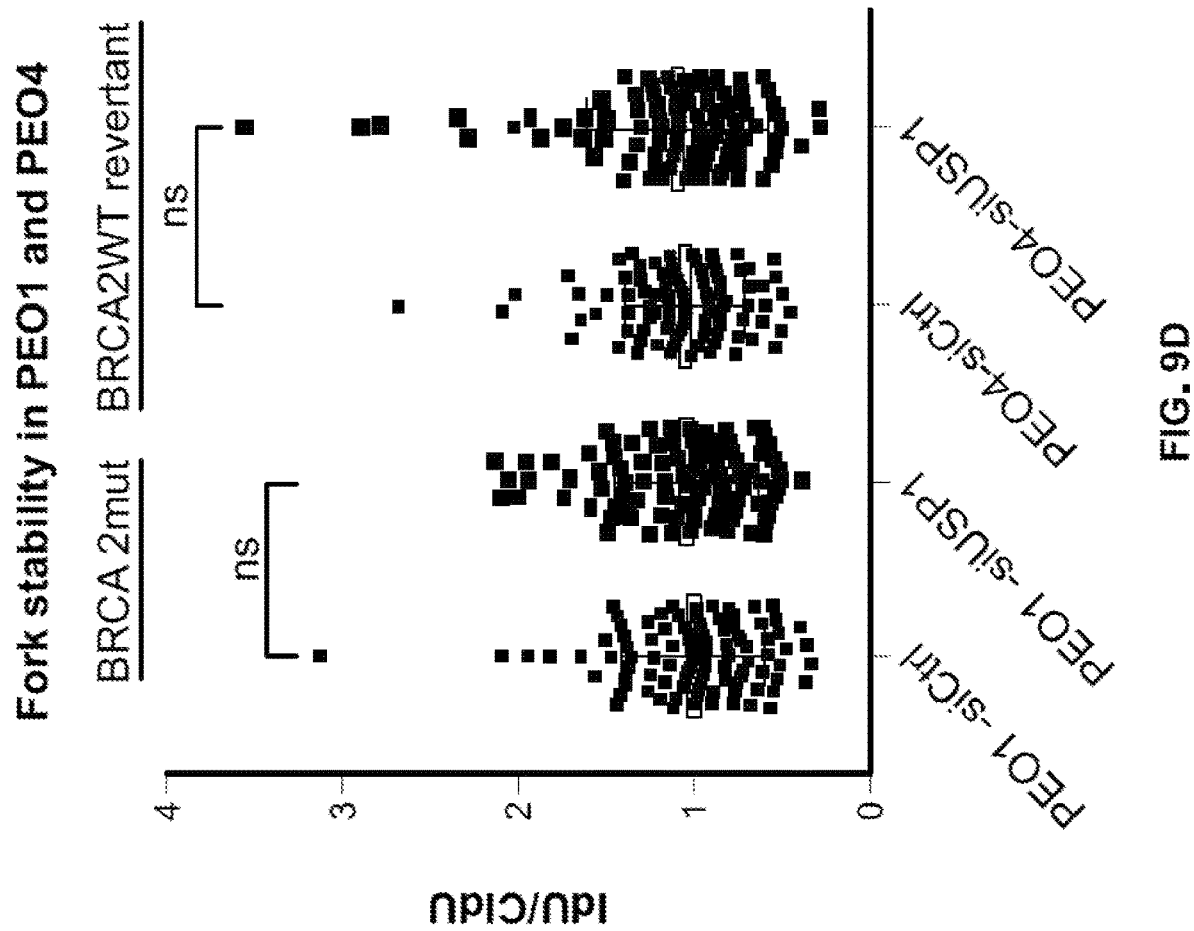
FIG. 9D. Quantification of fork stability in PEO1 (BRCA2 mutant) and PEO4 (BRCA2 wild type revertant) cells following USP1 silencing.

Silencing of USP1 in HeLa cells had no significant effect on hydroxyurea-mediated fork stalling and resection; however, silencing of USP1 and BRCA1 led to a significantly higher level of fork resection (FIG. 9B). Similarly, knockdown of USP1 in BRCA1-deficient UWB1.289 cells resulted in enhanced fork resection. In contrast, there was no difference in replication fork resection in BRCA1-complemented UWB1.289 cells when USP1 was silenced compared to control (FIG. 2C). Silencing of USP1 in BRCA2 deficient cells also did not lead to a decrease in fork stability (FIG. 9D). Taken together, these results indicate that BRCA1 and USP1 play redundant roles in replication fork stabilization, and suggest that USP1 is upregulated in BRCA1 deficient cells to compensate for the replication fork instability of these cells.

Also, siRNA knockdown of USP1 in BRCA1-deficient RPE cells resulted in increased chromosomal breaks and aberrations (FIGS. 20C-20E).

Example 3

USP1 is a DNA Binding Protein

Figure 3A:
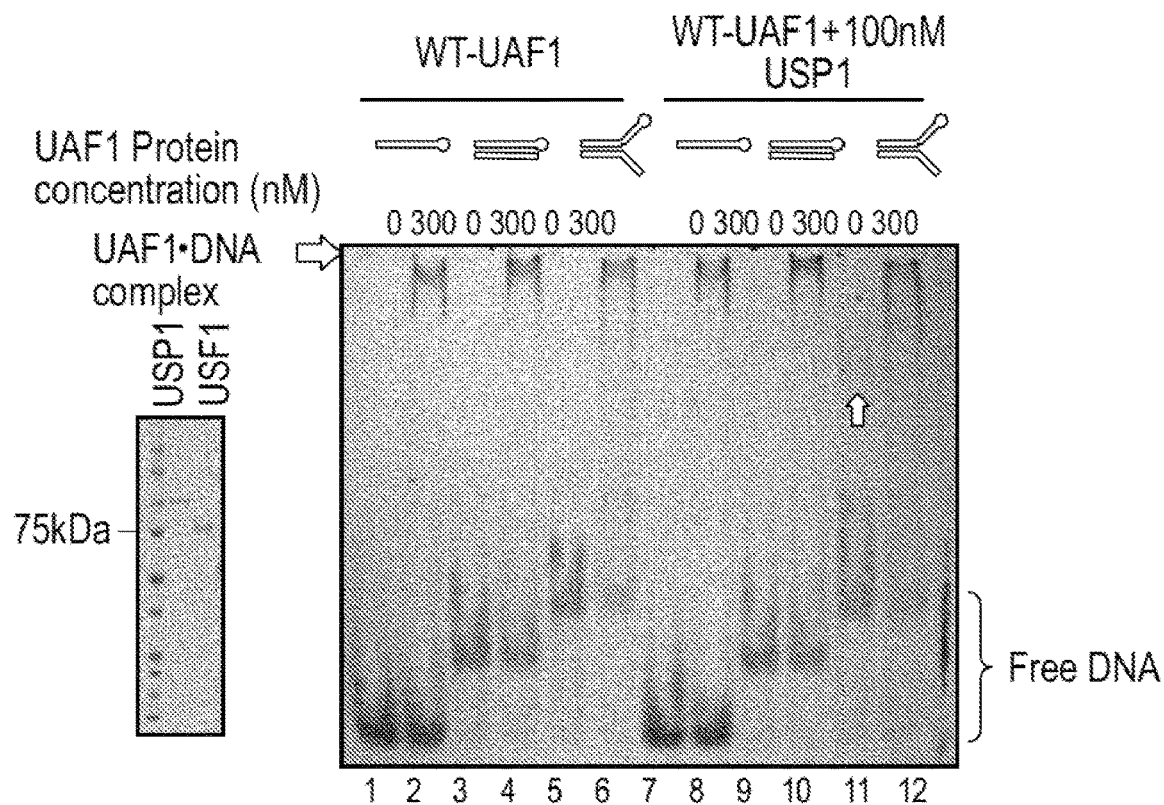
FIG. 3A. Coomassie gel of USP1 and UAF1 (left) and electromobility shift gel of ssDNA with 0 nM and 300 nM of UAF1 (lanes 1 and 2), dsDNA with 0 nM and 300 nM of UAF1 (lanes 3 and 4), fork DNA with 0 nM and 300 nM of UAF1 (lanes 5 and 6), ssDNA with 100 nM USP1+0 nM and 300 nM of UAF1 (lanes 7 and 8), dsDNA with 100 nM USP1+0 nM and 300 nM of UAF1 (lanes 9 and 10), fork DNA with 100 nM USP1+0 nM and 300 nM of UAF1 (lanes 11 and 12) (right).
Figure 3B:
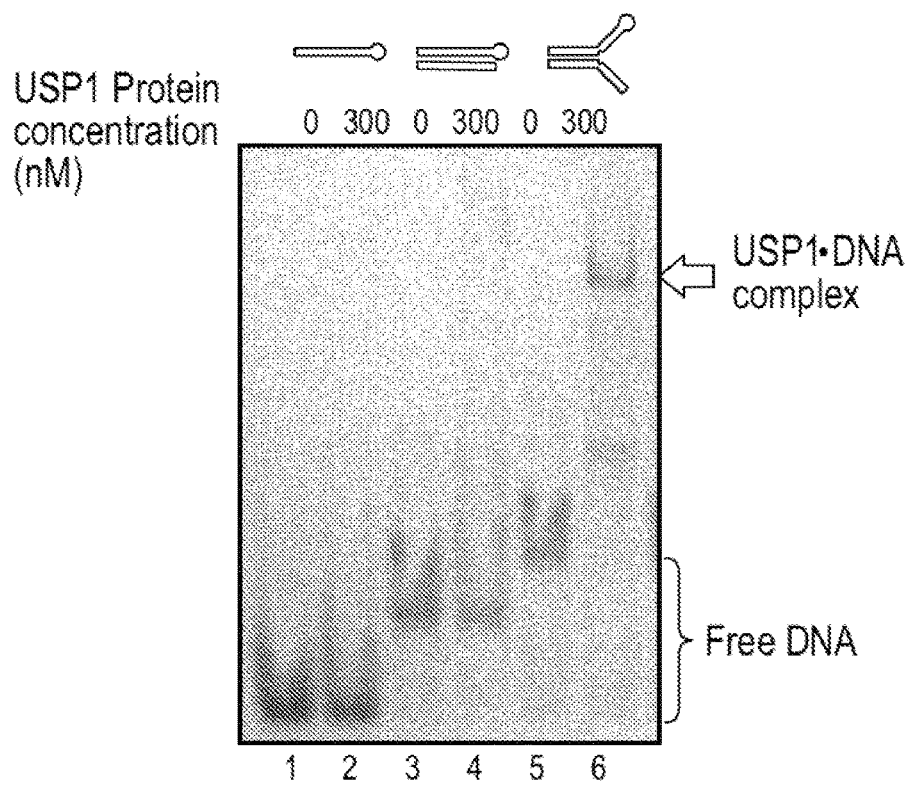
FIG. 3B. Electromobility shift gel of ssDNA with 0 nM and 300 nM USP1 (lanes 1 and 2), dsDNA with 0 nM and 300 nM USP1 (lanes 3 and 4), and fork DNA with 0 nM and 300 nM USP1 (lanes 5 and 6).

Since UAF1 has DNA binding activity, USP1 might also bind DNA and thereby stabilize replication forks. To test this hypothesis, DNA gel shift assays were performed with purified UAF1 protein with or without purified USP1 protein to analyze direct DNA binding activity. Purified proteins were incubated with either single strand DNA, double strand DNA, or fork DNA. The UAF1 protein and the USP1/UAF1 complex generated a reproducible gel shift of all three DNA templates. Interestingly, free USP1 also generated an upward shift of double strand DNA and, more strongly, of fork DNA (see arrows in FIG. 3A, lane 11 and FIG. 3B, lane 6).

Figure 3C:
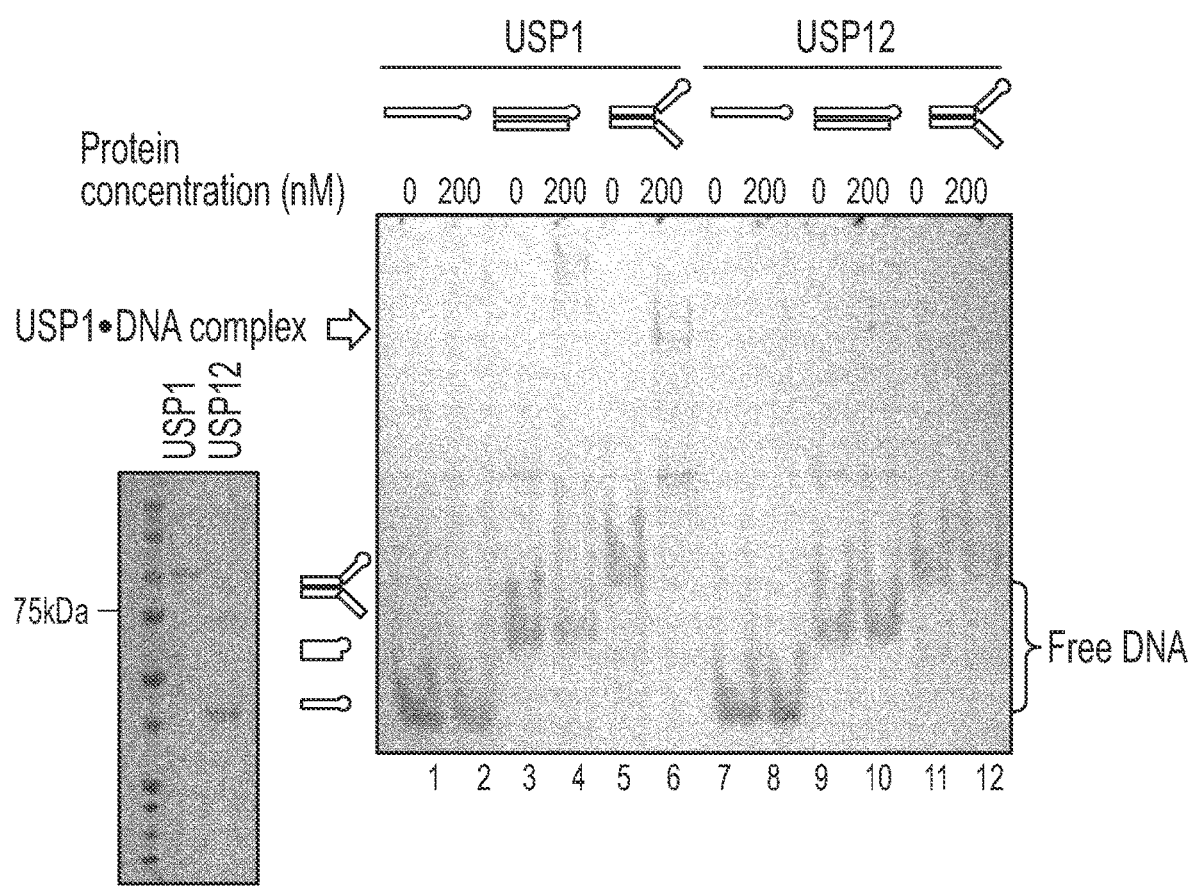
FIG. 3C. Coomassie gel of USP1 and USP12 (left) and electromobility shift gel of USP1 and USP12 with DNA. ssDNA with 0 nM and 300 nM USP1 (lanes 1 and 2), dsDNA with 0 nM and 300 nM USP1 (lanes 3 and 4), fork DNA with 0 nM and 300 nM USP1 (lanes 5 and 6), and ssDNA with 0 nM and 300 nM USP12 (lanes 7 and 8), dsDNA with 0 nM and 300 nM USP12 (lanes 9 and 10), fork DNA with 0 nM and 300 nM USP12 (lanes 11 and 12) (right).

USP1, USP12, and USP46 are related DUB proteins which bind and are stimulated by UAF1 (20, 23, 24, 31, 32). All three proteins contain a conserved UAF1 binding site, localized to a zinc finger region of each polypeptide (FIG. 10A). These USPs bind to a discrete WD40 domain of UAF1 (23, 24). Of the three proteins, USP1 is the largest protein, as shown by the sequence alignment with USP12 and USP46 (FIG. 10C). While USP1 binds and shifts fork DNA upward (FIG. 3C, lanes 1-6), USP12 fails to bind DNA (lanes 7-12), suggesting that the DNA binding region of USP1 is localized to non-conserved region(s) of these two proteins.

Figure 3D:
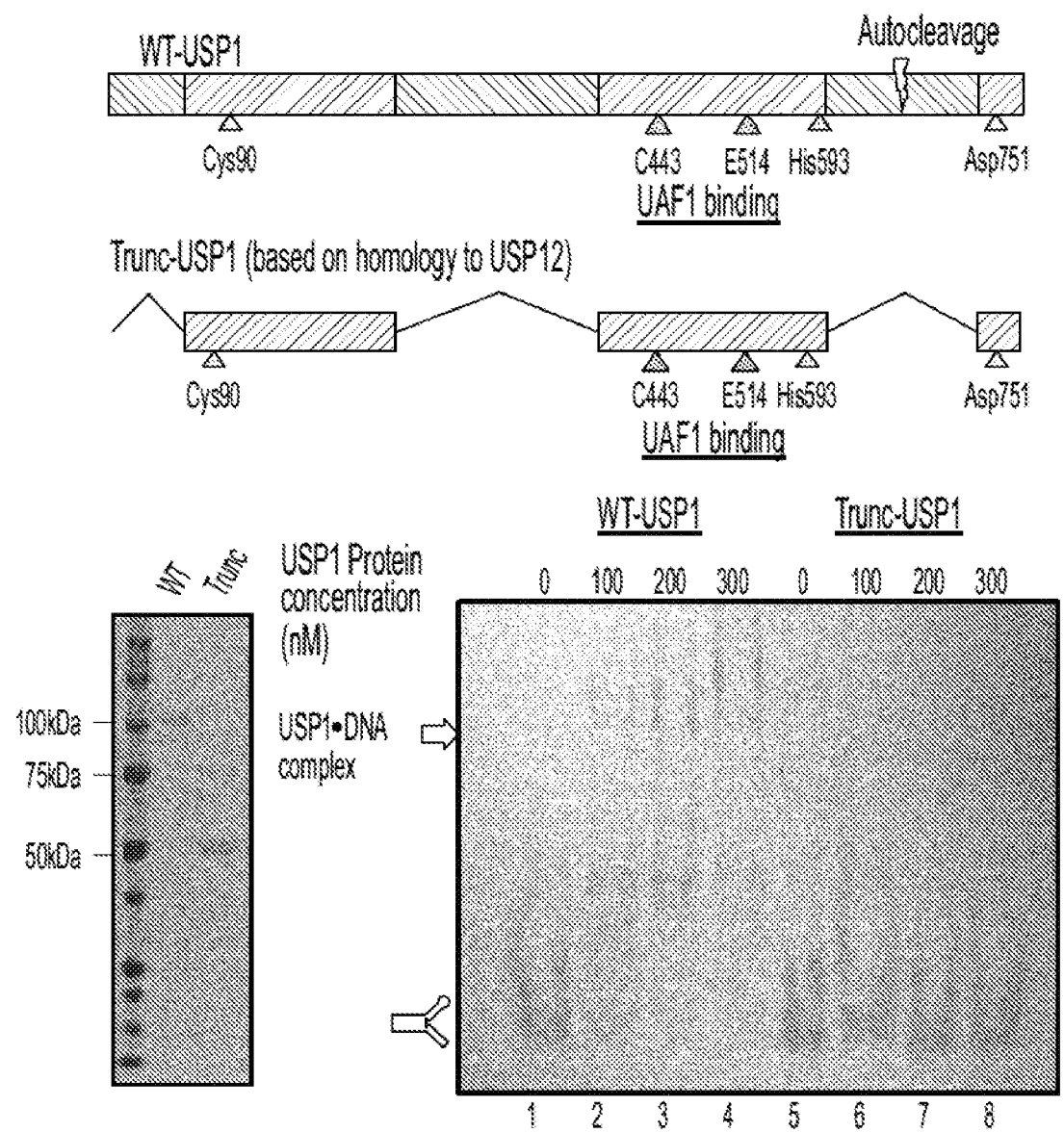
FIG. 3D. Schematic representation of WT-USP1 and Trunc-USP1 (top). Coomassie gel of WT-USP1 and Trunc-USP1 (bottom left) and electromobility shift gel of 0-200 nM of WT-USP1 (lanes 1-6) and 0-200 nM of Trunc-USP1 (lanes 7-12) (bottom right).

Through the analysis of sequence alignment between USP1 and USP12, the cDNA encoding a truncated form of USP1 (USP1-Trunc) was generated. The cDNA was designed to eliminate regions of USP1 that are not conserved with USP12 (FIG. 3D). USP1-Trunc still contains the critical Cys, His, and Asp residues, known to comprise the catalytic triad of the active ubiquitin protease (33). USP1-Trunc also contains the two critical amino acids (Cys 443 and Glu 514), required for binding and activation by UAF1 (23, 24). USP1-Trunc does not contain the autocleavage site, previously identified in full length USP1 (34). As predicted, USP1-Trunc failed to bind and gel shift the fork DNA structure (FIG. 3D, lanes 5-8), confirming that the critical DNA binding regions of USP1 exist within the deleted amino acid sequences.

Figure 16A:
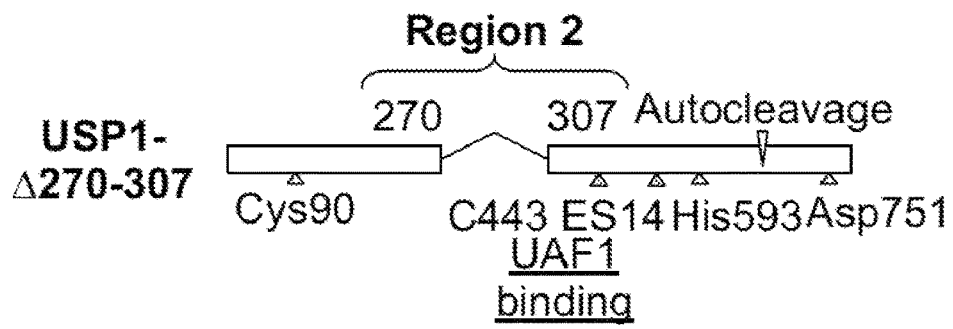
FIG. 16A. Schematic representation of USP1-4270-307 mutant showing deletion in region 2 of USP1.
Figure 16B:
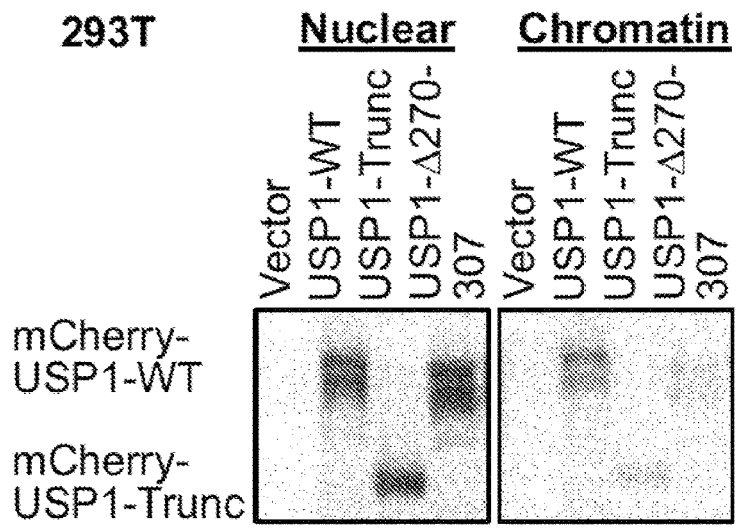
FIG. 16B. Chromatin fractionation of the lysates from 293T cells transfected with vector, mCherry-USP1-WT and mCherry-USP1-Trunc and mCherry-USP1-4270-307 showing reduced localization of USP1-4270-307 and USP1-trunc to the chromatin.

To further map the DNA binding domain of USP1, USP1 mutant proteins were evaluated using a chromatin binding assay (FIG. 16A). USP1-WT bound to chromatin; however, USP1-Trunc and USP1-Δ270-307 mutants had reduced binding to chromatin (FIG. 16B). Region 2 of USP1, from amino acid 270 to 307, also deleted in USP1-Trunc, was required for DNA binding, and critical lysine residues in this region were required.

USP12 and USP46 are known to interact with both UAF1 and an additional WD40 containing protein, $WDR_{20}$ (21, 35). Since USP1 is a larger protein and contains a DNA binding domain, the combination of USP1 sequences and DNA may substitute for the $WDR_{20}$ subunit in the assembled USP1/UAF1 complex (FIG. 10B).

Example 4

The Deubiquitinating Activity of USP1 is Stimulated by DNA Binding

Since USP1 is a deubiquitinase that has DNA binding activity, it is plausible that DNA might act as a cofactor, altering its deubiquitinating activity. Experiments were performed to examine the ubiquitin protease activity of full length USP1 bound in a complex with UAF1 with or without DNA, using the ubiquitin-AMC release assay and the ubiquitin CHOP2 assay (20, 31, 35, 36). DNA stimulated a time-dependent increase in DUB activity (FIG. 4A). Maximal DUB stimulation was achieved with fork DNA, consistent with the stronger USP1 binding activity for this template. Double strand DNA also generated maximal DUB stimulation (FIG. 4B). Fork DNA increased the DUB activity of the USP1/UAF1 complex at a 1:1 stoichiometry, with no further increase in DUB activity with additional DNA (FIG. 4C).

In contrast, DNA did not stimulate the activity of USP12, consistent with the lack of DNA binding activity of USP12

Figure 4D:
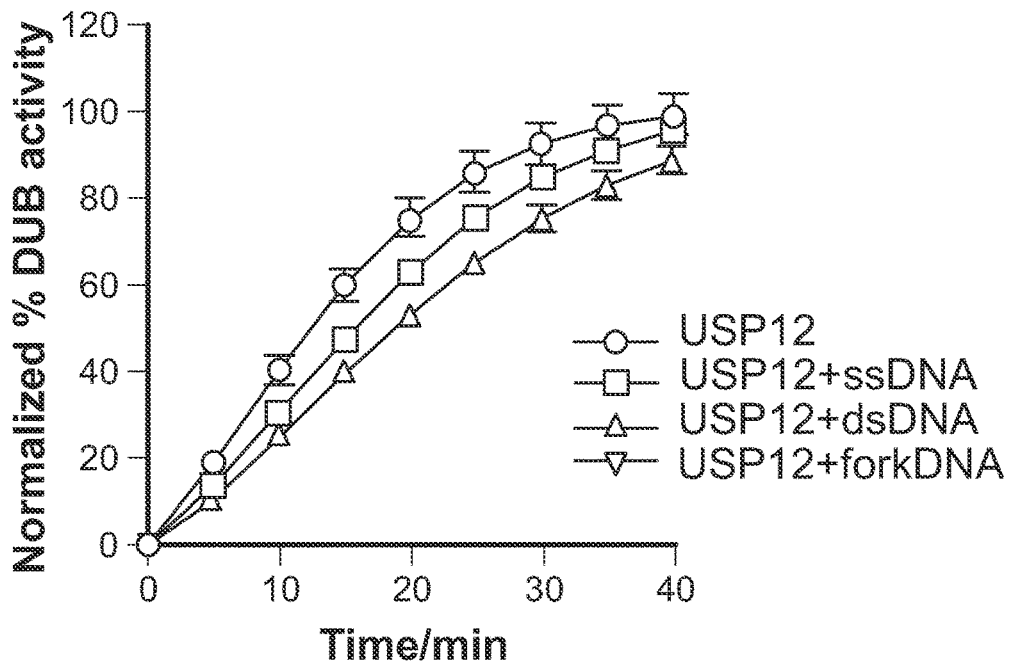
FIG. 4D. Ub-CHOP2 assay measuring WT-USP12/UAF1/WDR$_{20}$ deubiquitination activity with no DNA, ssDNA, dsDNA and fork DNA.
Figure 4E:
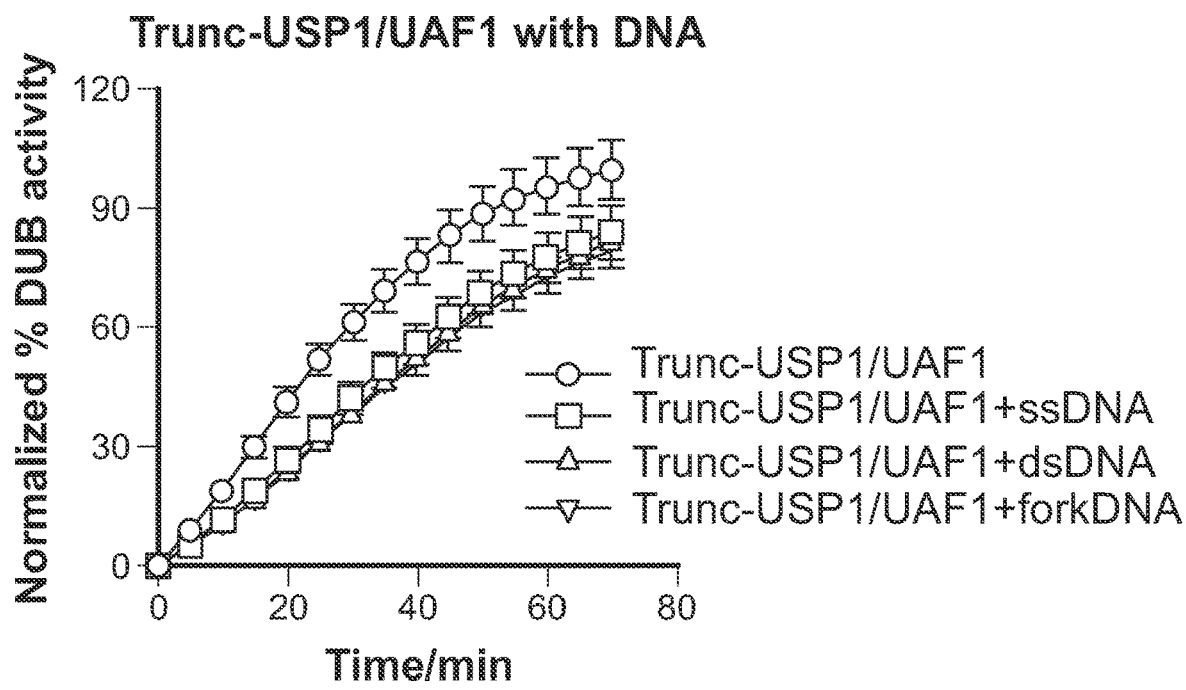
FIG. 4E. Ub-CHOP2 assay measuring Trunc-USP1/UAF1 deubiquitination activity with no DNA, ssDNA, dsDNA and fork DNA.
Figures 11A, 11B:
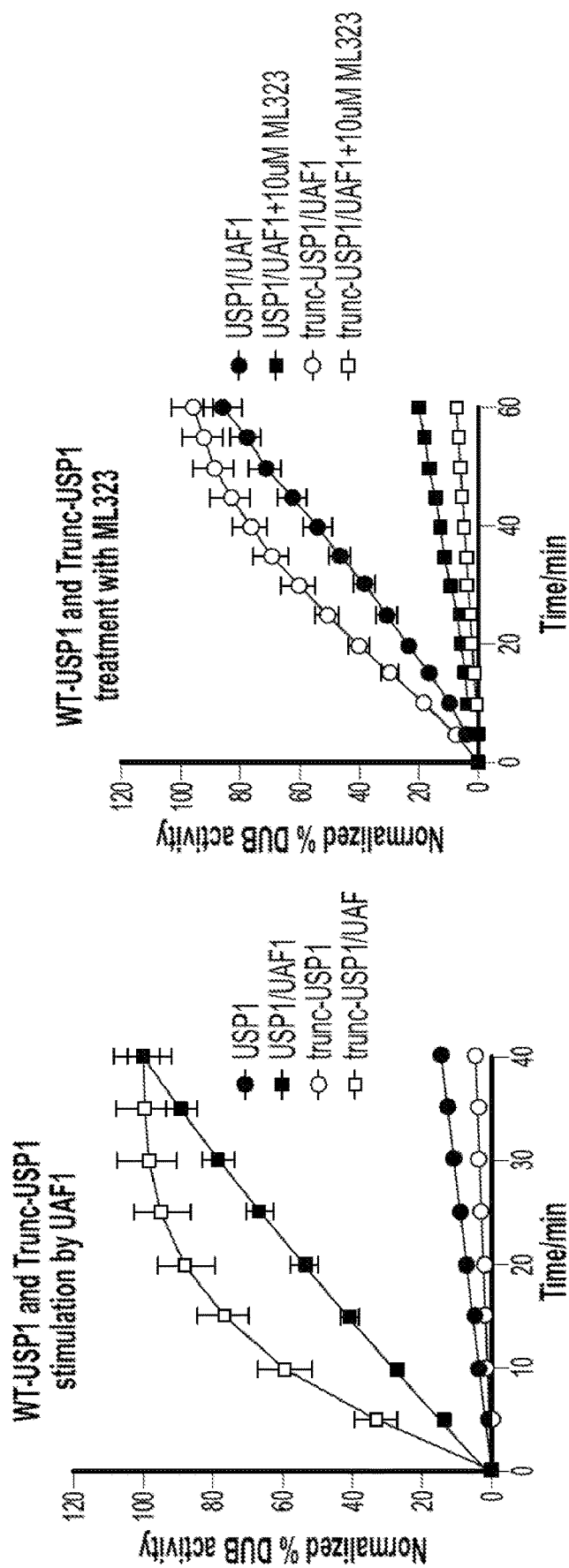
FIG. 11A. Ub-CHOP2 assay of WT-USP1 and Trunc-USP1 activity with and without UAF1.
FIG. 11B. Ub-CHOP2 assay of WT-USP1 and Trunc-USP1 with and without USP1 inhibitor ML323.

(FIG. 4D). UAF1 stimulated the DUB activity of USP1-Trunc, consistent with the presence of both the DUB catalytic triad and the UAF1 interaction domain of USP1-Trunc (FIG. 4E and FIG. 11A). Interestingly, DNA failed to stimulate the DUB activity of the USP1-Trunc/UAF1 complex (FIG. 4E), indicating that the DNA binding activity of USP1 is required for DNA stimulated DUB activity. Since UAF1 has direct DNA binding activity, and the DNA binding site of UAF1 remains unknown, it is unclear whether DNA binding to UAF1 also contributes to DUB activity stimulation (26). However, the lack of DNA stimulation of the USP1-Trunc/UAF1 complex suggests that the DNA binding of UAF1 alone is insufficient to stimulate USP1 DUB activity, and the direct binding of USP1 to DNA is required.

Example 5

DNA Binding to USP1/UAF1 Enhances Ubiquitin Substrate Binding and Turnover

Figures 4F, 4G:
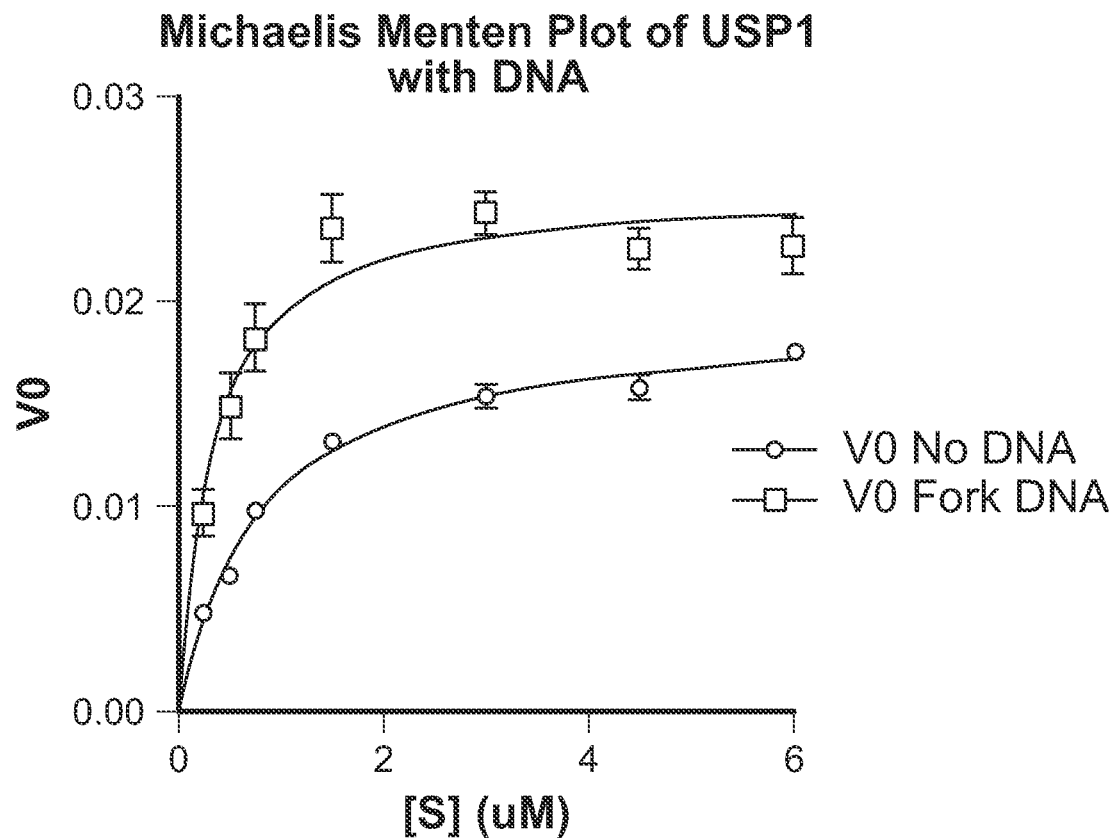
FIG. 4F. Michaelis-Menten plot of the deubiquitination activity of WT-USP1/UAF1 with fork DNA measured by the Ub-AMC deubiquitination assay.
FIG. 4G. The Km and kcat values obtained from the Michaelis-Menten plot. WT-USP1 and WT-UAF1 proteins were purchased from Boston Biochem while the USP12/UAF1/WDR$_{20}$ complex and Trunc-USP1 proteins were made in SF9 cells or E. Coli.

To gain further insight into the dynamics of USP1/UAF1 activation by DNA, the kinetics of complex activation were investigated. An in vitro enzymatic assay of the purified USP1/UAF1 complex, using Ub-AMC as a substrate, was established (FIGS. 4F, 4G). In order to determine the kinetic parameters of the USP1/UAF1 complex alone compared to the USP1/UAF1/fork DNA complex, the deubiquitination reaction was performed with a limiting amount of enzyme and an excess of substrate, and the initial velocity Vo was obtained. By measuring the substrate conversion at increasing substrate concentrations (FIG. 4F), it was determined that the affinity of the USP1/UAF1 complex for its ubiquitinated substrate is modestly influenced by DNA binding, decreasing the $K_m$ from 0.79 µM to 0.33 µM (FIG. 4G). Also, the catalytic turnover was modestly influenced by DNA binding, increasing the Kcat value 1.3 fold. As a result, the $k_{cat}/K_m$ ratio is 3-fold higher for the USP1/UAF1/DNA complex, compared to the USP1/UAF1 complex alone. Taken together, DNA regulates the activity of the USP1/UAF1 complex by increasing both substrate affinity and turnover.

Example 6

Figure 11C:
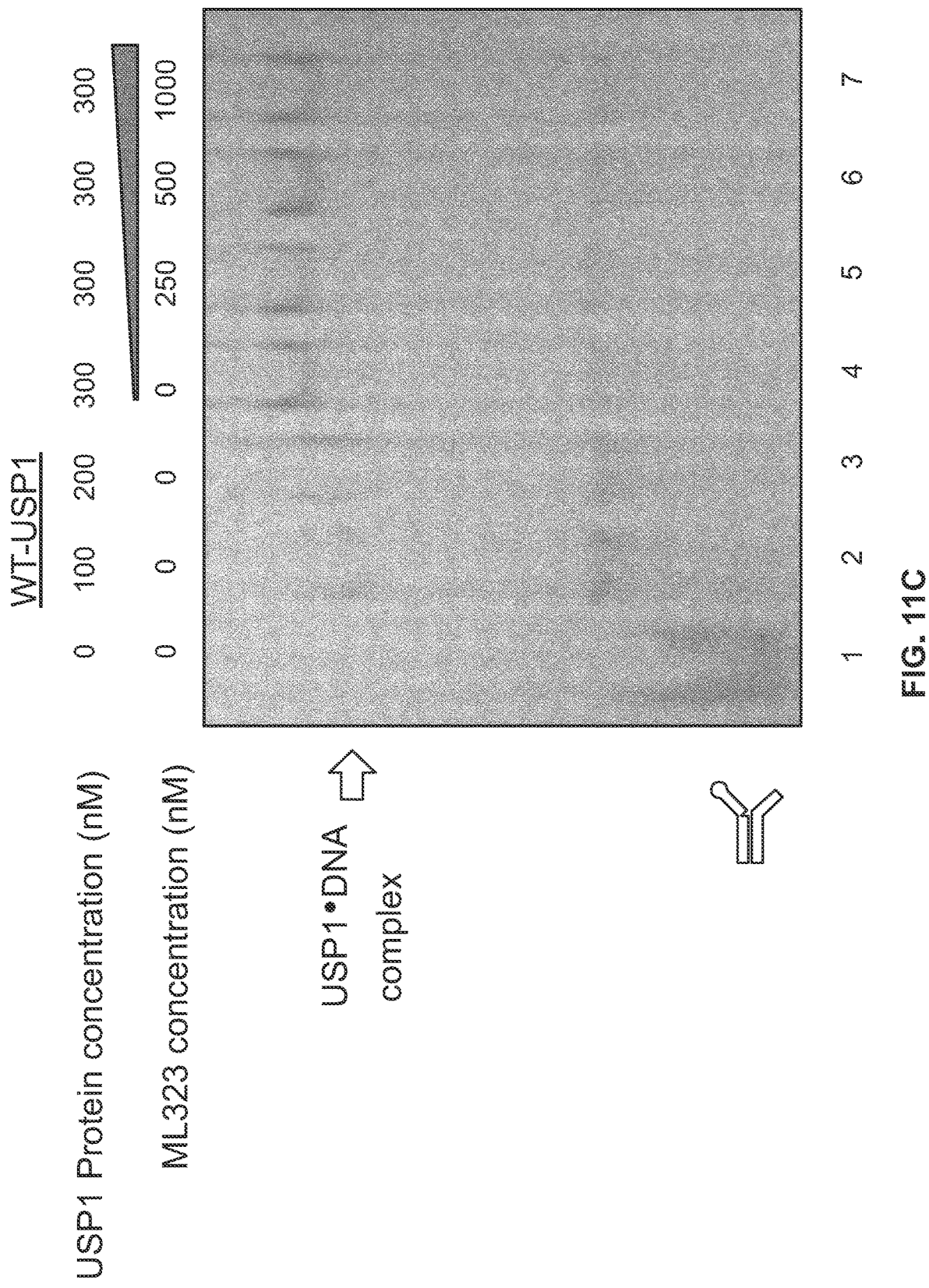
FIG. 11C. Electromobility shift assay of 0-300 nM of USP1 incubated with 0-1000 nM of ML323 and forked DNA.

Specific Inhibitor of USP1 (ML323) Inhibits the DUB Activity of USP1-Trunc but does not Inhibit DNA Binding A specific inhibitor of USP1 (ML323) was recently identified which blocks FANCD2 deubiquitination, causes an accumulation of cellular FANCD2-Ub, and causes cellular hypersensitivity to cisplatin (29). Although ML323 binds directly to USP1, the binding site has not been determined. Interestingly, ML323 inhibits USP1-Trunc, as well as wild-type, full-length USP1, indicating that the ML323 binding site(s) on USP1 are preserved in the USP1-Trunc protein (FIG. 11B). Moreover, ML323 binding does not interfere with the DNA binding activity of full-length USP1 (FIG. 11C). Taken together, the inhibitory activity of ML323 does not result from the inhibition of DNA binding to USP1.

Example 7

Usp1/Uaf1 DNA Binding Activity is Required for Localization of the DUB complex to the replication fork Recent studies suggest that the USP1/UAF1 complex might play a regulatory role at the advancing replication fork by controlling the local level of critical ubiquitinated substrates. Using the iPOND mass spectrometry, Dungrawala et. al identified USP1, UAF1 (WDR48), PCNA, and the FANCI/FANCD2 complex (ID complex) at sites of nascent DNA (27). Interestingly, the USP1/UAF1 complex traveled with the elongating replication fork, but was displaced following fork stalling with hydroxyurea. Another study, comparing the relative abundance of USPs on nascent and mature chromatin by iPOND, also identified USP1 enrichment at the replisome (37). These studies suggest that USP1 may contribute to replication fork protection. Other studies demonstrate that replication stress causes USP1 autocleavage, suggesting a plausible mechanism for the regulated release of USP1/UAF1 from the fork (34).

Figure 5A:
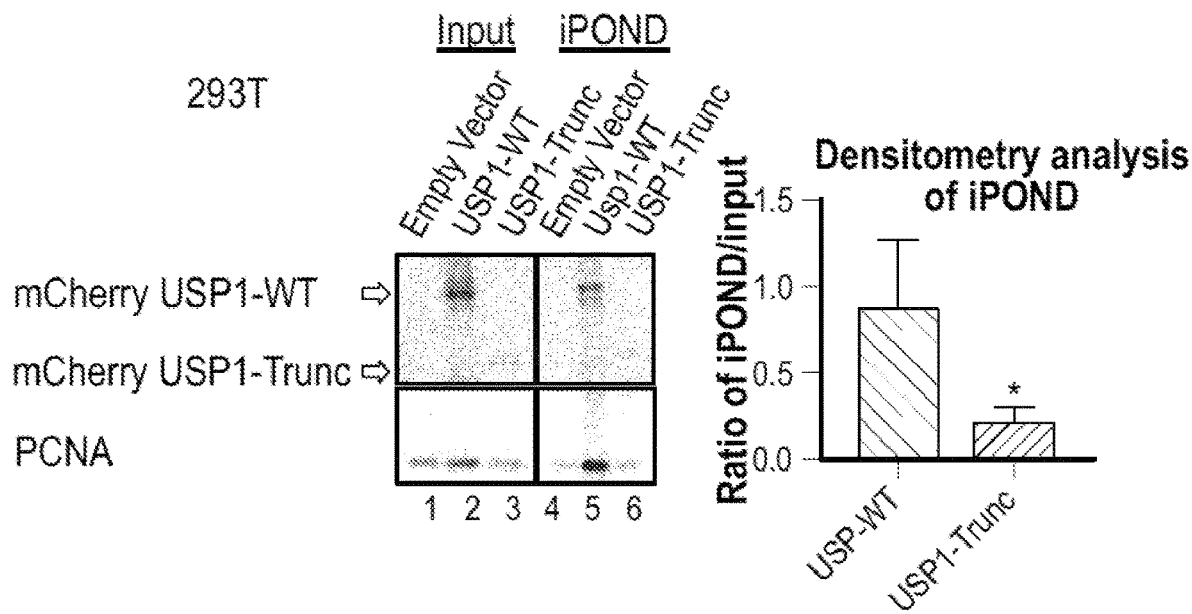
FIG. 5A. Left: iPOND blot of 293T cells transfected with either vector control, mCherry tagged WT-USP1 or Trunc-USP1 and probed with antibody against mCherry and PCNA. Right: Densitometry analysis of the iPOND blot.

Experiments were performed to confirm that USP1 localizes to the replication fork, by using iPOND (38). Since USP1-Trunc fails to bind DNA, it was reasoned that it would also fail to localize to the replication fork. Using transient transfections of mCherry-USP1-WT or mCherry-USP1-Trunc in 293T cells, replication fork proteins were enriched using iPOND and a western blot was performed (FIG. 5A). As predicted, USP1-Trunc failed to localize to the replication fork, indicating that DNA binding is required for USP1 fork localization (FIG. 5A, lane 6).

Figure 17:
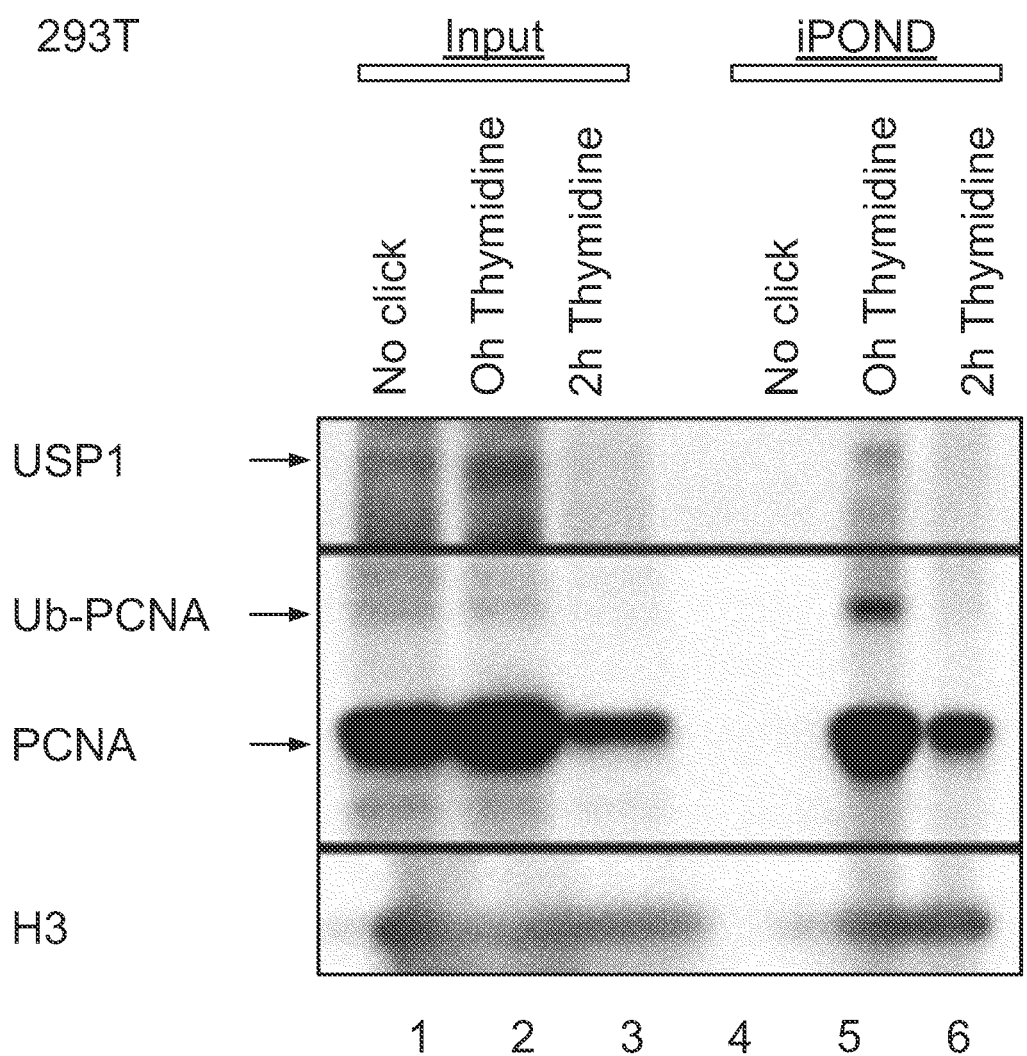
FIG. 17. iPOND blot with thymidine chase showing USP1 and PCNA decreasing at the replication fork following a 2 h treatment with thymidine.
Figures 21A, 21B:
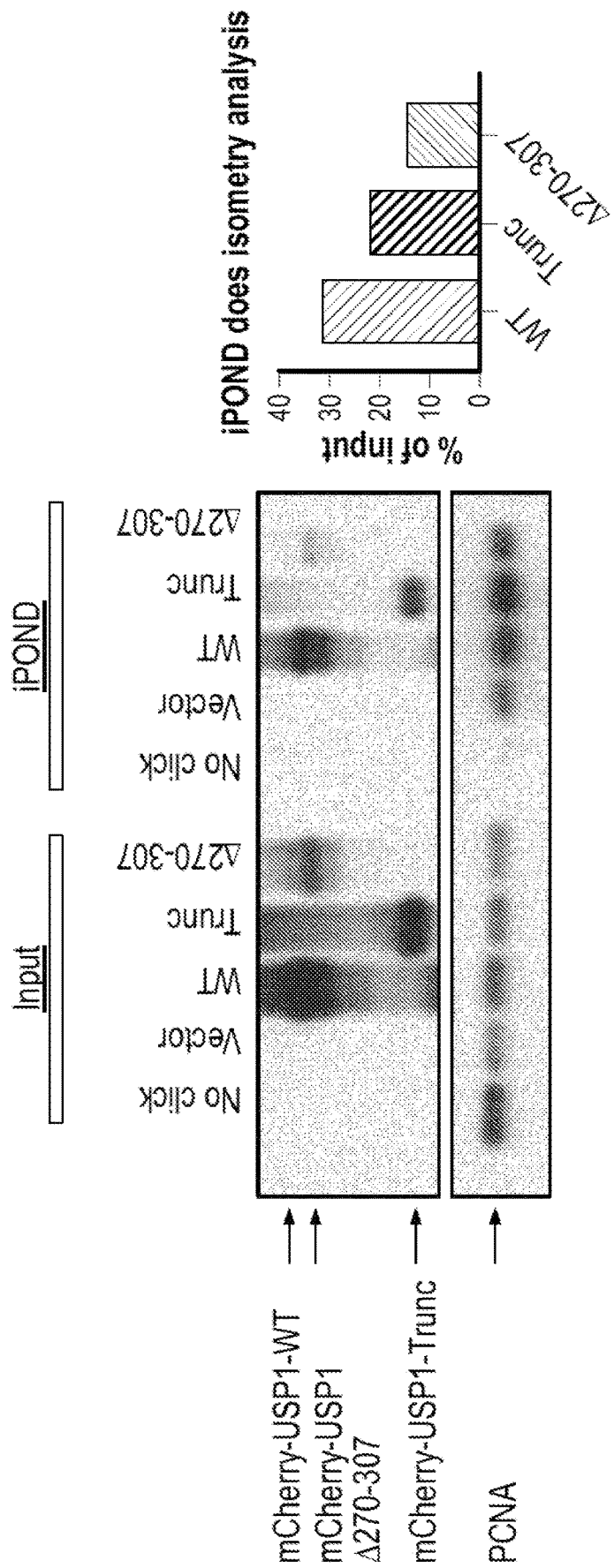
FIG. 21A. iPOND blot of 293T cells transfected with either vector control, mCherry tagged WT-USP1, Trunc-USP1 or USP1-4270-307 and probed with antibody against mCherry and PCNA.
FIG. 21B. Densitometry analysis of the iPOND blot.

Replication fork proteins were also enriched by iPOND and identified by immunoblotting (FIG. 17). As expected, similar to PCNA, USP1 was pulled down with nascent DNA and disappeared following thymidine chase, suggesting that USP1 localizes to the replication fork (FIG. 17). Since USP1-Trunc fails to bind DNA, it was predicted that it would not localize to the replication fork. Using transient transfections of mCherry-USP1-WT or mCherry-USP1-Trunc in 293T cells, an iPOND experiment was performed followed by a western blot. As predicted, WT-USP1, but not USP1-Trunc, localized to the replication fork, indicating that DNA binding is required for USP1 fork localization. PCNA localization was also found at the replication fork, as expected. The USP1-Δ270-307 mutant, with defective DNA binding activity, also showed reduced localization to the replication fork (FIGS. 21A-21B).

Example 8

Figure 5B:
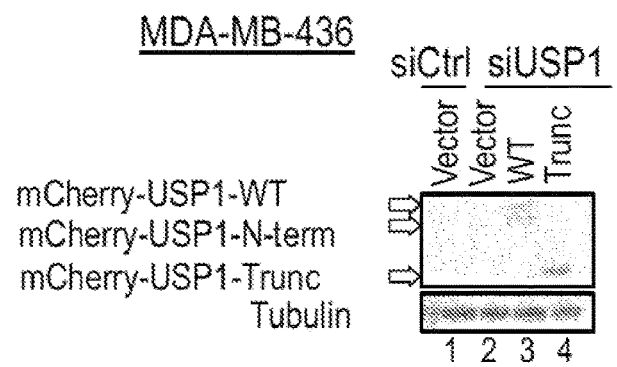
FIG. 5B. Western blot showing BRCA1-deficient MDA-MB-436 cells treated with siCtrl or siUSP1 and rescued with either empty vector, WT-USP1 or USP1-Trunc.
Figure 5C:
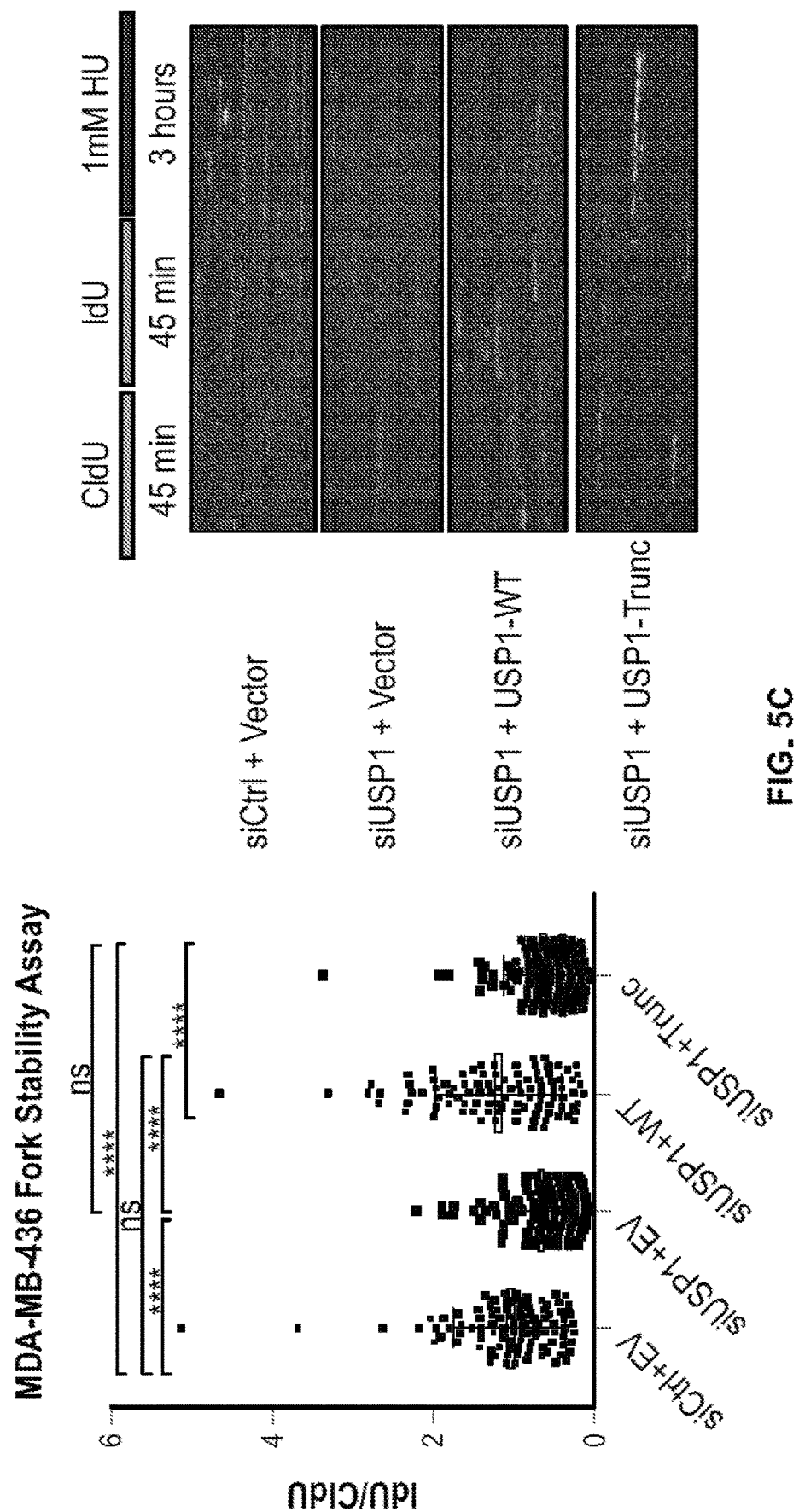
FIG. 5C. Left: Graphical quantification of a fiber experiment measuring hydroxyurea mediated replication fork instability in BRCA1 deficient cells following treatment with siCtrl or siUSP1 and rescued with either empty vector, WT-USP1 or USP1-Trunc. Right: Schematic of CldU, IdU and HU treatment (top), and representative fibers from each treatment condition (bottom).

DNA Binding Activity of USP1 is Required for Fork Protection and Cell Survival in BRCA1 Deficient Cells Since the DNA binding activity of USP1 is required for its replication fork localization, experiments were performed to test its role in fork protection in BRCA1 deficient cells. Knockdown of USP1 in BRCA1 deficient MDA-MB-436 cells destabilized the replication fork after hydroxyurea blockade (FIGS. 5B and 5C). Complementation with wild-type USP1, but not the DNA binding mutant, USP1-Trunc, restored normal replication fork stability (FIGS. 5B and 5C).

Figure 21C:
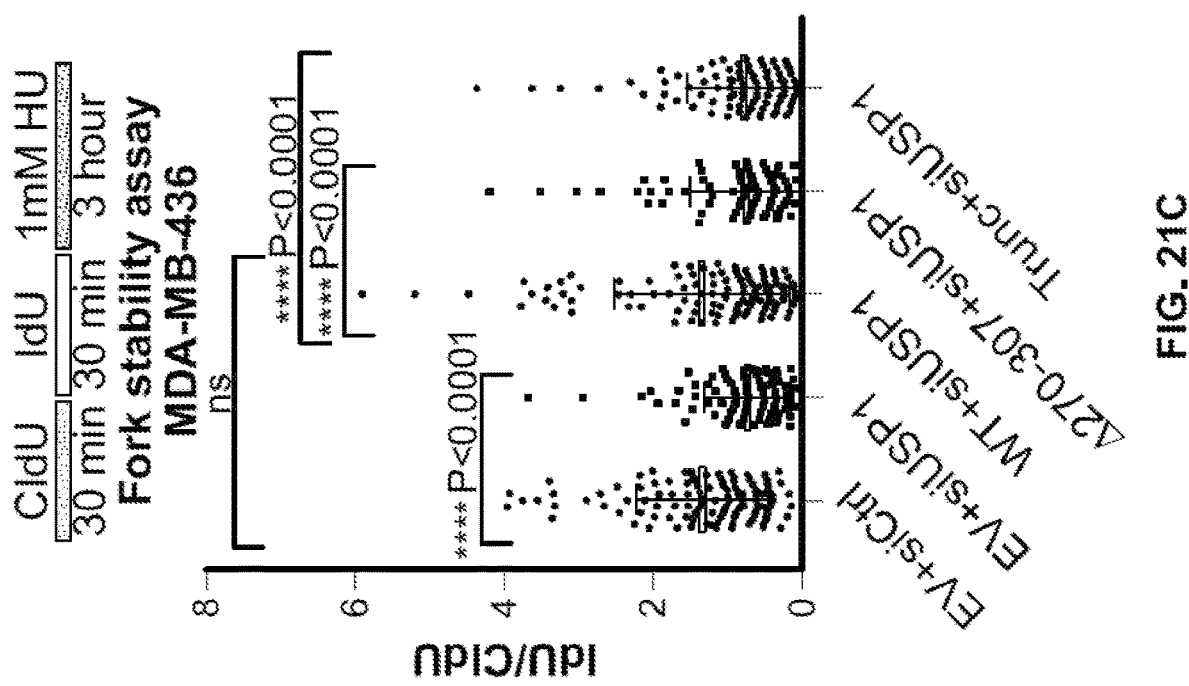
FIG. 21C. Schematic of the experimental design for the fiber assay and graphical quantification of a fiber assay measuring hydroxyurea (HU) mediated replication fork instability in BRCA1 deficient MDA-MB-436 cells following treatment with siCtrl or siUSP1 and rescued with either empty vector, WT-USP1, 4270-307-USP1 or USP1-Trunc.

USP1-Δ270-307 mutant also failed to rescue the replication fork instability in BRCA1 deficient cells following USP1 silencing (FIG. 21C).

Figure 5D:
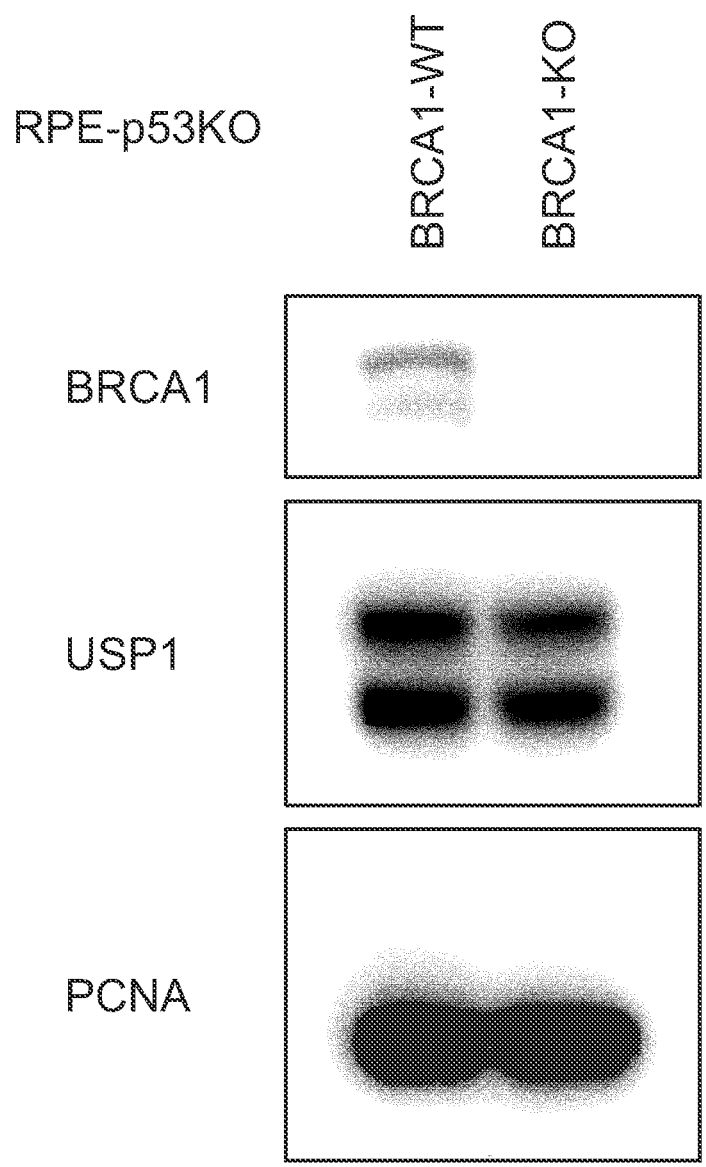
FIG. 5D. Western blot confirmation of BRCA1 loss in p53 deficient RPE cells.
Figures 12A, 12B:
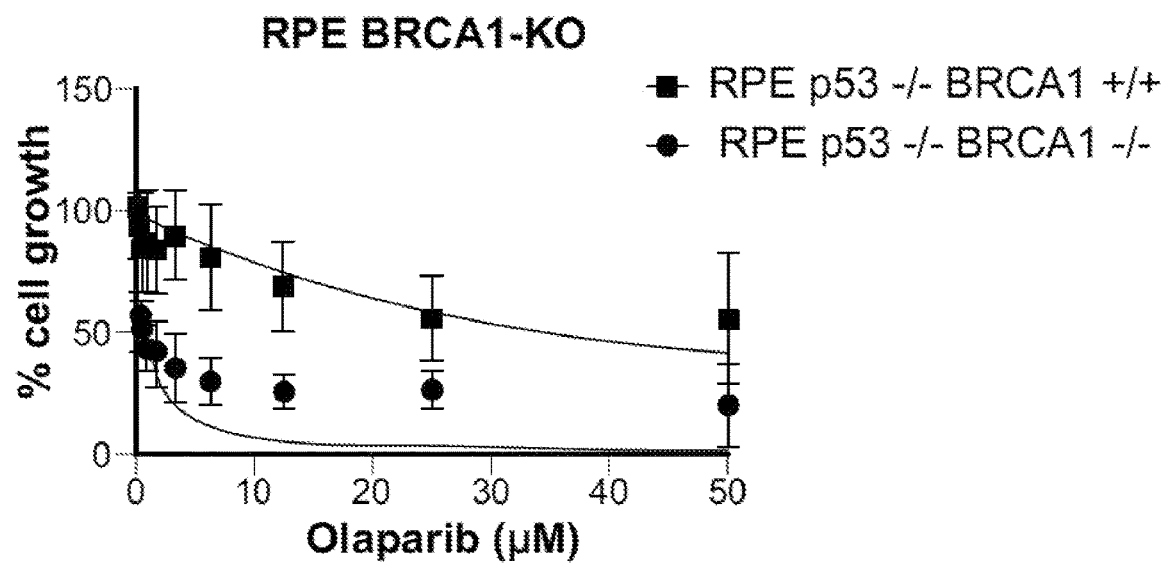
FIG. 12A. Sequencing results showing the introduction of a stop codon in exon 3 in both alleles of BRCA1 in p53 deficient RPE cells.
FIG. 12B. Cytotoxicity curve of p53 deficient RPE cells with and without BRCA1 following Olaparib treatment.

In order to confirm this finding in a null genetic background, a genomic knockout of BRCA1 was preformed using CRISPR-Cas9 in normal retinal pigment epithelial (RPE) cells. TP53 was first knocked out by CRISPR-Cas9, and a single cell subclone was generated. Subsequently, BRCA1 was knocked out by CRISPR-Cas9, and a p53−/−, BRCA1−/− RPE subclone was identified. This clone is both p53 and BRCA1 deficient with no other known genetic aberrations (FIGS. 5D and 12A). The p53−/−, BRCA1−/−

RPE cells were highly sensitive to PARP inhibitor treatment, while p53−/−, BRCA1+/+ cells were resistant (FIG. 12B).

Figure 5E:
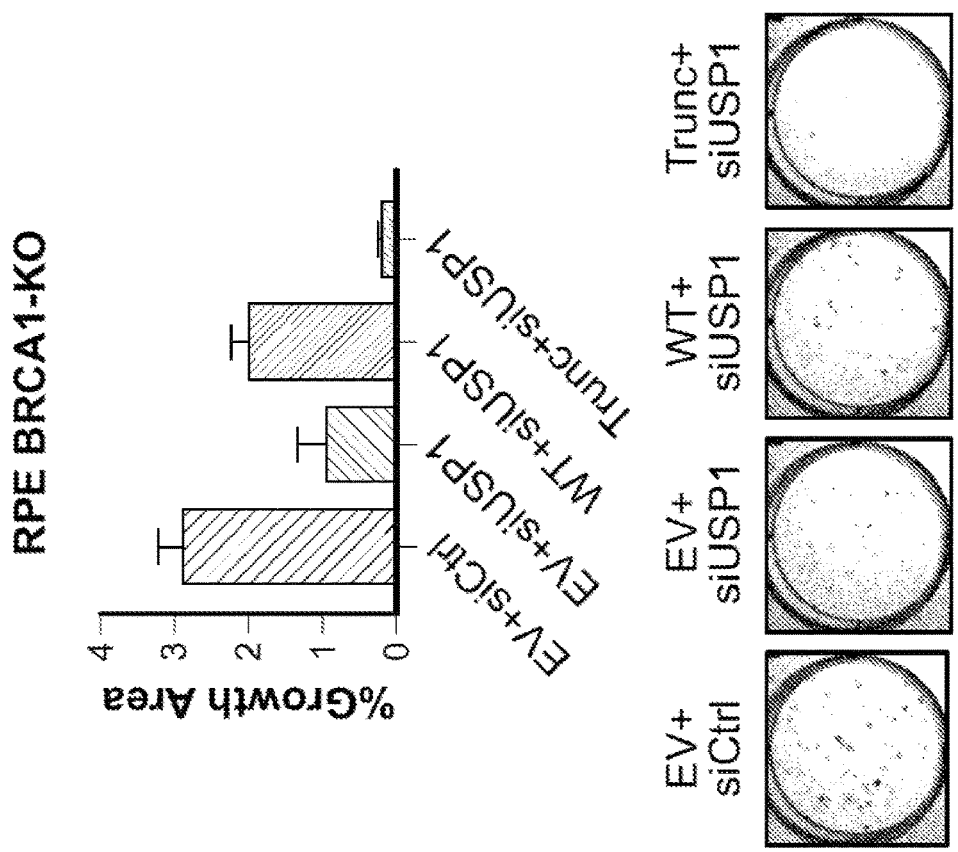
FIG. 5E. Left: Western blot of BRCA1 deficient RPE cells treated with siCtrl or siUSP1 and rescued with either empty vector, WT-USP1 or USP1-Trunc. Right: Graphical quantification of a colony formation assay in BRCA1 deficient RPE cells transfected with siCtrl or siUSP1 and complemented with either empty vector, WT-USP1 or USP1-Trunc (top) and representative colonies (bottom).
Figure 5E:
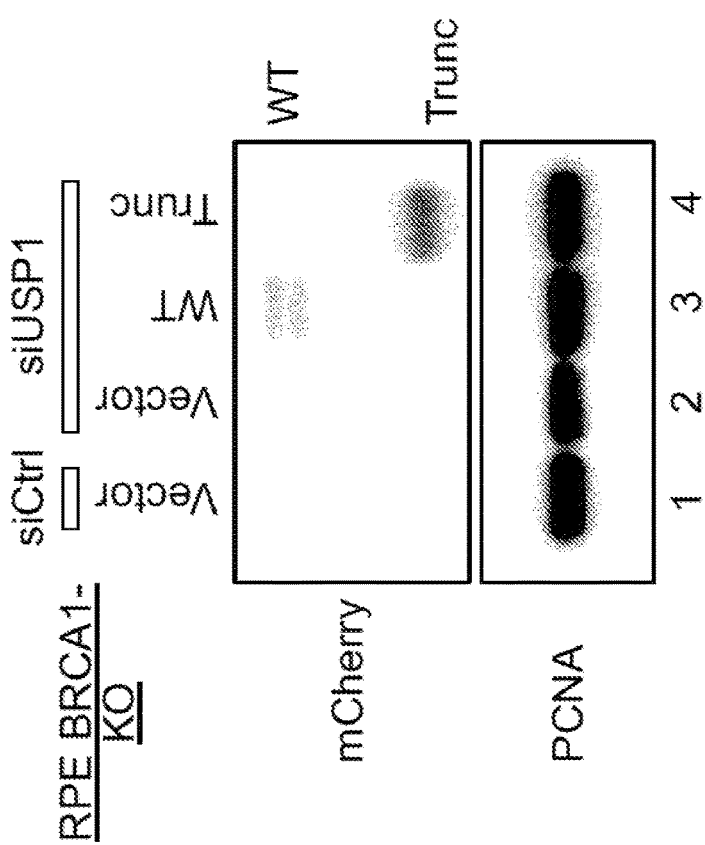

Silencing of USP1 inhibited the growth of BRCA1-deficient RPE cells, as expected. Transfection with the WT-USP1 cDNA, but not the Trunc-USP1 cDNA, rescued the growth defect, suggesting that the DNA binding function of USP1 is required for the growth and survival of BRCA1-deficient RPE cells (FIG. 5E). Similar results were obtained with BRCA1-deficient MDA-MB-436 cells.

Example 9

Silencing of Rad18 and POLK Rescued the Growth Defects in BRCA1 Deficient Cells Following USP1 Silencing Since USP1 is a deubiquitinase with at least two known replication fork proteins as its substrates (i.e., FANCD2-Ub and PCNA-Ub), it was reasoned that persistent ubiquitination of these substrates following USP1 inhibition may contribute to the replication fork instability. FANCD2, one of the best studied substrates of USP1, is required for replication fork stabilization in BRCA1/2 deficient cells. Therefore, it appeared to be the most likely candidate. However, silencing FANCA, a critical component of the Fanconi core complex important in FANCD2 ubiquitination, did not rescue for USP1 sensitivity in BRCA1 deficient cells.

Figure 6A:
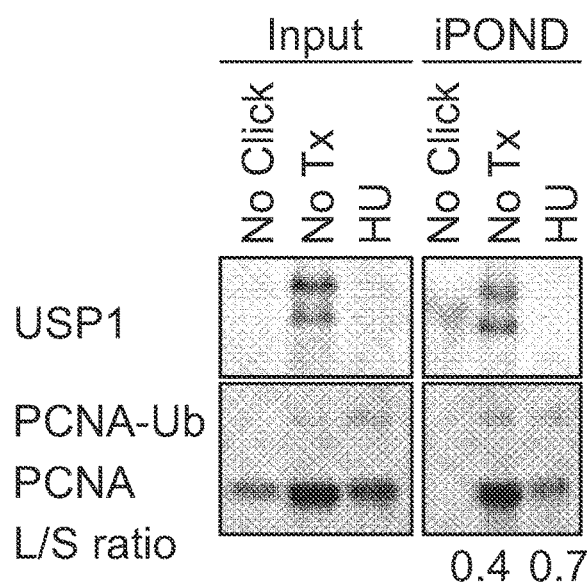
FIG. 6A. iPOND blot of 293T cells looking at USP1 levels and ub-PCNA levels following hydroxyurea treatment. The L/S ratio for PCNA is shown below the blot.
Figure 6B:
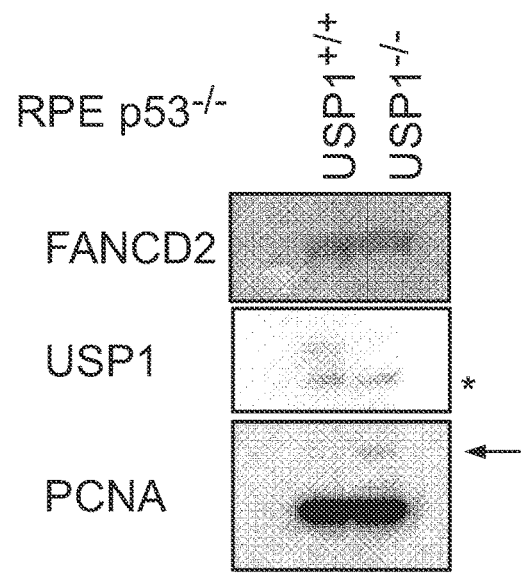
FIG. 6B. Western blot of RPE cells with CRISPR-mediated knockout of USP1. Monoubiquitination of both FANCD2 and PCNA is seen in the USP1$^{-/-}$ cells.
Figure 6C:
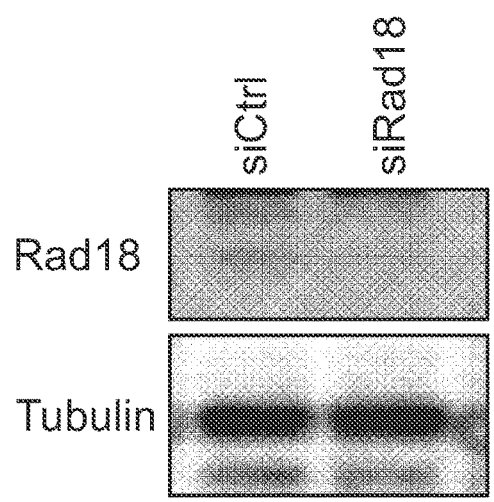
FIG. 6C. Western blot of UWB1.289 cells following Rad18 silencing.
Figure 6D:
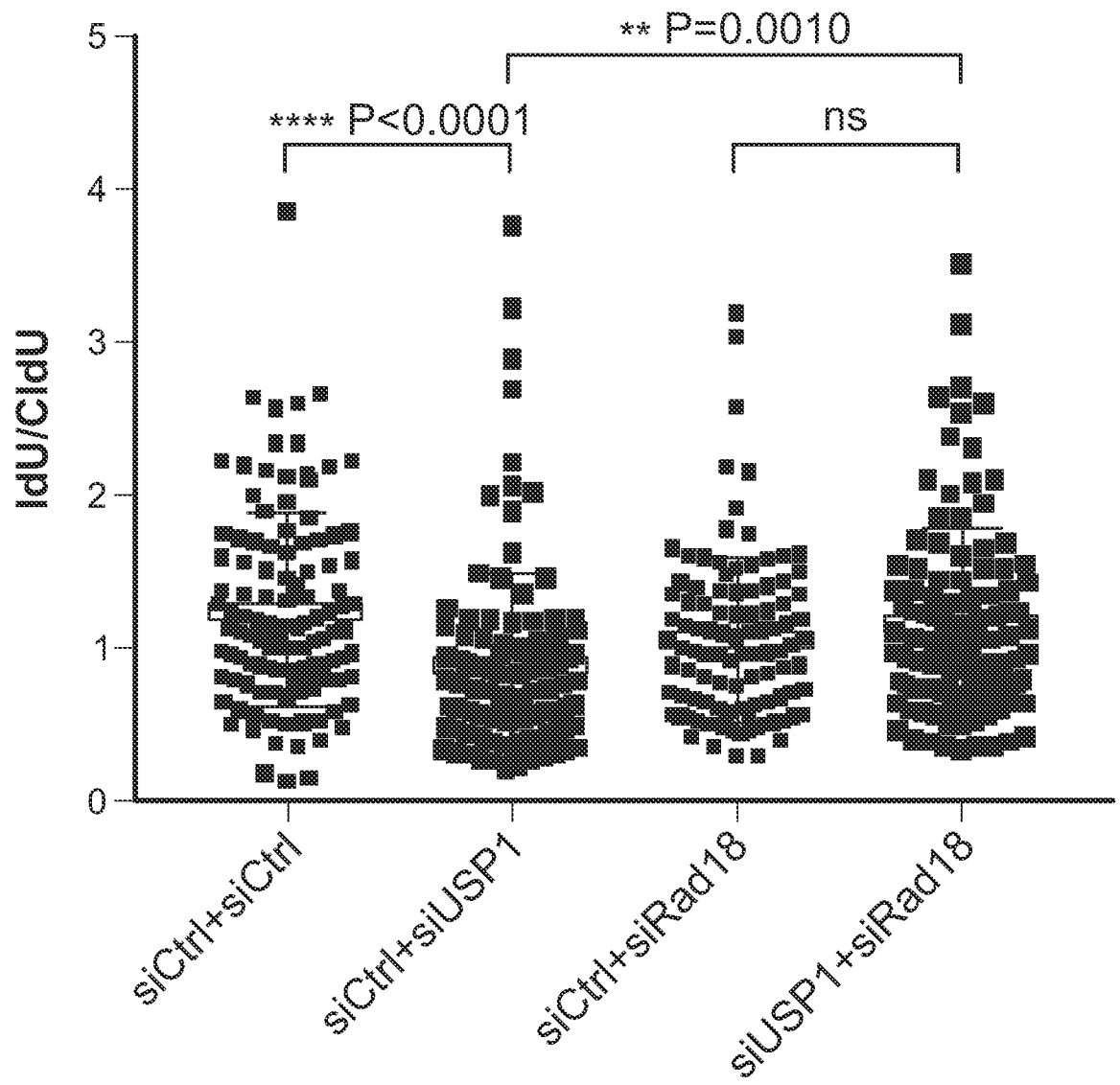
FIG. 6D. Graphical quantification of a fiber assay in UWB1.289 cells following treatment with siCtrl, siUSP1, siRad18 or siUSP1 and siRad18.
Figure 6E:
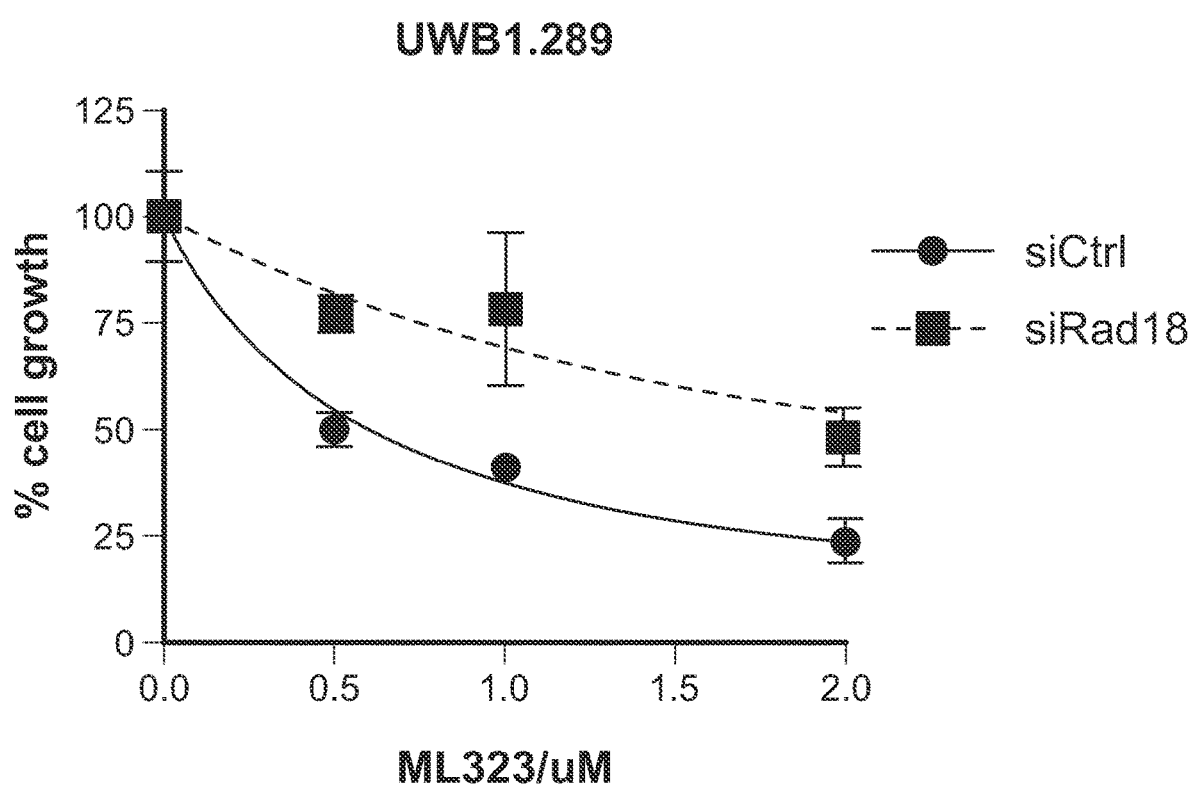
FIG. 6E. Dose response curve of UWB1.289 cells following Rad18 silencing and treatment with USP1 inhibitor ML323.

Monoubiquitinated PCNA increased at the replication fork following hydroxyurea mediated fork stalling, corresponding to the decrease in local USP1 (FIG. 6A).

Figure 22A:
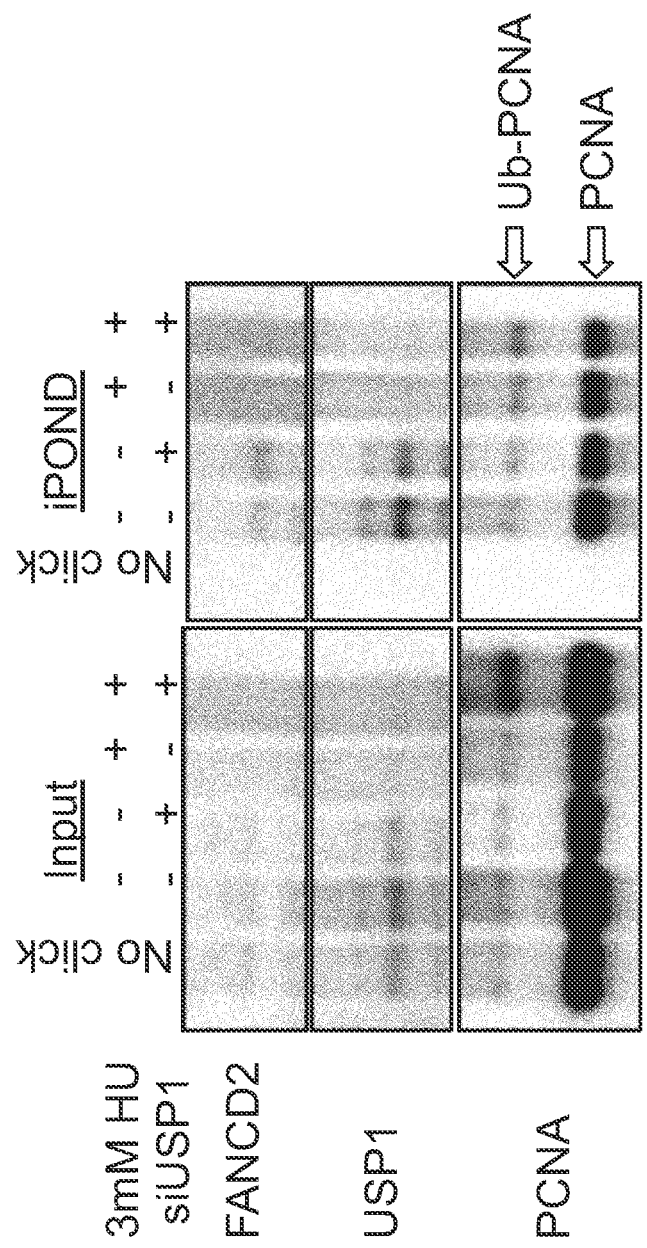
FIG. 22A. iPOND blot of hydroxyurea (HU)-treated 293T cells with siRNA-mediated knockdown of USP1. Note that loss of USP1 results in increased accumulation of PCNA-Ub at the stalled fork.
Figure 22B:
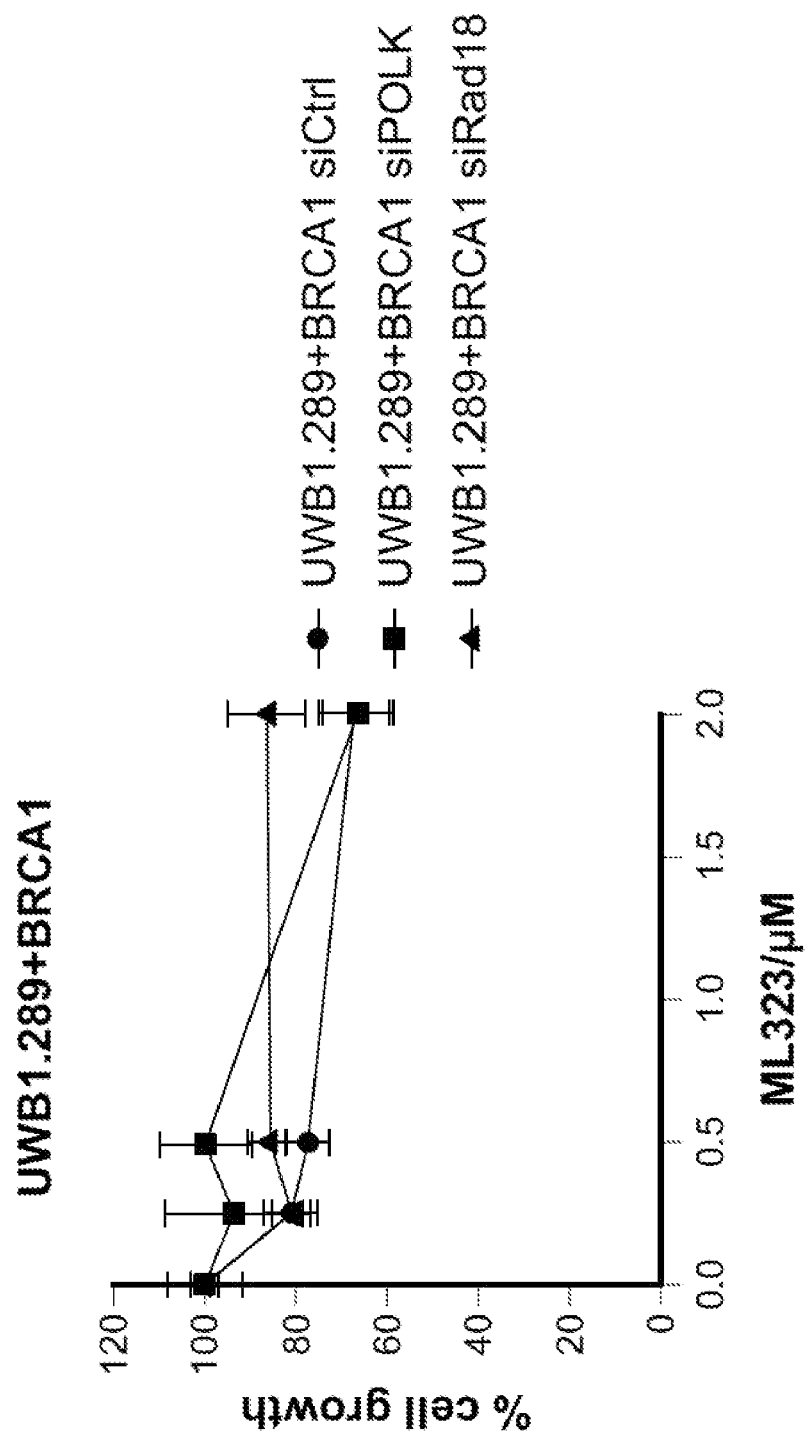
FIG. 22B. Growth curve of UWB1.289+BRCA1 cells with knockdown of POLK or RAD18.

As expected, PCNA-Ub levels increased after CRISPR-mediated knockout of USP1 or UAF1 in RPE-1 cells. An increase in PCNA-Ub, corresponding to a decrease in USP1, was observed after hydroxyurea treatment (FIG. 22A).

This result suggests that the timely deubiquitination of PCNA by USP1 is important for replication fork restart, and that the aberrant accumulation of monoubiquitinated PCNA and its substrates might lead to replication instability. Indeed, silencing RAD18, the monoubiquitin ligase for PCNA, rescued the replication fork instability and sensitivity in BRCA1 deficient cells following USP1 inhibition (FIGS. 6C-6E and 22B).

Figure 6F:
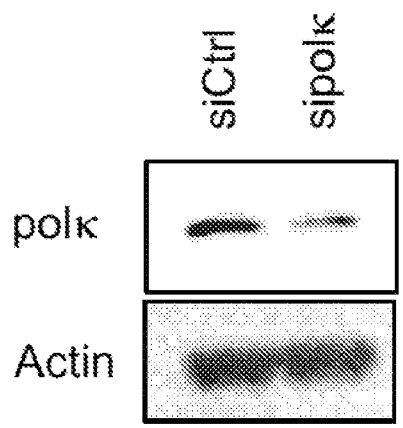
FIG. 6F. Western blot of UWB1.289 cells following POLK silencing.
Figure 6G:
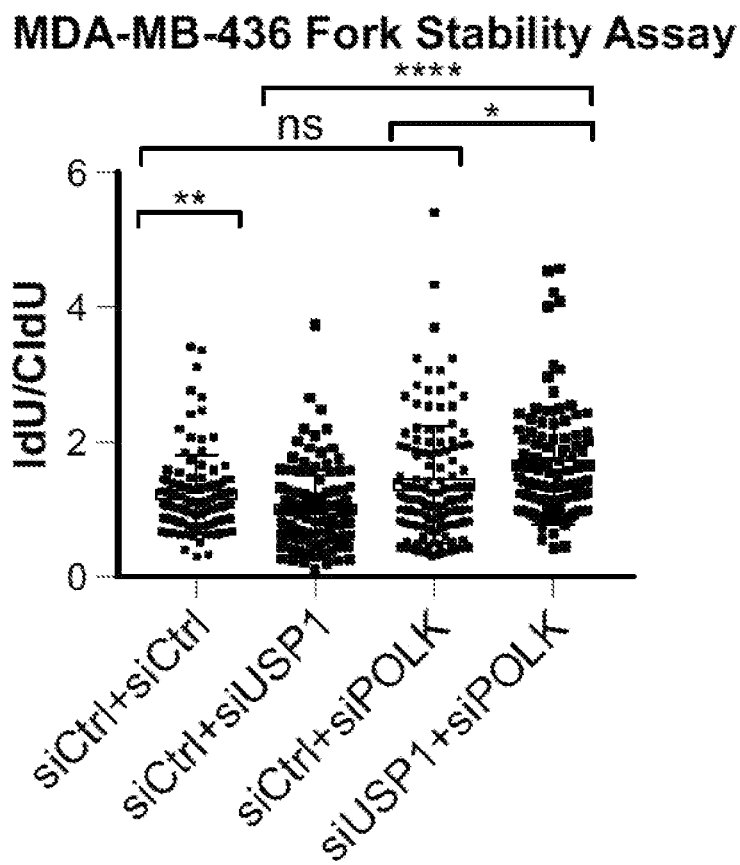
FIG. 6G. Graphical quantification of a fiber assay in MDA-MB-436 cells following treatment with siCtrl, siUSP1, siPOLK or siUSP1 and siPOLK.
Figure 6H:
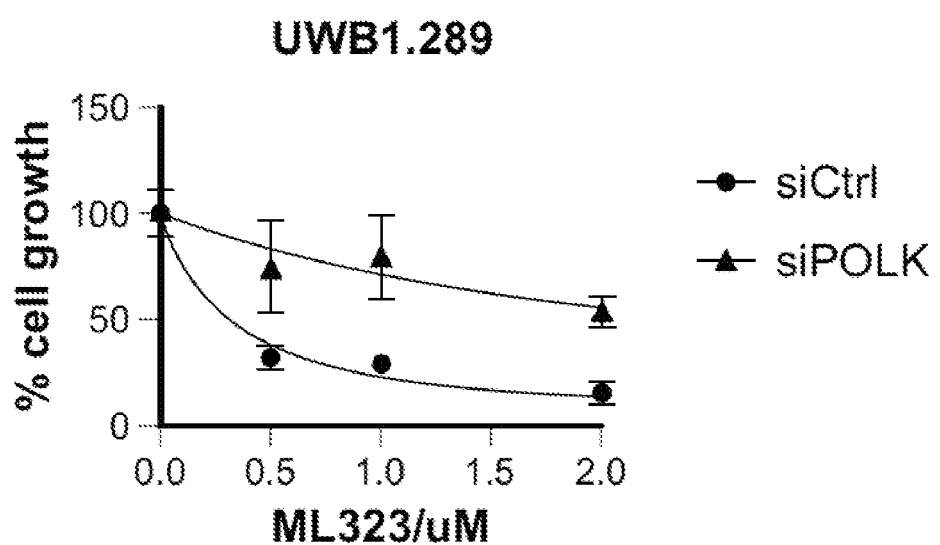
FIG. 6H. Dose response curve of UWB1.289 cells following POLK silencing and treatment with USP1 inhibitor ML323.
Figure 13A:
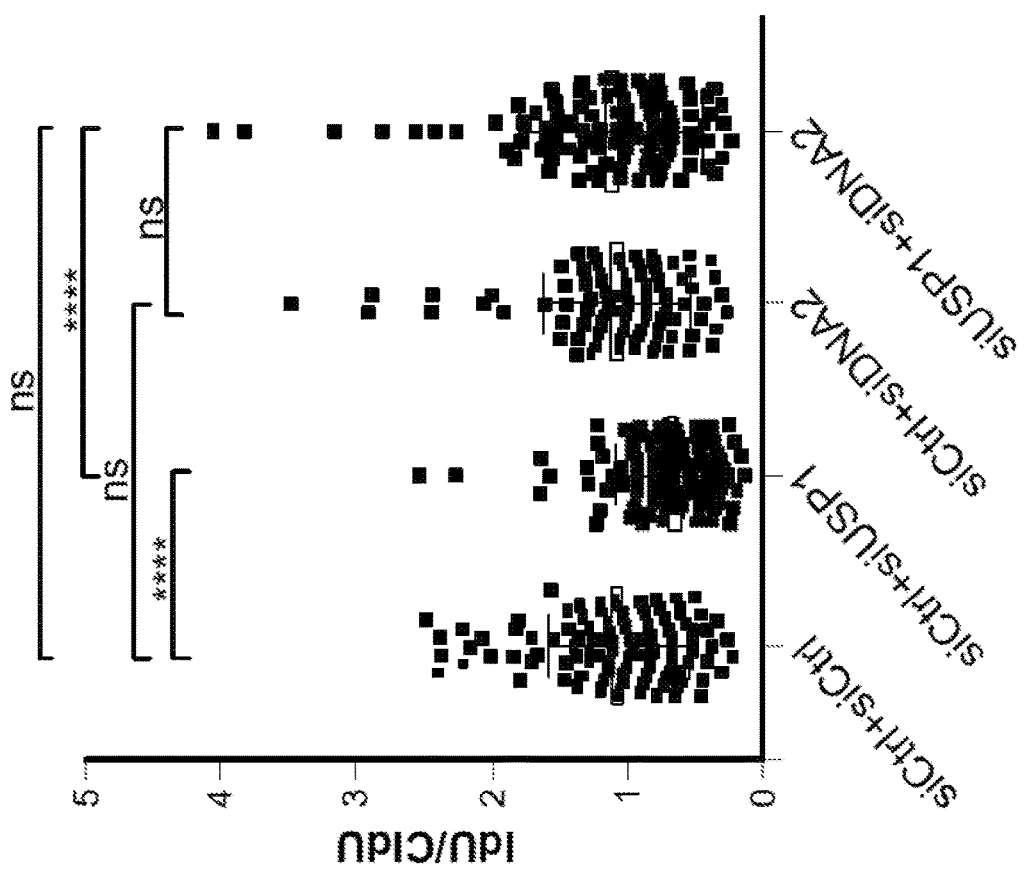
FIG. 13A. Graphical quantification of fiber assay in MDA-MB-436 cells following treatment with either siCtrl, siUSP1, siDNA2 or siUSP1 and siDNA2.

Aberrant POLK recruitment has previously been shown to slow replication forks in a USP1 dependent manner (39). Aberrant monoubiquitination of PCNA, leading to POLK recruitment, might therefore destabilize the replication fork in BRCA1 deficient cells. Indeed, silencing POLK rescued the replication fork instability and viability in these cells (FIGS. 6F-6H), thereby providing a mechanistic explanation of the toxicity resulting from USP1 knockdown. Silencing the nuclease DNA2 also rescued this phenotype, suggesting that DNA2 may also contribute to the destabilization of replication forks in the cells (FIG. 13A).

Figure 22C:
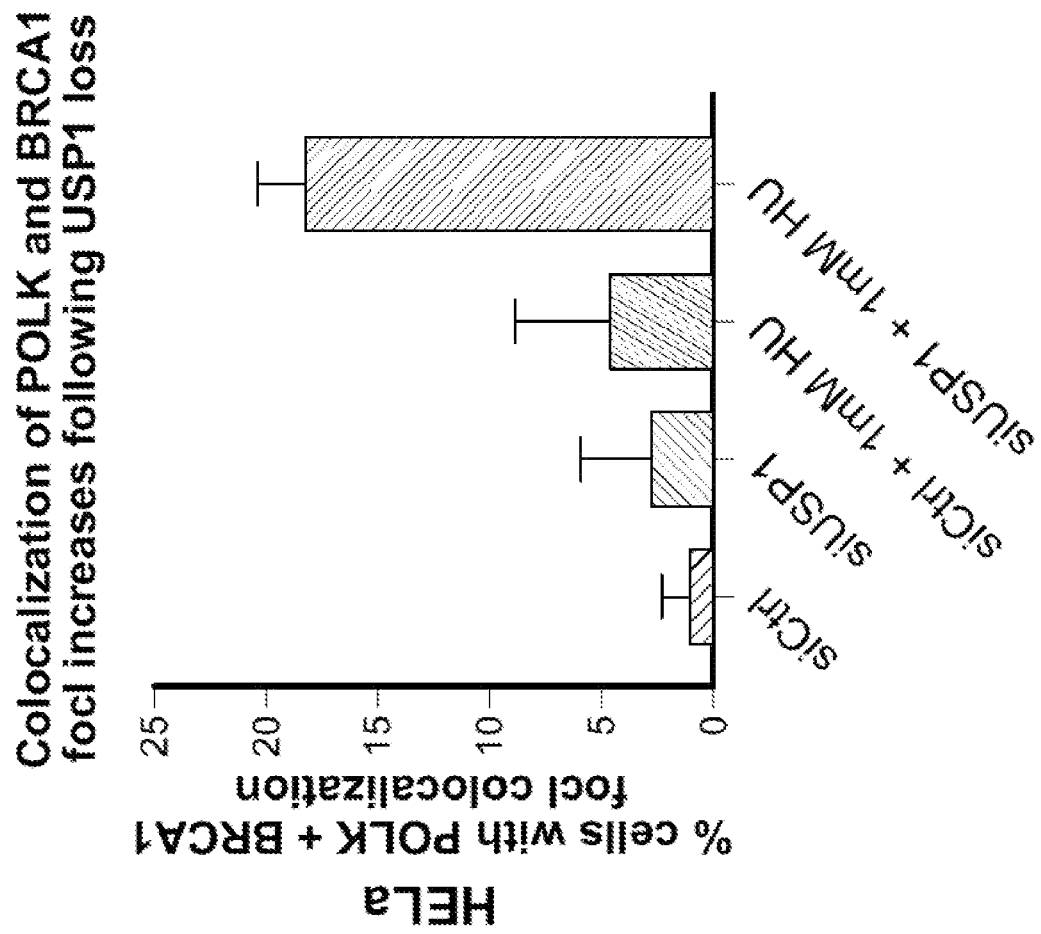
FIG. 22C. Quantification of POLK and BRCA1 foci colocalization following USP1 silencing and hydroxyurea treatment.
Figure 22E:
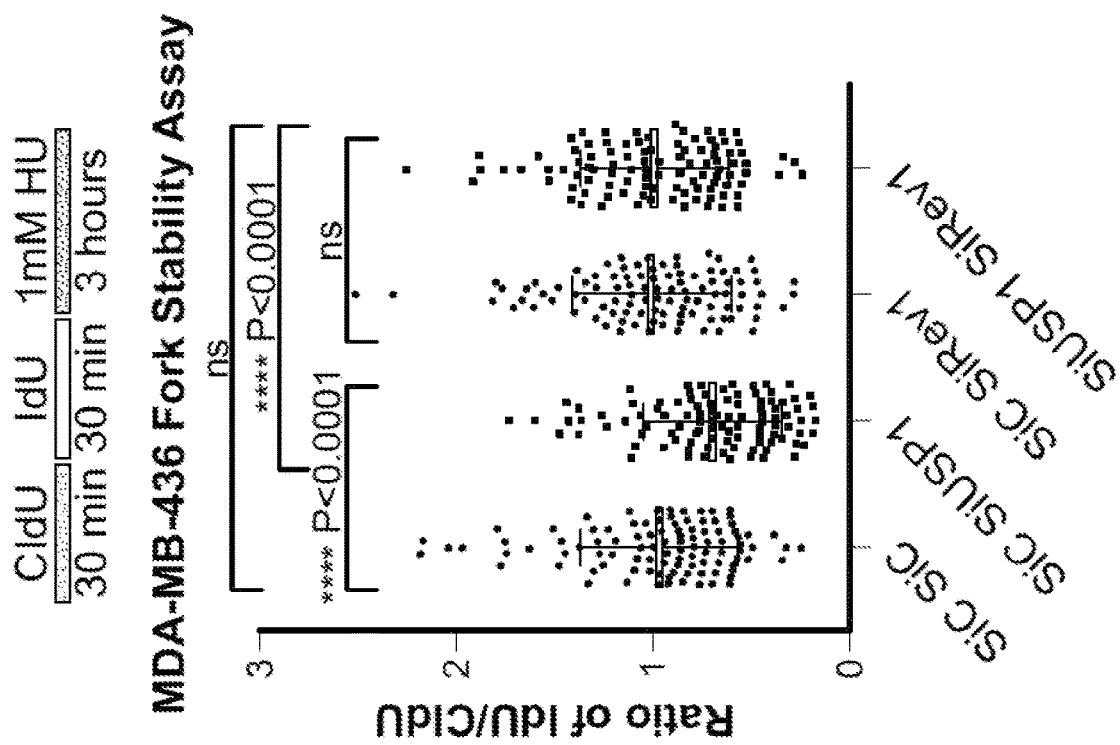
FIG. 22E. Schematic of the experimental design for the fiber assay and graphical quantification of fiber assay measuring replication fork stability in MDA-MB-436 cells following treatment with either siCtrl, siUSP1, siREV1, or siUSP1 and siREV1.
Figure 22D:
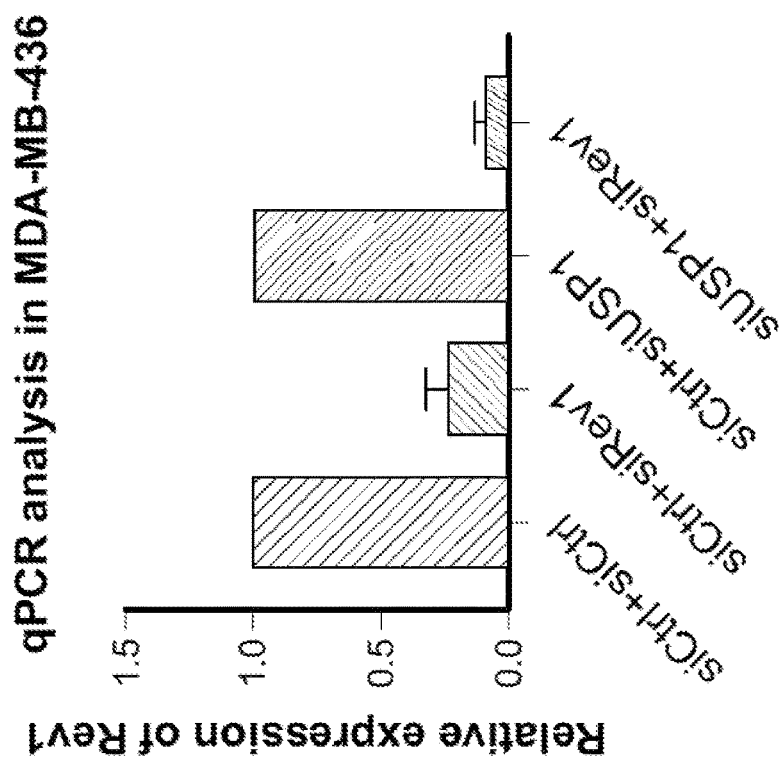
FIG. 22D. Quantitation of the REV1 knockdown efficiency by qPCR.

USP1 silencing resulted in increased POLK foci colocalization with BRCA1 foci (FIG. 22C) suggesting that BRCA1 is required for fork stabilization in the setting of persistent POLK recruitment. Knockdown of REV1, another TLS polymerase recruited by PCNA-Ub, also resulted in replication fork protection (FIG. 22D).

Figures 18A, 18B:
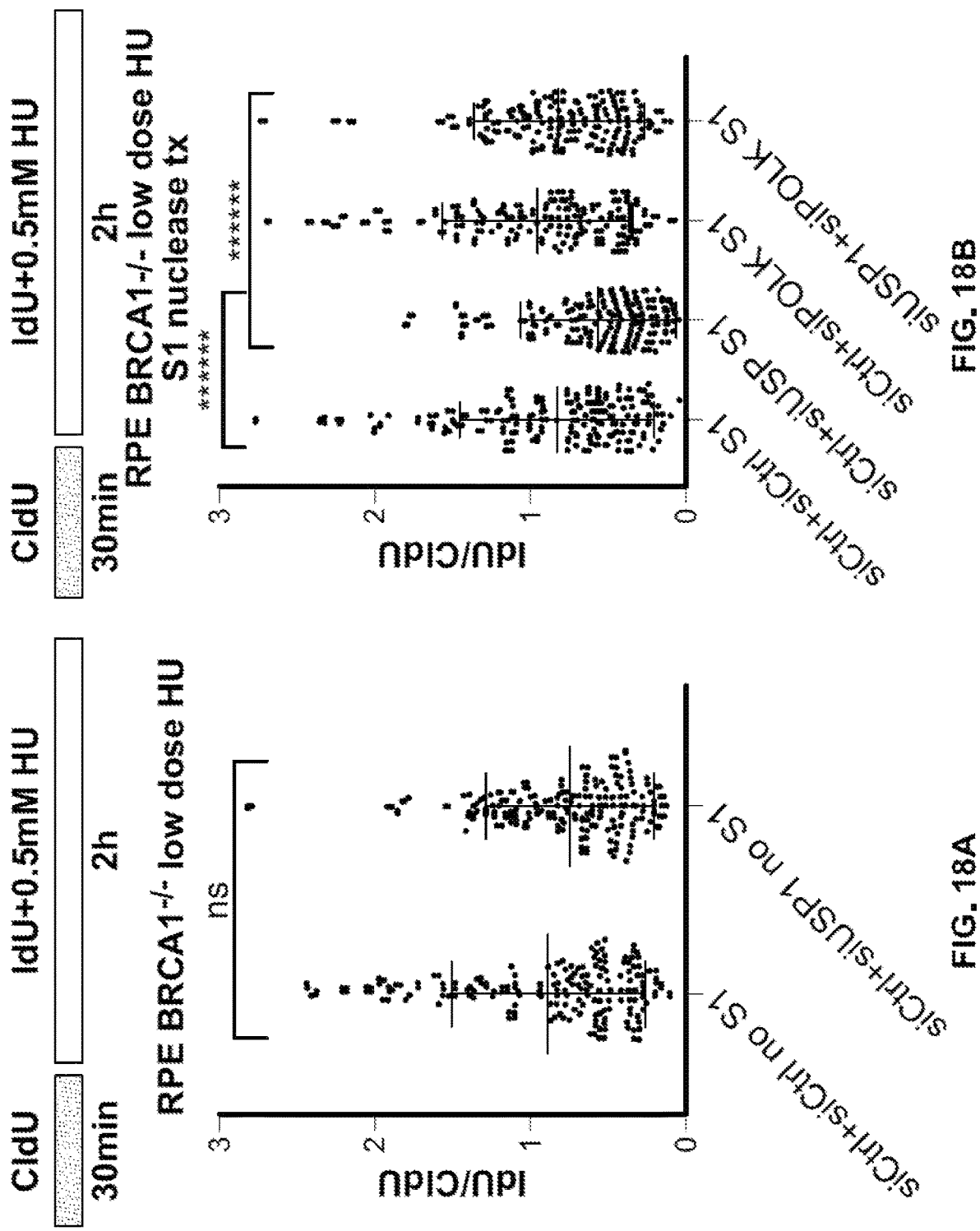
FIG. 18A. Fiber assays in BRCA1 deficient RPE cells treated with low dose HU (0.5 mM). Schematic of CldU, IdU and HU treatment (top) and graphical quantification of fibers from cells treated with siUSP1 and low dose HU (bottom).
FIG. 18B. Schematic of CldU, IdU and HU treatment (top) and graphical quantification of fibers from cells treated with siUSP1 and low dose HU followed by 51 nuclease treatment. Cells were treated with siRNAs and low dose HU followed by DNA extraction. DNA solutions were then treated with 51 nuclease before combing the DNA fibers onto coverslips.

TLS polymerases exhibit low fidelity. Persistent TLS polymerase recruitment may therefore cause replication fork destabilization through the introduction of aberrant replication products such as DNA gaps and mismatches. In order to determine the presence of gaps and mismatches in the absence of USP1, a fiber assay was performed along with S1 nuclease treatment. S1 nuclease degrades DNA structures having gaps and mismatches. A low dose hydroxyurea (0.5 mM) treatment did not significantly affect the fork stability in BRCA1 deficient cells treated with siUSP1 (FIGS. 18A-18B). However, Si nuclease treatment resulted in fork degradation in BRCA1 deficient cells following USP1 knockdown (FIGS. 18A-18B). Again, loss of the TLS polymerase POLK rescued this phenotype (FIGS. 18A-18B). Taken together, the increased TLS activity after USP1 loss leads to DNA gaps and mismatches and to fork degradation in BRCA1-deficient cells.

Figure 22G:
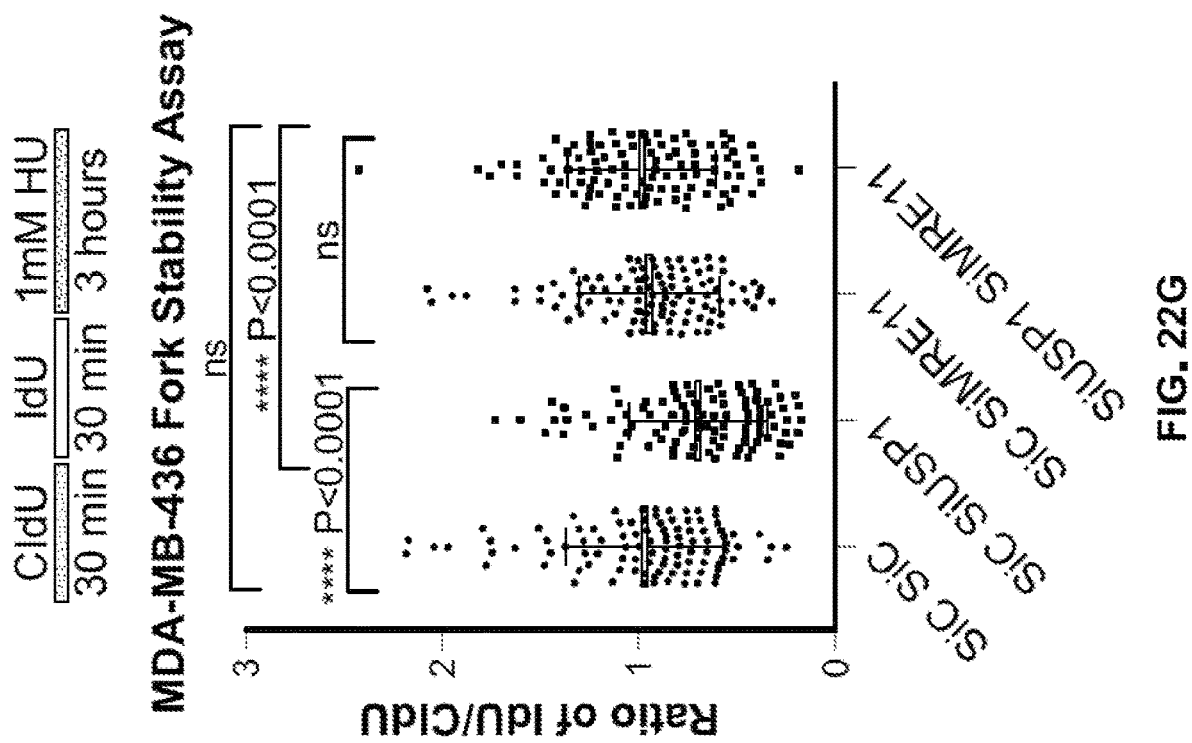
FIG. 22G. Schematic of the experimental design for the fiber assay and graphical quantification of fiber assay measuring replication fork stability in MDA-MB-436 cells following treatment with either siCtrl, siUSP1, siMRE11, or siUSP1 and siMRE11.
Figure 22F:
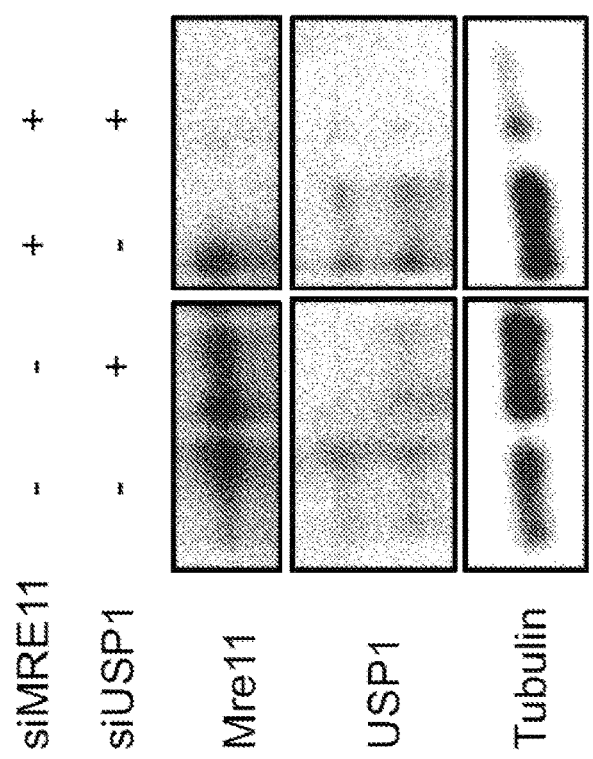
FIG. 22F. Western blot of the lysates from MDA-MB-436 cells showing knockdown efficiency of MRE11 and USP1.
Figure 22I:
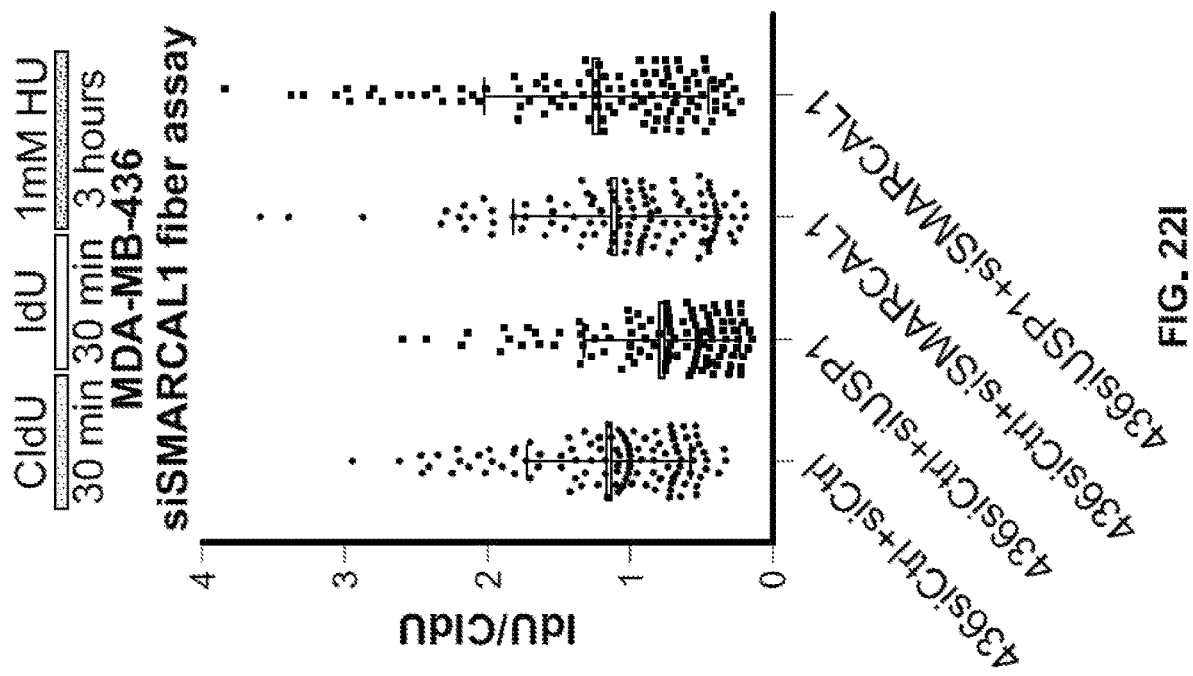
FIG. 22I. Schematic of the experimental design for the fiber assay and graphical quantification of fiber assay measuring replication fork stability in MDA-MB-436 cells following treatment with either siCtrl, siUSP1, siSMARCAL1, or siUSP1 and siSMARCAL1.
Figure 22H:
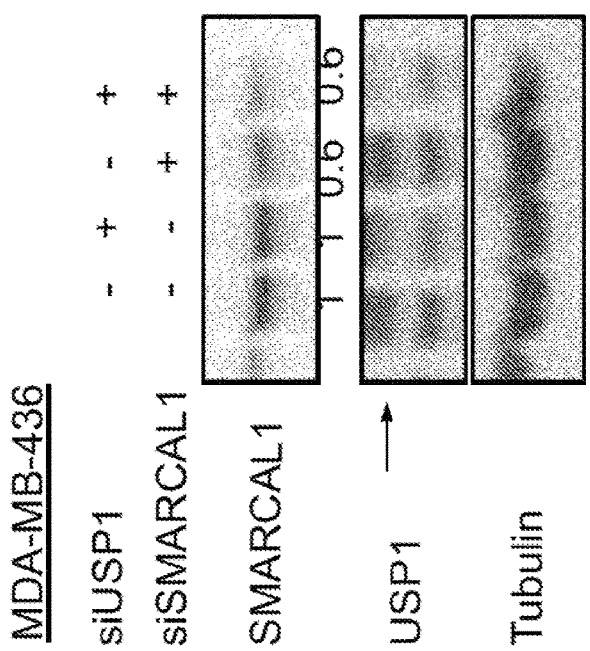
FIG. 22H. Western blot of the lysates from MDA-MB-436 cells showing knockdown efficiency of SMARCAL1 and USP1. Values below the SMARCAL1 blot indicate densitometry analysis of SMARCAL1 protein levels.
Figure 22K:
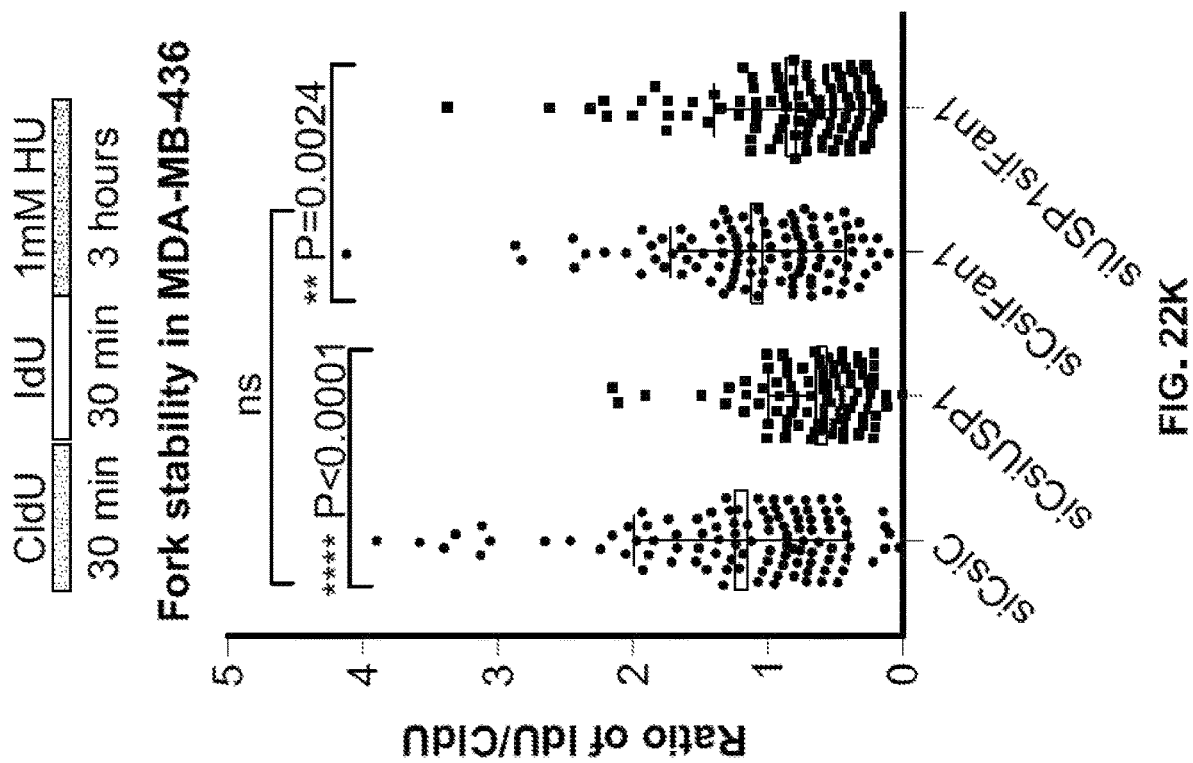
FIG. 22K. Schematic of the experimental design for the fiber assay (top) and graphical quantification of fiber assay measuring replication fork stability in MDA-MB-436 cells following treatment with either siCtrl, siUSP1, siFAN1, or siUSP1 and siFAN1 (bottom).
Figure 22J:
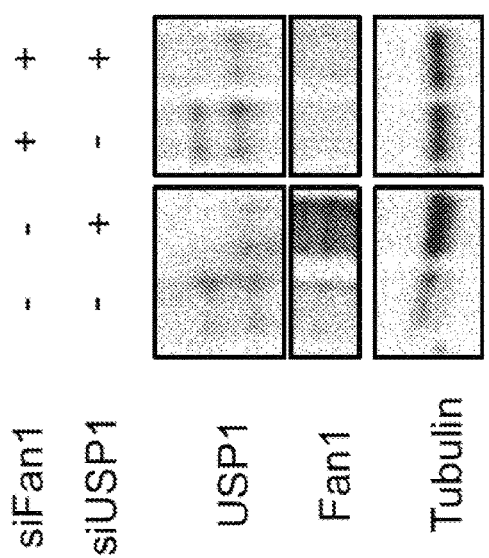
FIG. 22J. Western blot of the lysates from MDA-MB-436 cells showing knockdown efficiency of FAN1 and USP1.

Silencing of the nucleases DNA2 and MRE11 also rescued replication fork instability and viability in BRCA1-deficient cells following USP1 inhibition (FIGS. 22F-22G). Reversed replication forks are degraded by MRE11 in BRCA1- or BRCA2-deficient cells, and SMARCAL1 is known to promote fork reversal. It was reasoned that, in the absence of USP1, SMARCAL1 may be contributing to fork reversal and to the enhanced fork degradation. Accordingly, SMARCAL1 knockdown rescued the fork degradation phenotype in BRCA1-deficient cells following USP1 loss (FIGS. 22H-22I), suggesting that replication fork instability following USP1 depletion in BRCA1 deficient cells is dependent on fork reversal. In contrast, knockdown of the FAN1 nuclease did not rescue this phenotype (FIGS. 22J and 22K).

Example 10

DNA-Binding Activity of USP1 is Required to Limit TLS-Mediated Mutagenesis

Figure 13C:
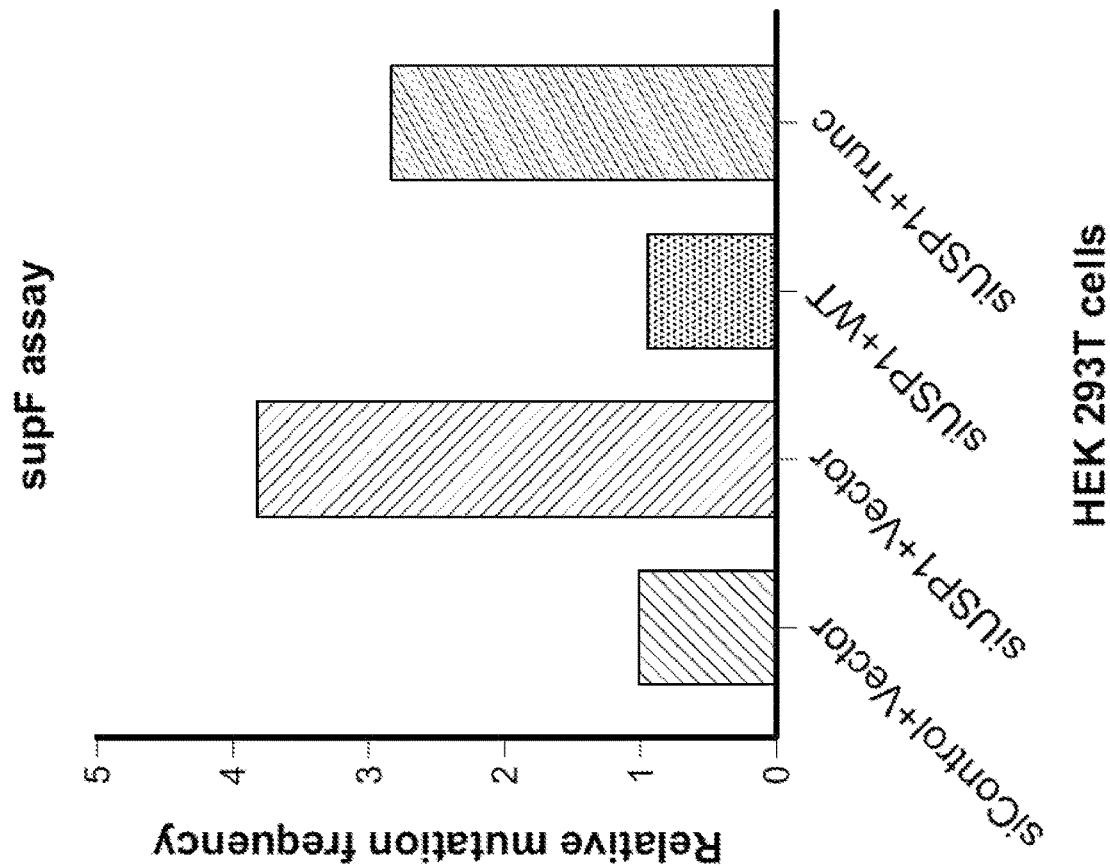
FIG. 13C. SupF assay performed in HEK293T cells following treatment with siCtrl+Vector, siUSP1+Vector, siUSP1+wild-type USP1, siUSP1+Trunc-USP1.
Figure 13B:
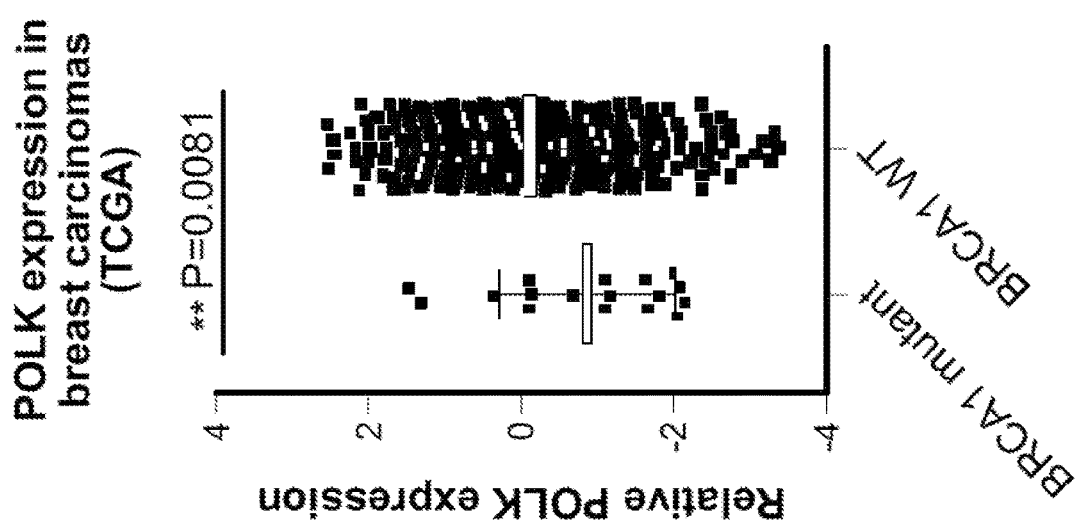
FIG. 13B. POLK expression levels in BRCA1 mutant and BRCA1 wild-type breast cancers plotted using data from TCGA.
Figure 13E:
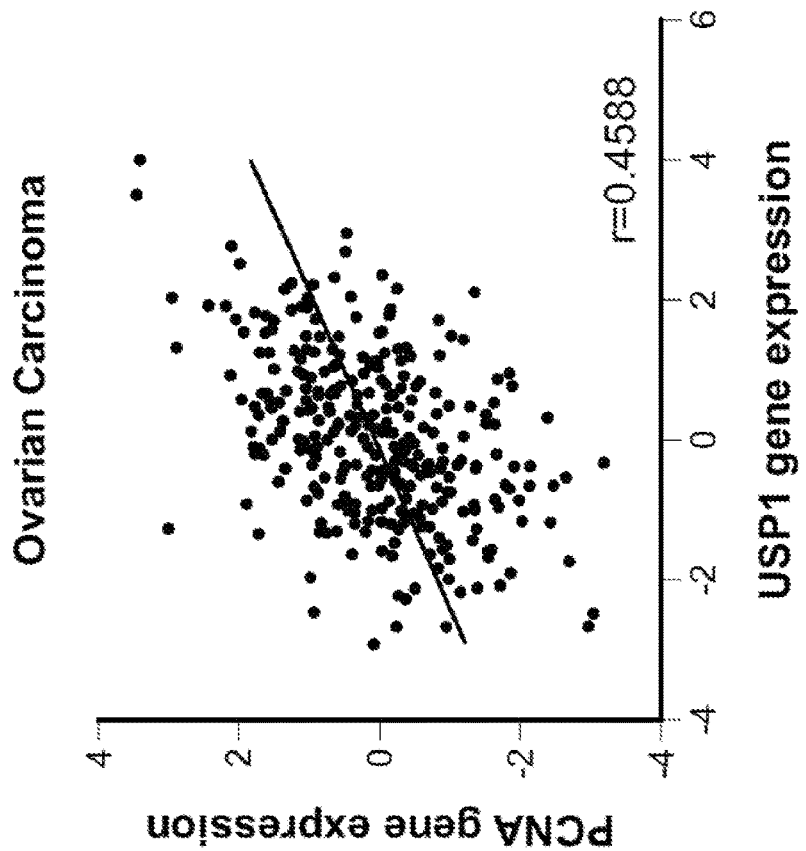
FIG. 13E. USP1 expression correlates with PCNA expression in ovarian cancers.
Figure 13D:
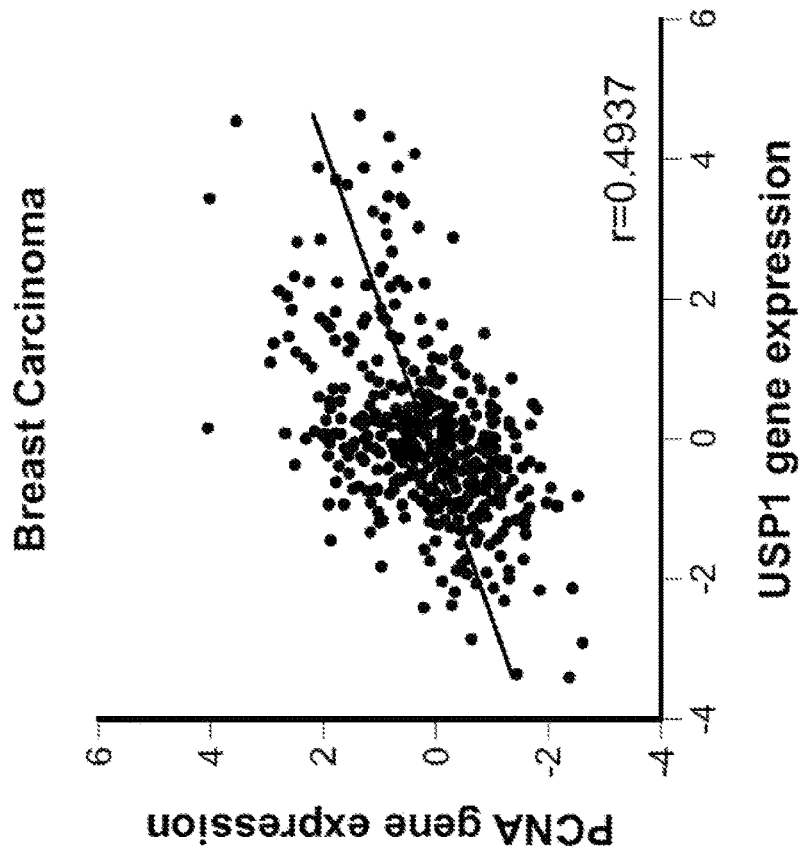
FIG. 13D. USP1 expression correlates with PCNA expression in breast cancers.
Figure 13F:
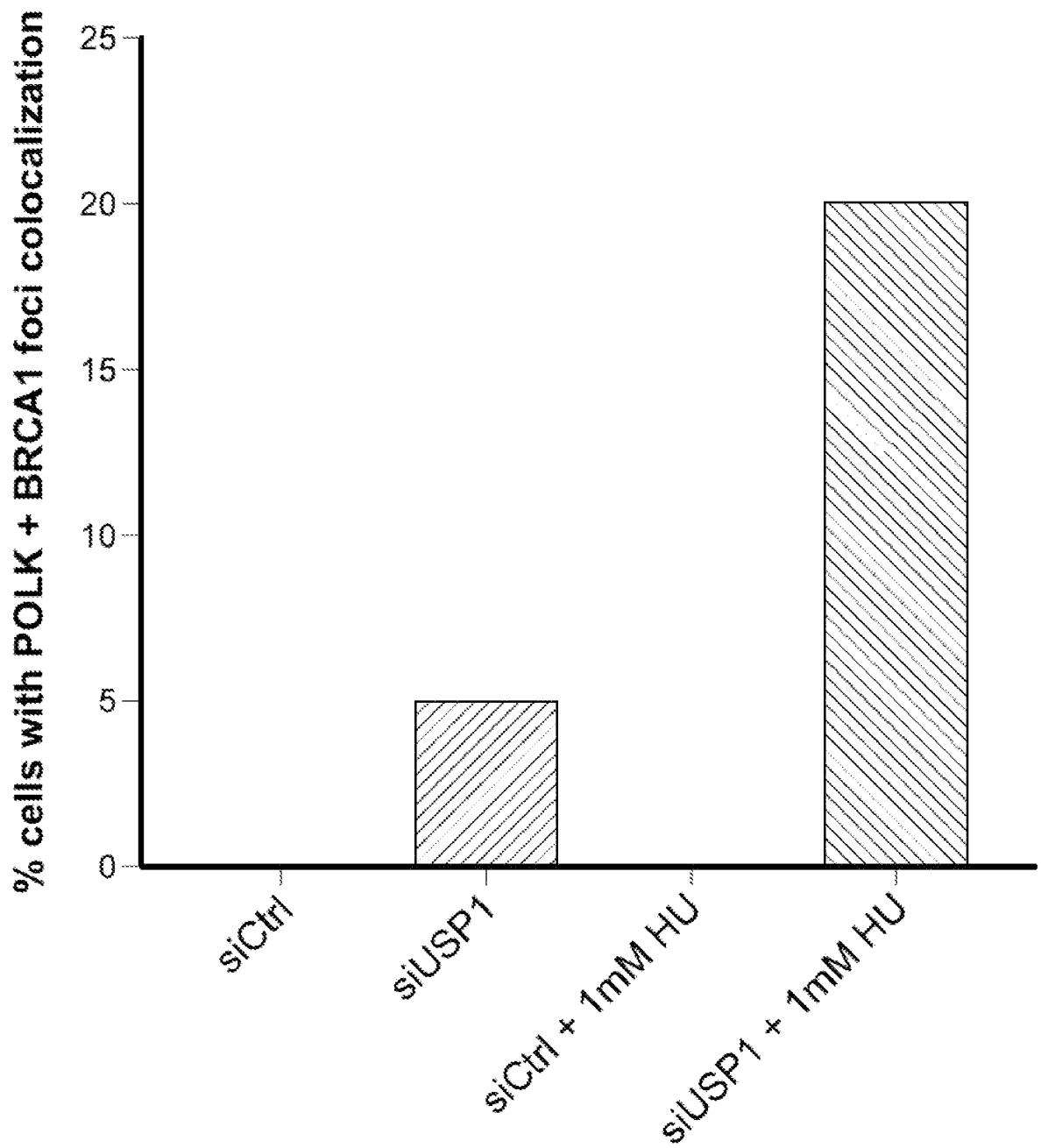
FIG. 13F. Quantification of POLK and BRCA1 foci colocalization following USP1 silencing and hydroxyurea treatment.

Increased PCNA monoubiquitination results in the recruitment of POLK and other error-prone TLS polymerases (40). Accordingly, knockdown of USP1 in 293T cells resulted in the increased generation of point mutations via the supF assay (FIG. 13C). Transfection with siRNA resistant WT-USP1, but not Trunc-USP1, reduced the mutagenesis level. Taken together, the toxicity resulting from increased PCNA monoubiquitination may be an indirect consequence of elevated TLS polymerase activity and TLS.

Figures 23A, 23B:
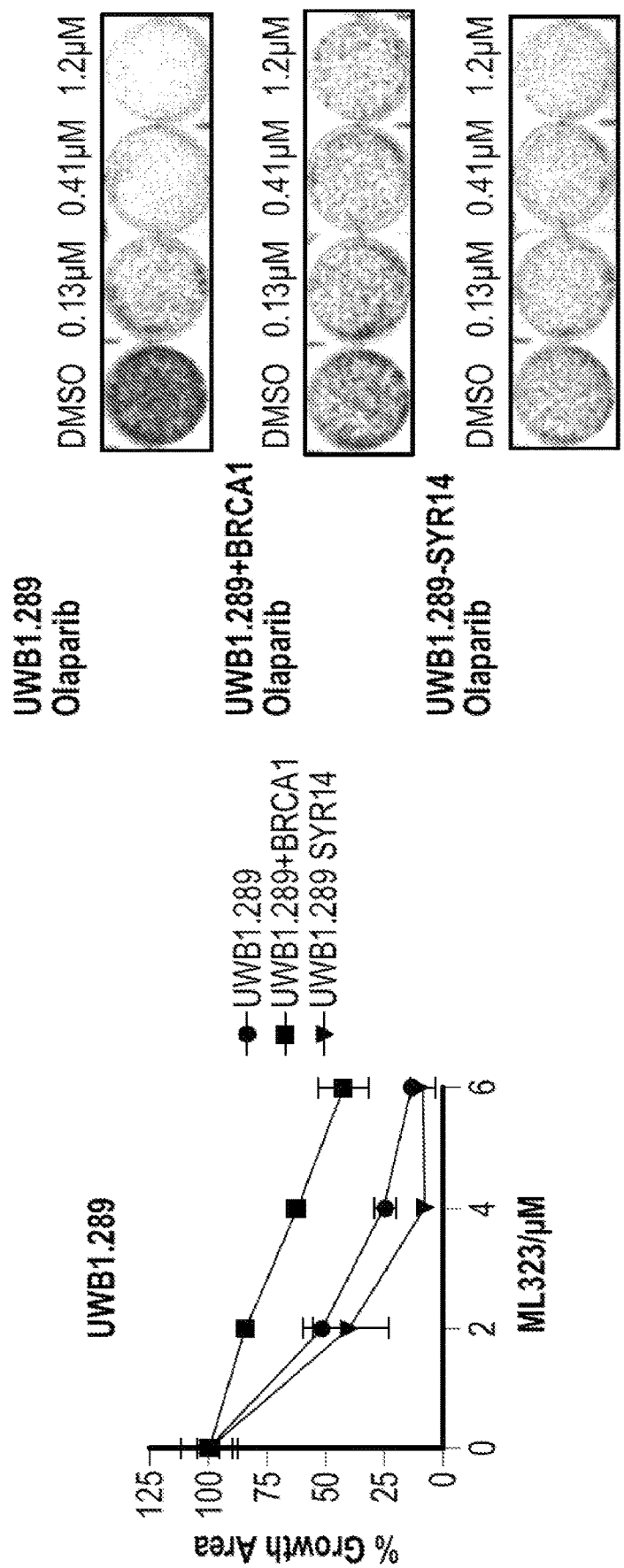
FIG. 23A. Quantification of colonies after clonogenic assay of parental BRCA1-deficient UWB1.289 cells and PARP inhibitor resistant UWB1.289 $SYR_{14}$ cells treated with USP1 inhibitor ML323.
FIG. 23B. Representative colony assays of UWB1.289 cells, UWB1.289+BRCA1 cells, and PARP inhibitor resistant UWB1.289-$SYR_{14}$ cells treated with Olaparib.

PARP inhibitor resistance of BRCA1-deficient tumor cells can result from two major mechanisms-namely, the restoration of HR repair and the stabilization of the replication fork. BRCA1-deficient cells, with acquired PARP inhibitor resistance resulting from these mechanisms, have recently been generated. Interestingly, PARP inhibitor resistant cells resulting from fork stabilization remained sensitive to the USP1 inhibitor ML323 (FIGS. 23A-23B). In contrast, PARP inhibitor resistant cells resulting from restoration of HR through 53BP1 silencing were resistant to the USP1 inhibitor. Taken together, these results suggest that a subset of PARP inhibitor resistant BRCA1-deficient cells, including those which acquired resistance through fork stabilization, are sensitive to USP1 inhibition. Accordingly, USP1 inhibitors may be useful in the treatment of BRCA1-deficient tumors with acquired PARP inhibitor resistance through this mechanism.

Figure 14:
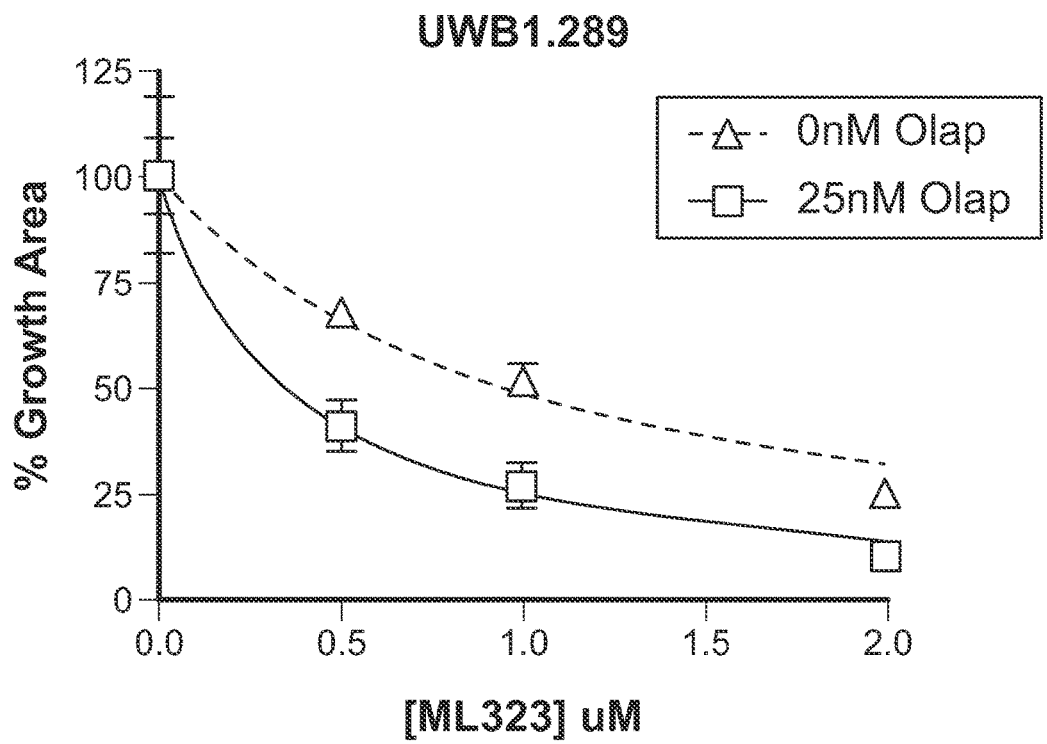
FIG. 14. USP1 inhibition is non-epistatic with PARP inhibitors in BRCA1 deficient cells (Top: BRCA1-deficient UWB1.289 cells treated with 0 nM or 25 nM of Olaparib and increasing doses of USP1 inhibitor ML323. Bottom: Representative pictures of UWB1.289 colonies).
Figure 14:
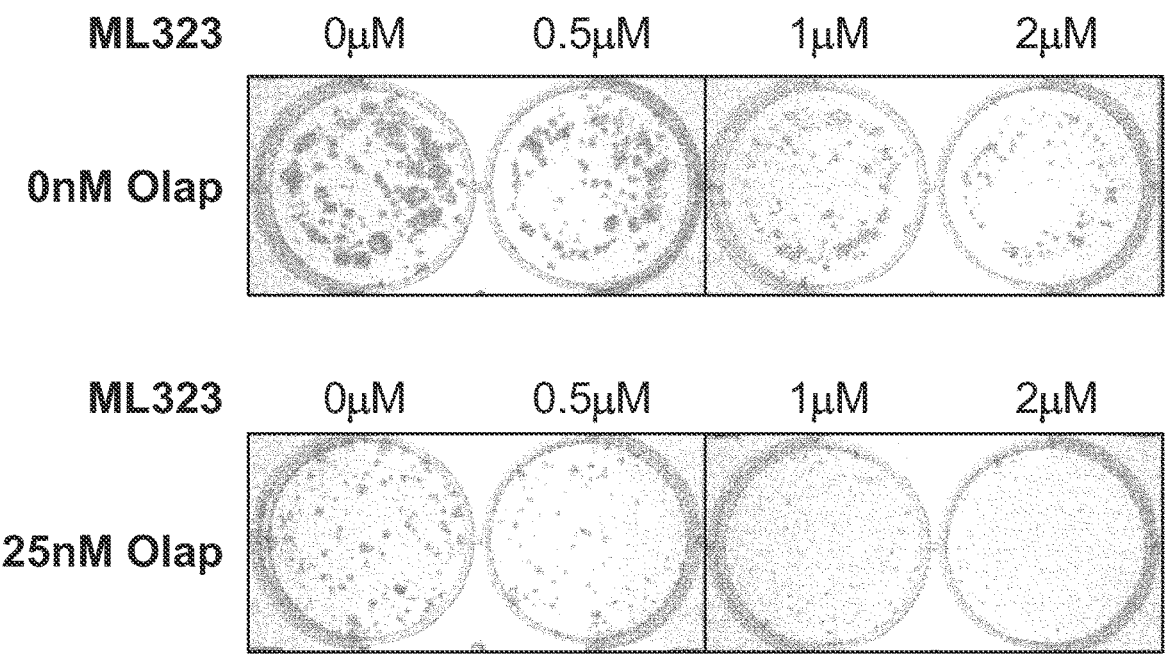

The results support a model of DNA-stimulated USP1 activation at the replication fork as a mechanism of fork protection in BRCA1 deficient cells through the deubiquitination of PCNA (FIG. 7). Knockdown of USP1 in BRCA1-deficient cells results in increased PCNA monoubiquitination, increased fork resection, and subsequent cell death. These data clearly show that USP1 inhibitors represent a new class of small molecule inhibitors that can potentiate the response of PARP inhibitors in BRCA1-deficient cells (FIG. 14).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

REFERENCES

1. Pathania S, Bade S, Le Guillou M, Burke K, Reed R, Bowman-Colin C, et al. BRCA1 haploinsufficiency for replication stress suppression in primary cells. Nature communications. 2014; 5:5496.
2. Willis N A, Chandramouly G, Huang B, Kwok A, Follonier C, Deng C, et al. BRCA1 controls homologous recombination at Tus/Ter-stalled mammalian replication forks. Nature. 2014; 510(7506):556-9.
3. Moynahan M E, Chiu J W, Koller B H, Jasin M. Brca1 controls homology-directed DNA repair. Molecular cell. 1999; 4(4):511-8.
4. Farmer H, McCabe N, Lord C J, Tutt A N. Targeting the DNA repair defect in BRCA mutant cells as a therapeutic strategy. Nature. 2005; 434(7035):917.
5. Schlacher K, Wu H, Jasin M. A distinct replication fork protection pathway connects Fanconi anemia tumor suppressors to RAD51-BRCA1/2. Cancer Cell. 2012; 22(1):106-16.
6. Kais Z, Rondinelli B, Holmes A, O'Leary C, Kozono D, D'Andrea A D, et al. FANCD2 Maintains Fork Stability in BRCA1/2-Deficient Tumors and Promotes Alternative End-Joining DNA Repair. Cell reports. 2016; 15(11):2488-99.
7. Ceccaldi R, Liu J C, Amunugama R, Hajdu I, Primack B, Petalcorin M I, et al. Homologous-recombination-deficient tumours are dependent on Poltheta-mediated repair. Nature. 2015; 518(7538):258-62.
8. Ledermann J, Harter P, Gourley C, Friedlander M, Vergote I, Rustin G, et al. Olaparib maintenance therapy in patients with platinum-sensitive relapsed serous ovarian cancer: a preplanned retrospective analysis of outcomes by BRCA status in a randomised phase 2 trial. The Lancet Oncology. 2014; 15(8):852-61.
9. Oza A M, Cibula D, Benzaquen A O, Poole C, Mathijssen R H, Sonke G S, et al. Olaparib combined with chemotherapy for recurrent platinum-sensitive ovarian cancer: a randomised phase 2 trial. The Lancet Oncology. 2015; 16(1):87-97.
10. Ledermann J A, Harter P, Gourley C, Friedlander M, Vergote I, Rustin G, et al. Overall survival in patients with platinum-sensitive recurrent serous ovarian cancer receiving olaparib maintenance monotherapy: an updated analysis from a randomised, placebo-controlled, double-blind, phase 2 trial. The Lancet Oncology. 2016; 17(11):1579-89.
11. Ray Chaudhuri A, Callen E, Ding X, Gogola E, Duarte A A, Lee J E, et al. Replication fork stability confers chemoresistance in BRCA-deficient cells. Nature. 2016; 535(7612):382-7.
12. Xu G, Chapman J R, Brandsma I, Yuan J, Mistrik M, Bouwman P, et al. REV7 counteracts DNA double-strand break resection and affects PARP inhibition. Nature. 2015; 521(7553):541-4.
13. Boersma V, Moatti N, Segura-Bayona S, Peuscher MH, van der Torre J, Wevers BA, et al. MAD2L2 controls DNA repair at telomeres and DNA breaks by inhibiting 5' end resection. Nature. 2015; 521(7553):537-40.
14. Jaspers J E, Kersbergen A, Boon U, Sol W, van Deemter L, Zander S A, et al. Loss of 53BP1 causes PARP inhibitor resistance in Brca1-mutated mouse mammary tumors. Cancer discovery. 2013; 3(1):68-81.
15. Choi Y E, Meghani K, Brault M E, Leclerc L, He Y J, Day T A, et al. Platinum and PARP Inhibitor Resistance Due to Overexpression of MicroRNA-622 in BRCA1-Mutant Ovarian Cancer. Cell reports. 2016; 14(3):429-39.
16. D'Andrea A, Pellman D. Deubiquitinating enzymes: a new class of biological regulators. Critical reviews in biochemistry and molecular biology. 1998; 33(5):337-52.
17. Komander D, Rape M. The ubiquitin code. Annual review of biochemistry. 2012; 81:203-29.
18. Nijman S M, Luna-Vargas M P, Velds A, Brummelkamp T R, Dirac A M, Sixma T K, et al. A genomic and functional inventory of deubiquitinating enzymes. Cell. 2005; 123(5):773-86.
19. Davis MI, Simeonov A. Ubiquitin-specific proteases as druggable targets. Drug target review. 2015; 2(3):60.
20. Cohn M A, Kee Y, Haas W, Gygi S P, D'Andrea AD. UAF1 is a subunit of multiple deubiquitinating enzyme complexes. The Journal of biological chemistry. 2009; 284(8):5343-51.
21. Sowa M E, Bennett E J, Gygi S P, Harper J W. Defining the human deubiquitinating enzyme interaction landscape. Cell. 2009; 138(2):389-403.
22. Villamil M A, Liang Q, Zhuang Z. The WD40-repeat protein-containing deubiquitinase complex: catalysis, regulation, and potential for therapeutic intervention. Cell biochemistry and biophysics. 2013; 67(1):111-26.
23. Yin J, Schoeffler A J, Wickliffe K, Newton K, Starovasnik M A, Dueber E C, et al. Structural Insights into WD-Repeat 48 Activation of Ubiquitin-Specific Protease 46. Structure (London, England: 1993). 2015; 23(11):2043-54.
24. Li H, Lim K S, Kim H, Hinds T R, Jo U, Mao H, et al. Allosteric activation of ubiquitin-specific proteases by β-propeller proteins UAF1 and WDR20. Molecular cell. 2016; 63(2):249-60.
25. Ye Y, Scheel H, Hofmann K, Komander D. Dissection of USP catalytic domains reveals five common insertion points. Molecular BioSystems. 2009; 5(12):1797-808.
26. Liang F, Longerich S, Miller A S, Tang C, Buzovetsky O, Xiong Y, et al. Promotion of RAD51-Mediated Homologous DNA Pairing by the RAD51AP1-UAF1 Complex. Cell reports. 2016; 15(10):2118-26.
27. Dungrawala H, Rose K L, Bhat K P, Mohni K N, Glick G G, Couch F B, et al. The Replication Checkpoint Prevents Two Types of Fork Collapse without Regulating Replisome Stability. Molecular cell. 2015; 59(6):998-1010.
28. Cukras S, Lee E, Palumbo E, Benavidez P, Moldovan G-L, Kee Y. The USP1-UAF1 complex interacts with RAD51AP1 to promote homologous recombination repair. Cell cycle (Georgetown, Tex). 2016; 15(19):2636-46.
29. Liang Q, Dexheimer TS, Zhang P, Rosenthal AS, Villamil MA, You C, et al. A selective USP1-UAF1 inhibitor 29. links deubiquitination to DNA damage responses. Nature chemical biology. 2014; 10(4):298-304.
30. Network CGA. Comprehensive molecular portraits of human breast tumors. Nature. 2012; 490(7418):61.
31. Cohn MA, Kowal P, Yang K, Haas W, Huang TT, Gygi SP, et al. A UAF1-containing multisubunit protein complex regulates the Fanconi anemia pathway. Molecular cell. 2007; 28(5):786-97.
32. Dahlberg C L, Juo P. The WD40-repeat proteins WDR-20 and WDR-48 bind and activate the deubiquitinating enzyme USP-46 to promote the abundance of the glutamate receptor GLR-1 in the ventral nerve cord of Caenorhabditis elegans. Journal of Biological Chemistry. 2014; 289(6):3444-56.
33. Eletr Z M, Wilkinson K D. Regulation of proteolysis by human deubiquitinating enzymes. Biochimica et Biophysica Acta (BBA)-Molecular Cell Research. 2014; 1843(1):114-28.
34. Huang T T, Nijman S M, Mirchandani K D, Galardy P J, Cohn M A, Haas W, et al. Regulation of monoubiquitinated PCNA by DUB autocleavage. Nature cell biology. 2006; 8(4):341-7.
35. Kee Y, Yang K, Cohn M A, Haas W, Gygi S P, D'Andrea A D. WDR$_{20}$ regulates activity of the USP12 UAF1 deubiquitinating enzyme complex. Journal of Biological Chemistry. 2010; 285(15): 11252-7.
36. Mistry H, Hsieh G, Buhrlage S J, Huang M, Park E, Cuny G D, et al. Small-molecule inhibitors of USP1 target ID1 degradation in leukemic cells. Molecular cancer therapeutics. 2013; 12(12):2651-62.
37. Lecona E, Rodriguez-Acebes S, Specks J, Lopez-Contreras A J, Ruppen I, Murga M, et al. USP7 is a SUMO deubiquitinase essential for DNA replication. Nature structural & molecular biology. 2016.
38. Sirbu B M, Couch F B, Feigerle J T, Bhaskara S, Hiebert S W, Cortez D. Analysis of protein dynamics at active, stalled, and collapsed replication forks. Genes & development. 2011; 25(12):1320-7.
39. Jones M J, Colnaghi L, Huang T T. Dysregulation of DNA polymerase kappa recruitment to replication forks results in genomic instability. The EMBO journal. 2012; 31(4):908-18.
40. Choe K N, Moldovan G-L. Forging Ahead through Darkness: PCNA, Still the Principal Conductor at the Replication Fork. Molecular cell. 2017; 65(3):380-92.
41. Schlacher K, Wu H, Jasin M. A distinct replication fork protection pathway connects Fanconi anemia tumor suppressors to RAD51-BRCA1/2. Cancer cell. 2012; 22(1): 106-16.
42. Tian F, Sharma S, Zou J, Lin S Y, Wang B, Rezvani K, et al. BRCA1 promotes the ubiquitination of PCNA and recruitment of translesion polymerases in response to replication blockade. Proceedings of the National Academy of Sciences of the United States of America. 2013; 110(33):13558-63.
43. Nik-Zainal S, Davies H, Staaf J, Ramakrishna M, Glodzik D, Zou X, et al. Landscape of somatic mutations in 560 breast cancer whole-genome sequences. Nature. 2016; 534(7605):47-54.
44. Stephens P J, Tarpey P S, Davies H, Van Loo P, Greenman C, Wedge D C, et al. The landscape of cancer genes and mutational processes in breast cancer. Nature. 2012; 486(7403):400-4.
45. Cancer Genome Atlas Research N. Integrated genomic analyses of ovarian carcinoma. Nature. 2011; 474(7353): 609-15.
46. Leung K, Abou E H M, Bremner R. A rapid and efficient method to purify proteins at replication forks under native conditions. Biotechniques. 2013; 55(4):204-6.

SEQUENCE LISTING

```
Sequence total quantity: 20
SEQ ID NO: 1           moltype = DNA  length = 21
FEATURE                Location/Qualifiers
misc_feature           1..21
                       note = Description of Artificial Sequence: Synthetic
                       oligonucleotide
source                 1..21
                       mol_type = other DNA
                       organism = synthetic construct
SEQUENCE: 1
tcggcaatac ttgctatctt a                                                   21

SEQ ID NO: 2           moltype = DNA  length = 19
FEATURE                Location/Qualifiers
misc_feature           1..19
                       note = Description of Artificial Sequence: Synthetic
                       oligonucleotide
source                 1..19
                       mol_type = other DNA
                       organism = synthetic construct
SEQUENCE: 2
ccatacaaac attggtaaa                                                      19

SEQ ID NO: 3           moltype = DNA  length = 25
FEATURE                Location/Qualifiers
misc_feature           1..25
                       note = Description of Artificial Sequence: Synthetic
                       oligonucleotide
source                 1..25
                       mol_type = other DNA
                       organism = synthetic construct
SEQUENCE: 3
caccggtcat acctagtgaa agtaa                                               25
```

```
SEQ ID NO: 4              moltype = DNA  length = 20
FEATURE                   Location/Qualifiers
source                    1..20
                          mol_type = other DNA
                          organism = Homo sapiens
SEQUENCE: 4
gatccactca cagtttccat                                                     20

SEQ ID NO: 5              moltype = DNA  length = 20
FEATURE                   Location/Qualifiers
source                    1..20
                          mol_type = other DNA
                          organism = Homo sapiens
SEQUENCE: 5
tcttgtgctg acttaccaga                                                     20

SEQ ID NO: 6              moltype = DNA  length = 39
FEATURE                   Location/Qualifiers
misc_feature              1..39
                          note = Description of Artificial Sequence: Synthetic
                          oligonucleotide
source                    1..39
                          mol_type = other DNA
                          organism = synthetic construct
SEQUENCE: 6
ccagtgaatt gttgctcggt acctgctaac ggtaatcgg                                39

SEQ ID NO: 7              moltype = DNA  length = 39
FEATURE                   Location/Qualifiers
misc_feature              1..39
                          note = Description of Artificial Sequence: Synthetic
                          oligonucleotide
source                    1..39
                          mol_type = other DNA
                          organism = synthetic construct
SEQUENCE: 7
ccgattaccg ttagcaggta ccgagcaaca attcactgg                                39

SEQ ID NO: 8              moltype = DNA  length = 39
FEATURE                   Location/Qualifiers
misc_feature              1..39
                          note = Description of Artificial Sequence: Synthetic
                          oligonucleotide
source                    1..39
                          mol_type = other DNA
                          organism = synthetic construct
SEQUENCE: 8
cagctatggg acattcgata ccgagcaaca attcactgg                                39

SEQ ID NO: 9              moltype = AA  length = 770
FEATURE                   Location/Qualifiers
REGION                    1..770
                          note = Description of Unknown: USP1 sequence
source                    1..770
                          mol_type = protein
                          organism = unidentified
SEQUENCE: 9
MPGVIPSESN GLSRGSPSKK NRLSLKFFQK KETKRALDFT DSQENEEKAS EYRASEIDQV    60
VPAAQSSPIN CEKRENLLPF VGLNNLGNTC YLNSILQVLY FCPGFKSGVK HLFNIISRKK   120
EALKDEANQK DKGNCKEDSL ASYELICSLQ SLIISVEQLQ ASFLLNPEKY TDELATQPRR   180
LLNTLRELNP MYEGYLQHDA QEVLQCILGN IQETCQLLKK EEVKNVAELP TKVEEIPHPK   240
EEMNGINSIE MDSMRHSEDF KEKLPKGNGK RKSDTEFGNM KKKVKLSKEH QSLEENQRQT   300
RSKRKATSDT LESPPKIIPK YISENESPRP SQKKSRVKIN WLKSATKQPS ILSKFCSLGK   360
ITTNQGVKGQ SKENECDPEE DLGKCESDNT TNGCGLESPG NTVTPVNVNE VKPINKGEEQ   420
IGFELVEKLF QGQLVLRTRC LECESLTERR EDFQDISVPV QEDELSKVEE SSEISPEPKT   480
EMKTLRWAIS QFASVERIVG EDKYFCENCH HYTEAERSLL FDKMPEVITI HLKCFAASGL   540
EFDCYGGGLS KINTPLLTPL KLSLEEWSTK PTNDSYGLFA VVMHSGITIS SGHYTASVKV   600
TDLNSLELDK GNFVVDQMCE IGKPEPLNEE EARGVVENYN DEEVSIRVGG NTQPSKVLNK   660
KNVEAIGLLG GQKSKADYEL YNKASNPDKV ASTAFAENRN SETSDTTGTH ESDRNKESSD   720
QTGINISGFE NKISYVVQSL KEYEGKWLLF DDSEVKVTEE KDFLNSLSPS              770

SEQ ID NO: 10             moltype = AA  length = 370
FEATURE                   Location/Qualifiers
REGION                    1..370
                          note = Description of Unknown: USP12 sequence
source                    1..370
                          mol_type = protein
                          organism = unidentified
SEQUENCE: 10
```

```
MEILMTVSKF ASICTMGANA SALEKEIGPE QFPVNEHYFG LVNFGNTCYC NSVLQALYFC    60
RPFREKVLAY KSQPRKKESL LTCLADLFHS IATQKKKVGV IPPKKFITRL RKENELFDNY   120
MQQDAHEFLN YLLNTIADIL QEERKQEKQN GRLPNGNIDN ENNNSTPDPT WVHEIFQGTL   180
TNETRCLTCE TISSKDEDFL DLSVDVEQNT SITHCLRGFS NTETLCSEYK YYCEECRSKQ   240
EAHKRMKVKK LPMILALHLK RFKYMDQLHR YTKLSYRVVF PLELRLFNTS GDATNPDRMY   300
DLVAVVVHCG SGPNRGHYIA IVKSHDFWLL FDDDIVEKID AQAIEEFYGL TSDISKNSES   360
GYILFYQSRD                                                         370

SEQ ID NO: 11            moltype = AA  length = 354
FEATURE                  Location/Qualifiers
REGION                   1..354
                         note = Description of Unknown: USP46 sequence
source                   1..354
                         mol_type = protein
                         organism = unidentified
SEQUENCE: 11
MTVRNIASIC NMGTNASALE KDIGPEQFPI NEHYFGLVNA LYFCRPFREN VLAYKAQQKK    60
KENLLTCLAD LFHSIATQKK KVGVIPPKKF ISRLRKENDL FDNYMQQDAH EFLNYLLNTI   120
ADILQEEKKQ EKQNGKLKNG NMNEPAENNK PELTWVHEIF QGTLTNETRC LNCETVSSKD   180
EDFLDLSVDV EQNTSITHCL RDFSNTETLC SEQKYYCETC CSKQEAQKRM RVKKLPMILA   240
LHLKRFKYME QLHRYTKLSY RVVFPLELRL FNTSSDAVNL DRMYDLVAVV VHCGSGPNRG   300
HYITIVKSHG FWLLFDDDIV EKIDAQAIEE FYGLTSDISK NSESGYILFY QSRE         354

SEQ ID NO: 12            moltype = DNA  length = 39
FEATURE                  Location/Qualifiers
misc_feature             1..39
                         note = Description of Artificial Sequence: Synthetic
                            oligonucleotide
source                   1..39
                         mol_type = other DNA
                         organism = synthetic construct
SEQUENCE: 12
atcttagagt gtcccatctg tctggagttg atcaaggaa                           39

SEQ ID NO: 13            moltype = AA  length = 13
FEATURE                  Location/Qualifiers
REGION                   1..13
                         note = Synthetic Construct
source                   1..13
                         mol_type = protein
                         organism = synthetic construct
SEQUENCE: 13
ILECPICLEL IKE                                                      13

SEQ ID NO: 14            moltype = DNA  length = 38
FEATURE                  Location/Qualifiers
misc_feature             1..38
                         note = Description of Artificial Sequence: Synthetic
                            oligonucleotide
source                   1..38
                         mol_type = other DNA
                         organism = synthetic construct
SEQUENCE: 14
atcttagagt gtcccatcgt ctggagttga tcaaggaa                            38

SEQ ID NO: 15            moltype = AA  length = 9
FEATURE                  Location/Qualifiers
REGION                   1..9
                         note = Synthetic Construct
source                   1..9
                         mol_type = protein
                         organism = synthetic construct
SEQUENCE: 15
ILECPIVWS                                                            9

SEQ ID NO: 16            moltype = DNA  length = 38
FEATURE                  Location/Qualifiers
misc_feature             1..38
                         note = Description of Artificial Sequence: Synthetic
                            oligonucleotide
source                   1..38
                         mol_type = other DNA
                         organism = synthetic construct
SEQUENCE: 16
atcttagagt gtcccatctt ctggagttga tcaaggaa                            38

SEQ ID NO: 17            moltype = AA  length = 9
FEATURE                  Location/Qualifiers
REGION                   1..9
```

```
                    note = Synthetic Construct
source              1..9
                    mol_type = protein
                    organism = synthetic construct
SEQUENCE: 17
ILECPIFWS                                                                  9

SEQ ID NO: 18       moltype = AA  length = 13
FEATURE             Location/Qualifiers
REGION              1..13
                    note = Description of Artificial Sequence: Synthetic peptide
source              1..13
                    mol_type = protein
                    organism = synthetic construct
SEQUENCE: 18
ILECPICLEL IKE                                                            13

SEQ ID NO: 19       moltype = AA  length = 9
FEATURE             Location/Qualifiers
REGION              1..9
                    note = Description of Artificial Sequence: Synthetic peptide
source              1..9
                    mol_type = protein
                    organism = synthetic construct
SEQUENCE: 19
ILECPIVWS                                                                  9

SEQ ID NO: 20       moltype = AA  length = 9
FEATURE             Location/Qualifiers
REGION              1..9
                    note = Description of Artificial Sequence: Synthetic peptide
source              1..9
                    mol_type = protein
                    organism = synthetic construct
SEQUENCE: 20
ILECPIFWS                                                                  9
```

What is claimed is:

1. A method for treating a human subject having, or at risk of developing, a cancer, the method comprising administering to the human subject an effective amount of a USP1 inhibitor and a PARP inhibitor, wherein the human subject is identified as having a BRCA1 and/or BRCA2 mutation.

2. The method of claim 1, wherein the USP1 inhibitor is
   (a) a small molecule inhibitor;
   (b) an inhibitory nucleic acid; or
   (c) an anti-USP1 antibody or USP1-binding fragment thereof.

3. The method of claim 2, wherein the small molecule inhibitor is ML323, C527, SJB019, or SJB2-043.

4. The method of claim 1, wherein the cancer is resistant to a cross-linking agent.

5. The method of claim 4, wherein the cross-linking agent is cisplatin, mitomycin, or busulfan.

6. The method of claim 1, wherein the cancer is:
   (a) breast cancer, prostate cancer, pancreatic cancer, fallopian tube cancer, peritoneal cancer, or ovarian cancer;
   (b) a basal-like carcinoma or a luminal breast cancer;
   (c) a triple-negative breast cancer; or
   (d) a high-grade serous ovarian carcinoma.

7. The method of claim 1, wherein the method comprises identifying the human subject as having
   (a) one or more cancer cells that have a BRCA1 mutation,
   (b) one or more cancer cells that have a BRCA1 and BRCA2 mutation, or
   (c) one or more cancer cells that have a BRCA2, BRCA1 and BRCA2, or Partner And Localizer of BRCA2 (PALB2) mutation.

8. The method of claim 1, wherein the USP1 inhibitor is an inhibitory nucleic acid or an anti-USP1 antibody or USP1-binding fragment thereof.

9. The method of claim 3, wherein the small molecule inhibitor is ML323.

10. The method of claim 5, wherein the cross-linking agent is busulfan.

11. The method of claim 1, wherein the cancer is:
    (a) fallopian tube cancer or peritoneal cancer;
    (b) luminal breast cancer;
    (c) a triple-negative breast cancer; or
    (d) a high-grade serous ovarian carcinoma.

12. The method of claim 1, wherein the method comprises identifying the human subject as having one or more cancer cells that have a Partner And Localizer of BRCA2 (PALB2) mutation.

\* \* \* \* \*